(12) United States Patent
Richelsoph et al.

(10) Patent No.: US 9,956,010 B2
(45) Date of Patent: *May 1, 2018

(54) POLYAXIAL PLATE ROD SYSTEM AND SURGICAL PROCEDURE

(71) Applicant: Intelligent Implant Systems, LLC, Charlotte, NC (US)

(72) Inventors: Marc Evan Richelsoph, Belmont, NC (US); David Frederick Waller, Charlotte, NC (US)

(73) Assignee: Intelligent Implant Systems, LLC, Charlotte, NC (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/250,137

(22) Filed: Aug. 29, 2016

(65) Prior Publication Data

US 2016/0361097 A1 Dec. 15, 2016

Related U.S. Application Data

(62) Division of application No. 14/697,362, filed on Apr. 27, 2015, now Pat. No. 9,526,531, which is a division (Continued)

(51) Int. Cl.
*A61B 17/70* (2006.01)
*A61B 17/80* (2006.01)
(Continued)

(52) U.S. Cl.
CPC ........ *A61B 17/7058* (2013.01); *A61B 17/701* (2013.01); *A61B 17/7001* (2013.01);
(Continued)

(58) Field of Classification Search
CPC ............ A61B 17/7035; A61B 17/7023; A61B 17/701; A61B 17/7058; A61B 17/7091;
(Continued)

(56) References Cited

U.S. PATENT DOCUMENTS 2,855,232 A 10/1958 Kozak
3,599,245 A 8/1971 Blatchford
(Continued)

FOREIGN PATENT DOCUMENTS

EP 1674042 A1 6/2006
FR 2790941 A1 9/2000
(Continued)

OTHER PUBLICATIONS

European Search Report for European Application No. 14852533 dated May 26, 2017.
(Continued)

*Primary Examiner* — Pedro Philogene
*Assistant Examiner* — David C Comstock
(74) *Attorney, Agent, or Firm* — Mayback & Hoffman, P.A.; Gregory L. Mayback

(57) ABSTRACT

An orthopedic fixation device comprising a bearing and a retaining portion. The bearing defines a bearing internal bore and has a rounded exterior surface, an upper surface, an intermediate surface, and a lower surface, and at least one slot in the bearing extending from the exterior surface to the internal bore. The retaining portion defines a recess shaped to accept the exterior surface of the bearing therein such that in a steady state of the bearing, the bearing can move within the recess, and, when at least one force is imparted against one of the upper and lower surfaces of the bearing, the bearing deforms outwardly to fix the bearing in place within the recess.

23 Claims, 41 Drawing Sheets

Related U.S. Application Data of application No. 14/507,517, filed on Oct. 6, 2014, now Pat. No. 9,044,273.

(60) Provisional application No. 61/887,676, filed on Oct. 7, 2013, provisional application No. 62/003,615, filed on May 28, 2014.

(51) Int. Cl.
*A61B 17/56* (2006.01)
*A61B 17/68* (2006.01)

(52) U.S. Cl.
CPC ...... *A61B 17/7007* (2013.01); *A61B 17/7011* (2013.01); *A61B 17/7014* (2013.01); *A61B 17/7023* (2013.01); *A61B 17/7035* (2013.01); *A61B 17/7074* (2013.01); *A61B 17/7076* (2013.01); *A61B 17/7082* (2013.01); *A61B 17/7091* (2013.01); *A61B 17/8057* (2013.01); *A61B 2017/567* (2013.01); *A61B 2017/681* (2013.01)

(58) Field of Classification Search
CPC ............ A61B 17/7007; A61B 17/7032; A61B 17/8038
USPC ....................... 606/60, 71, 70, 288, 246, 308
See application file for complete search history.

(56) References Cited

U.S. PATENT DOCUMENTS

| | | |
|---|---|---|
| 3,997,138 A | 12/1976 | Crock et al. |
| 4,041,939 A | 8/1977 | Hall |
| 4,269,178 A | 5/1981 | Keene |
| 4,404,967 A | 9/1983 | Bacal et al. |
| 4,411,259 A | 10/1983 | Drummond |
| 4,419,026 A | 12/1983 | Leto |
| 4,611,581 A | 9/1986 | Steffee |
| 4,706,367 A | 11/1987 | Garringer |
| 4,836,196 A | 6/1989 | Park et al. |
| 4,887,595 A | 12/1989 | Heinig et al. |
| 4,946,458 A | 7/1990 | Harms et al. |
| 4,947,835 A | 8/1990 | Hepburn et al. |
| 4,950,269 A | 8/1990 | Gaines |
| 5,010,879 A | 4/1991 | Moriya et al. |
| 5,036,837 A | 8/1991 | Mitchell et al. |
| 5,084,048 A | 1/1992 | Jacob et al. |
| 5,122,131 A | 6/1992 | Tsou |
| 5,129,899 A | 7/1992 | Small et al. |
| 5,176,679 A | 1/1993 | Lin |
| 5,201,734 A | 4/1993 | Cozad et al. |
| 5,261,913 A | 11/1993 | Marnay |
| 5,281,222 A | 1/1994 | Allard et al. |
| 5,356,411 A | 10/1994 | Spievack |
| 5,380,325 A | 1/1995 | Lahille et al. |
| 5,395,371 A | 3/1995 | Miller et al. |
| 5,443,467 A | 8/1995 | Biedermann et al. |
| 5,474,551 A | 12/1995 | Finn et al. |
| 5,476,462 A | 12/1995 | Allard et al. |
| 5,501,684 A | 3/1996 | Schlapfer et al. |
| 5,507,746 A | 4/1996 | Lin |
| 5,516,335 A | 5/1996 | Kummer et al. |
| 5,531,745 A | 7/1996 | Ray |
| 5,531,747 A | 7/1996 | Ray |
| 5,540,690 A | 7/1996 | Miller et al. |
| 5,545,163 A | 8/1996 | Miller et al. |
| 5,549,608 A | 8/1996 | Errico |
| 5,562,660 A | 10/1996 | Grob |
| 5,575,792 A | 11/1996 | Errico et al. |
| 5,578,033 A | 11/1996 | Errico et al. |
| 5,584,834 A | 12/1996 | Errico |
| 5,586,984 A | 12/1996 | Errico |
| 5,630,817 A | 5/1997 | Rokegem et al. |
| 5,591,165 A | 7/1997 | Jackson |
| 5,728,098 A | 3/1998 | Sherman |
| 5,733,284 A | 3/1998 | Martin |
| 5,733,285 A | 3/1998 | Errico |
| 5,716,356 A | 10/1998 | Biedermann et al. |
| 5,879,350 A | 3/1999 | Sherman et al. |
| 5,882,350 A | 3/1999 | Ralph et al. |
| 5,891,145 A | 4/1999 | Morrison |
| 5,954,725 A | 9/1999 | Sherman et al. |
| 5,984,928 A | 11/1999 | Hermann |
| 6,022,350 A | 2/2000 | Ganem |
| 6,045,552 A | 4/2000 | Zucherman et al. |
| 6,063,090 A | 5/2000 | Schlapfer |
| 6,113,601 A | 9/2000 | Tatar |
| 6,132,432 A | 10/2000 | Richelsoph |
| 6,206,879 B1 | 3/2001 | Marnay et al. |
| 6,248,105 B1 | 6/2001 | Schlapfer et al. |
| 6,254,602 B1 | 7/2001 | Justis |
| 6,273,888 B1 | 8/2001 | Justis |
| 6,290,703 B1 | 9/2001 | Ganem |
| 6,302,888 B1 | 10/2001 | Mellinger et al. |
| 6,355,040 B1 | 3/2002 | Richelsoph et al. |
| 6,379,354 B1 | 4/2002 | Rogozinski |
| 6,554,834 B1 | 4/2003 | Crozet et al. |
| 6,582,400 B1 | 6/2003 | Hawk et al. |
| 6,585,737 B1 | 7/2003 | Braccelli et al. |
| 6,623,485 B2 | 9/2003 | Doubler et al. |
| 6,626,904 B1 | 9/2003 | Jammet et al. |
| 6,641,586 B2 | 11/2003 | Varieur |
| 6,755,829 B1 | 6/2004 | Bono et al. |
| 6,770,094 B2 | 8/2004 | Fehling et al. |
| 6,843,791 B2 | 1/2005 | Serhan |
| 6,911,030 B1 | 6/2005 | Vanacker et al. |
| 6,964,666 B2 | 11/2005 | Jackson |
| 7,163,539 B2 | 1/2007 | Abdelgany |
| 7,186,255 B2 | 3/2007 | Baynham |
| 7,207,992 B2 | 4/2007 | Ritland |
| 7,326,210 B2 | 2/2008 | Jahng et al. |
| 7,591,839 B2 | 9/2009 | Biedermann et al. |
| 7,686,833 B1 | 3/2010 | Muhanna et al. |
| 7,736,380 B2 | 6/2010 | Johnston et al. |
| 7,803,174 B2 | 9/2010 | Denis et al. |
| 7,806,913 B2 | 10/2010 | Fanger et al. |
| 7,867,255 B2 | 1/2011 | Miller et al. |
| 7,931,675 B2 | 4/2011 | Panjabi et al. |
| 7,935,134 B2 | 5/2011 | Reglos et al. |
| 7,935,137 B2 | 5/2011 | Gorhan et al. |
| 7,981,141 B2 | 7/2011 | Morrison et al. |
| 7,981,142 B2 | 7/2011 | Konieczynski et al. |
| 8,002,806 B2 | 8/2011 | Justis |
| 8,002,808 B2 | 8/2011 | Morrison et al. |
| 8,007,523 B2 | 8/2011 | Wagner et al. |
| 8,012,188 B2 | 9/2011 | Melkent et al. |
| 8,048,123 B2 | 11/2011 | Mitchell et al. |
| 8,062,338 B2 | 11/2011 | McBride et al. |
| 8,062,341 B2 | 11/2011 | Binder et al. |
| 8,062,367 B2 | 11/2011 | Kirschman |
| 8,092,498 B2 | 1/2012 | Samudrala et al. |
| 8,092,501 B2 | 1/2012 | Mitchell et al. |
| 8,172,885 B2 | 5/2012 | Songer et al. |
| 8,197,519 B2 | 6/2012 | Schlaepfer |
| 8,216,285 B2 | 7/2012 | Markworth |
| 8,221,476 B2 | 7/2012 | Paul |
| 8,236,033 B2 | 8/2012 | Paul |
| 8,236,034 B2 | 8/2012 | Binder et al. |
| 8,262,708 B2 | 9/2012 | Michelson |
| 8,277,493 B2 | 10/2012 | Farris et al. |
| 8,323,283 B2 | 12/2012 | Michelson |
| 8,348,982 B2 | 1/2013 | Baynham et al. |
| 8,361,125 B2 | 1/2013 | Taylor et al. |
| 8,361,126 B2 | 1/2013 | Perrow et al. |
| 8,361,129 B2 | 1/2013 | Chao |
| 8,372,152 B2 | 2/2013 | Kirschman |
| 8,382,809 B2 | 2/2013 | Kaufman et al. |
| 8,403,970 B1 | 3/2013 | Bedor |
| 8,403,971 B2 | 3/2013 | Barrus et al. |
| 8,409,259 B1 | 4/2013 | Bedor |
| 8,409,260 B2 | 4/2013 | Biedermann et al. |
| 8,425,514 B2 | 4/2013 | Anderson et al. |
| 8,425,576 B2 | 4/2013 | Anderson et al. |

(56) References Cited

U.S. PATENT DOCUMENTS

| | | |
|---|---|---|
| 8,435,266 B2 | 5/2013 | Richelsoph |
| 8,439,923 B2 | 5/2013 | Won et al. |
| 8,480,716 B2 | 7/2013 | Perrow et al. |
| 8,652,176 B2 | 2/2014 | Ramadan et al. |
| 8,652,178 B2 | 2/2014 | Abelgany |
| 8,672,978 B2 | 3/2014 | Dant et al. |
| 8,672,984 B2 | 3/2014 | Lindemann et al. |
| 8,764,804 B2 | 7/2014 | Rezach |
| 8,771,319 B2 | 7/2014 | Prajapati |
| 8,795,340 B2 | 8/2014 | Weiman |
| 8,840,649 B2 | 9/2014 | De Coninck |
| 8,998,952 B2 * | 4/2015 | Fauth ............ A61B 17/1671 606/247 |
| 9,044,273 B2 * | 6/2015 | Richelsoph ......... A61B 17/7001 |
| 9,526,531 B2 * | 12/2016 | Richelsoph ......... A61B 17/7001 |
| 2001/0012937 A1 | 8/2001 | Schaffler-Wachter et al. |
| 2001/0047173 A1 | 11/2001 | Schlapfer et al. |
| 2002/0032443 A1 | 3/2002 | Sherman et al. |
| 2002/0052603 A1 | 5/2002 | Nichols et al. |
| 2003/0023240 A1 | 1/2003 | Amrein et al. |
| 2003/0023243 A1 | 1/2003 | Biedermann et al. |
| 2003/0093078 A1 | 5/2003 | Ritland |
| 2003/0216735 A1 | 11/2003 | Altarac |
| 2004/0097933 A1 | 5/2004 | Lourdel et al. |
| 2004/0127899 A1 | 7/2004 | Konieczynski et al. |
| 2004/0143264 A1 | 7/2004 | McAfee |
| 2004/0049190 A1 | 11/2004 | Biedermann et al. |
| 2004/0225289 A1 | 11/2004 | Biedermann et al. |
| 2004/0260284 A1 | 12/2004 | Parker |
| 2004/0267264 A1 * | 12/2004 | Konieczynski .... A61B 17/7032 606/289 |
| 2005/0080415 A1 | 4/2005 | Keyer et al. |
| 2005/0085812 A1 | 4/2005 | Sherman et al. |
| 2005/0171542 A1 | 4/2005 | Biedermann et al. |
| 2005/0096653 A1 | 5/2005 | Doubler et al. |
| 2005/0143737 A1 | 6/2005 | Pafford et al. |
| 2005/0171537 A1 | 8/2005 | Mazel et al. |
| 2005/0203516 A1 | 9/2005 | Biedermann et al. |
| 2005/0203517 A1 | 9/2005 | Jahng et al. |
| 2005/0215001 A1 | 9/2005 | Okada |
| 2005/0216001 A1 | 9/2005 | David |
| 2005/0216003 A1 | 9/2005 | Biedermann et al. |
| 2005/0222570 A1 | 10/2005 | Jackson |
| 2005/0228379 A1 | 10/2005 | Jackson |
| 2005/0261687 A1 | 11/2005 | Garamszegi |
| 2005/0267472 A1 | 12/2005 | Biedermann et al. |
| 2005/0267485 A1 | 12/2005 | Cordes et al. |
| 2005/0277924 A1 | 12/2005 | Roychowdhury |
| 2005/0277927 A1 | 12/2005 | Guenther |
| 2006/0004357 A1 | 1/2006 | Lee |
| 2006/0009767 A1 | 1/2006 | Kiester |
| 2006/0036240 A1 | 2/2006 | Colleran et al. |
| 2006/0036242 A1 | 2/2006 | Nilsson |
| 2006/0036252 A1 | 2/2006 | Baynham |
| 2006/0052786 A1 | 3/2006 | Dant et al. |
| 2006/0058788 A1 | 3/2006 | Hammer |
| 2006/0058789 A1 | 3/2006 | Kim et al. |
| 2006/0074419 A1 | 4/2006 | Taylor et al. |
| 2006/0084979 A1 | 4/2006 | Jackson |
| 2006/0095038 A1 | 5/2006 | Jackson |
| 2006/0100621 A1 | 5/2006 | Jackson |
| 2006/0100622 A1 | 5/2006 | Jackson |
| 2006/0149233 A1 | 7/2006 | Richelsoph |
| 2006/0149240 A1 | 7/2006 | Jackson |
| 2006/0149241 A1 | 7/2006 | Richelsoph |
| 2006/0155279 A1 | 7/2006 | Ogilvie |
| 2006/0161152 A1 | 7/2006 | Ensign et al. |
| 2006/0173456 A1 | 8/2006 | Hawkes et al. |
| 2006/0200133 A1 | 9/2006 | Jackson |
| 2006/0200147 A1 | 9/2006 | Ensign et al. |
| 2006/0229606 A1 | 10/2006 | Clement et al. |
| 2006/0233597 A1 | 10/2006 | Ensign et al. |
| 2006/0235385 A1 | 10/2006 | Whipple |
| 2006/0235392 A1 | 10/2006 | Hammer |
| 2006/0235393 A1 | 10/2006 | Bono |
| 2006/0241594 A1 | 10/2006 | McCarthy et al. |
| 2006/0241599 A1 | 10/2006 | Konieczynski |
| 2006/0241603 A1 | 10/2006 | Jackson |
| 2006/0247635 A1 | 11/2006 | Gordon et al. |
| 2006/0264937 A1 | 11/2006 | White |
| 2006/0265074 A1 | 11/2006 | Krishna et al. |
| 2006/0271047 A1 | 11/2006 | Jackson |
| 2006/0276789 A1 | 12/2006 | Jackson |
| 2006/0276792 A1 | 12/2006 | Ensign et al. |
| 2007/0010817 A1 | 1/2007 | De Coninck |
| 2007/0016204 A1 | 1/2007 | Martinez et al. |
| 2007/0055235 A1 | 3/2007 | Janowski |
| 2007/0055242 A1 | 3/2007 | Bailly |
| 2007/0093817 A1 | 4/2007 | Barrus et al. |
| 2007/0093820 A1 | 4/2007 | Freudiger et al. |
| 2007/0093832 A1 | 4/2007 | Abdelgany |
| 2007/0093838 A1 | 4/2007 | Khodadadyan-Klostermann et al. |
| 2007/0233080 A1 | 4/2007 | Na et al. |
| 2007/0118122 A1 | 5/2007 | Buller et al. |
| 2007/0118123 A1 | 5/2007 | Strausbaugh et al. |
| 2007/0123867 A1 | 5/2007 | Kirschman |
| 2007/0157543 A1 | 7/2007 | Metz-Stavenhagen |
| 2007/0161999 A1 | 7/2007 | Biedermann |
| 2007/0167948 A1 | 7/2007 | Abdou |
| 2007/0167949 A1 | 7/2007 | Altarac et al. |
| 2007/0173817 A1 | 7/2007 | Sournac et al. |
| 2007/0173818 A1 | 7/2007 | Hestad et al. |
| 2007/0173819 A1 | 7/2007 | Sandlin |
| 2007/0173833 A1 | 7/2007 | Buller |
| 2007/0225707 A1 | 9/2007 | Wisnewski et al. |
| 2007/0233086 A1 | 10/2007 | Harms |
| 2007/0233087 A1 | 10/2007 | Schlapfer |
| 2007/0239159 A1 | 10/2007 | Altarac et al. |
| 2007/0270818 A1 | 11/2007 | Rezach |
| 2008/0015588 A1 | 1/2008 | Hawkes |
| 2008/0027436 A1 | 1/2008 | Cournoyer et al. |
| 2008/0077139 A1 | 3/2008 | Landry et al. |
| 2008/0119853 A1 | 5/2008 | Felt et al. |
| 2008/0172093 A1 | 7/2008 | Nilsson |
| 2008/0177321 A1 | 7/2008 | Drewry |
| 2008/0183212 A1 | 7/2008 | Veldrnan et al. |
| 2008/0183213 A1 | 7/2008 | Veldrnan et al. |
| 2008/0195153 A1 | 8/2008 | Thompson |
| 2008/0195159 A1 | 8/2008 | Kloss et al. |
| 2008/0208260 A1 | 8/2008 | Truckai et al. |
| 2008/0243189 A1 | 10/2008 | Purcell et al. |
| 2008/0262553 A1 | 10/2008 | Hawkins et al. |
| 2009/0093820 A1 | 4/2009 | Trieu et al. |
| 2009/0204155 A1 | 8/2009 | Aschmann |
| 2009/0204156 A1 | 8/2009 | McClintock et al. |
| 2009/0248088 A1 | 10/2009 | Biedermann |
| 2009/0254123 A1 | 10/2009 | Pafford et al. |
| 2009/0287260 A1 | 11/2009 | Zehnder |
| 2009/0326584 A1 | 12/2009 | Slivka et al. |
| 2010/0036423 A1 | 2/2010 | Hayes et al. |
| 2010/0057126 A1 | 3/2010 | Hestad |
| 2010/0063551 A1 | 3/2010 | Richelsoph |
| 2010/0087865 A1 | 4/2010 | Biedermann et al. |
| 2010/0114318 A1 | 5/2010 | Gittings et al. |
| 2010/0137913 A1 | 6/2010 | Khatchadourian et al. |
| 2010/0185247 A1 | 7/2010 | Richelsoph |
| 2010/0217319 A1 | 8/2010 | Todd |
| 2010/0331884 A1 | 12/2010 | Hestad |
| 2010/0331886 A1 | 12/2010 | Fanger et al. |
| 2011/0004251 A1 | 1/2011 | Sweeney et al. |
| 2011/0077691 A1 | 3/2011 | De Coninck |
| 2011/0196423 A1 | 8/2011 | Ziolo et al. |
| 2011/0213419 A1 | 9/2011 | Richelsoph |
| 2011/0230916 A1 | 9/2011 | Richelsoph |
| 2011/0245873 A1 | 10/2011 | Winslow et al. |
| 2011/0270314 A1 | 11/2011 | Mueller et al. |
| 2012/0130427 A1 | 5/2012 | Hoffman et al. |
| 2013/0190825 A1 | 7/2013 | Perrow et al. |
| 2014/0228895 A1 | 8/2014 | Ziolo et al. |

FOREIGN PATENT DOCUMENTS

| | | |
|---|---|---|
| WO | 1997002786 | 1/1997 |
| WO | 2000018310 A | 4/2000 |

(56) References Cited

FOREIGN PATENT DOCUMENTS

| WO | 2005074823 A1 | 8/2005 |
|----|---------------|--------|
| WO | 2006060430    | 6/2006 |
| WO | 2006065607    | 6/2006 |
| WO | 2007082019 A2 | 7/2007 |
| WO | 2008078163 A2 | 7/2008 |

OTHER PUBLICATIONS

European Search Report of European App. No. 12 16 7524 dated Jan. 31, 2013.
International Search Report and Written Opinion of the International Searching Authority, dated Jan. 16, 2015 by the International Searching Authority, in reference to PCT Application No. PCT/US2014/059475.
International Search Report of PCT App. No. PCT/US2009/056343 dated Nov. 25, 2009.
Japanese Notification of Reasons for Refusal for Japanese Patent Application No. 2011-526300 dated Sep. 9, 2013.
Japanese Notification of Reasons for Refusal, Final, for Japanese Patent Application No. 2011-526300 dated Aug. 1, 2014.
Patent Examination Report of Australian Patent App. No. 2008317087 dated Feb. 14, 2013.
Stryker, Techtonix Surgical Protocol, Stryker Spine, Literature No. TLTCTSTIA, Feb. 2006, Allendale, New Jersey.
Supplementary European Search Report of European Patent App. No. 09 81 3525 dated Feb. 6, 2013.

\* cited by examiner

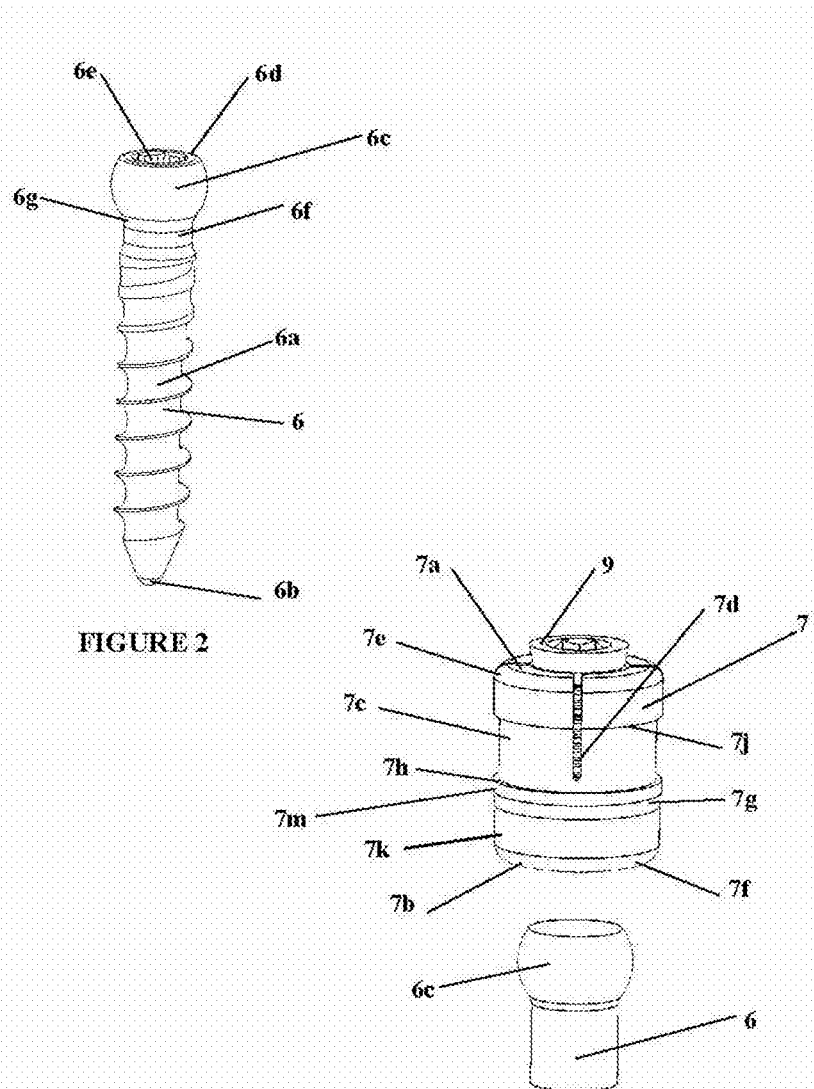

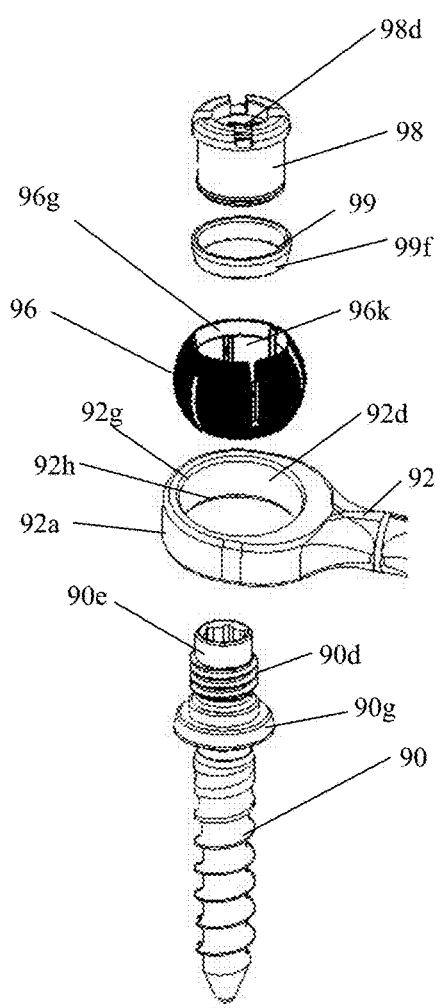
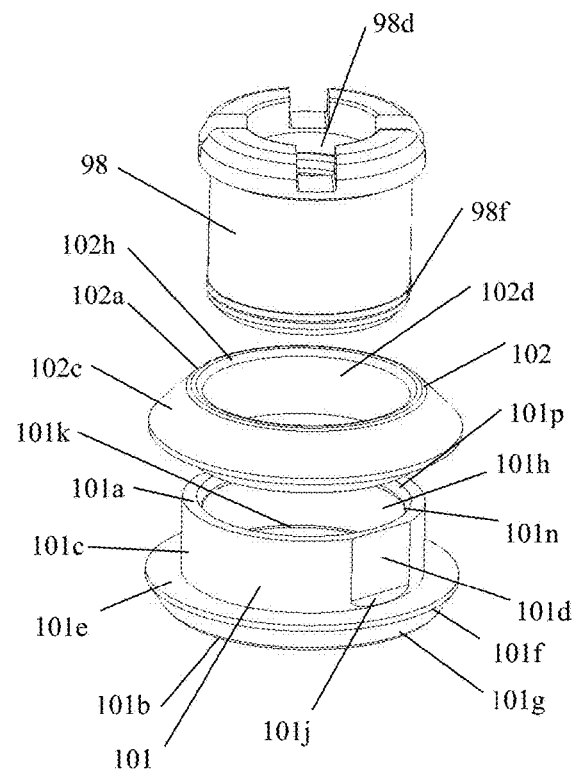
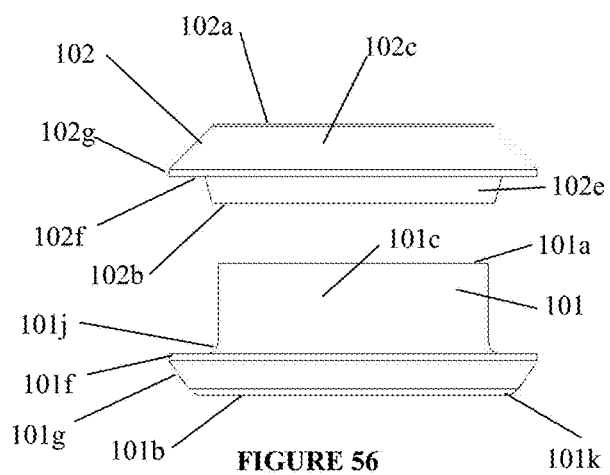
FIGURE 54
FIGURE 55
FIGURE 56

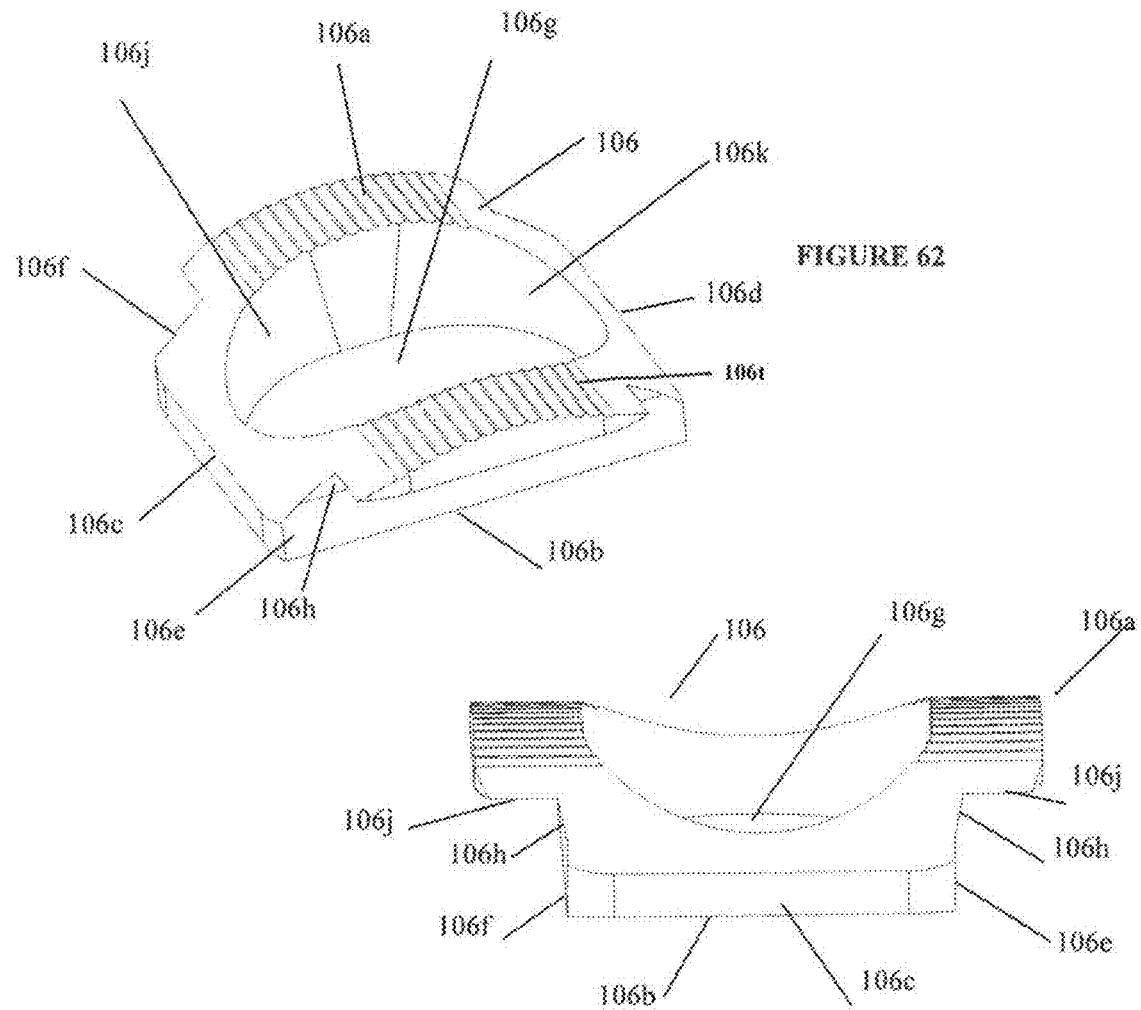
FIGURE 62
FIGURE 63
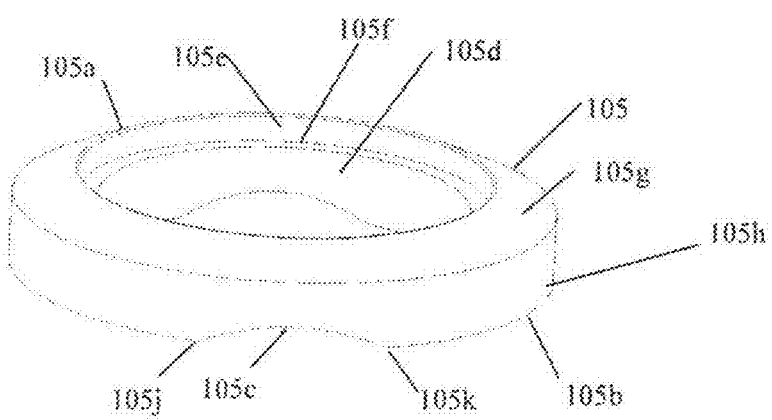
FIGURE 64

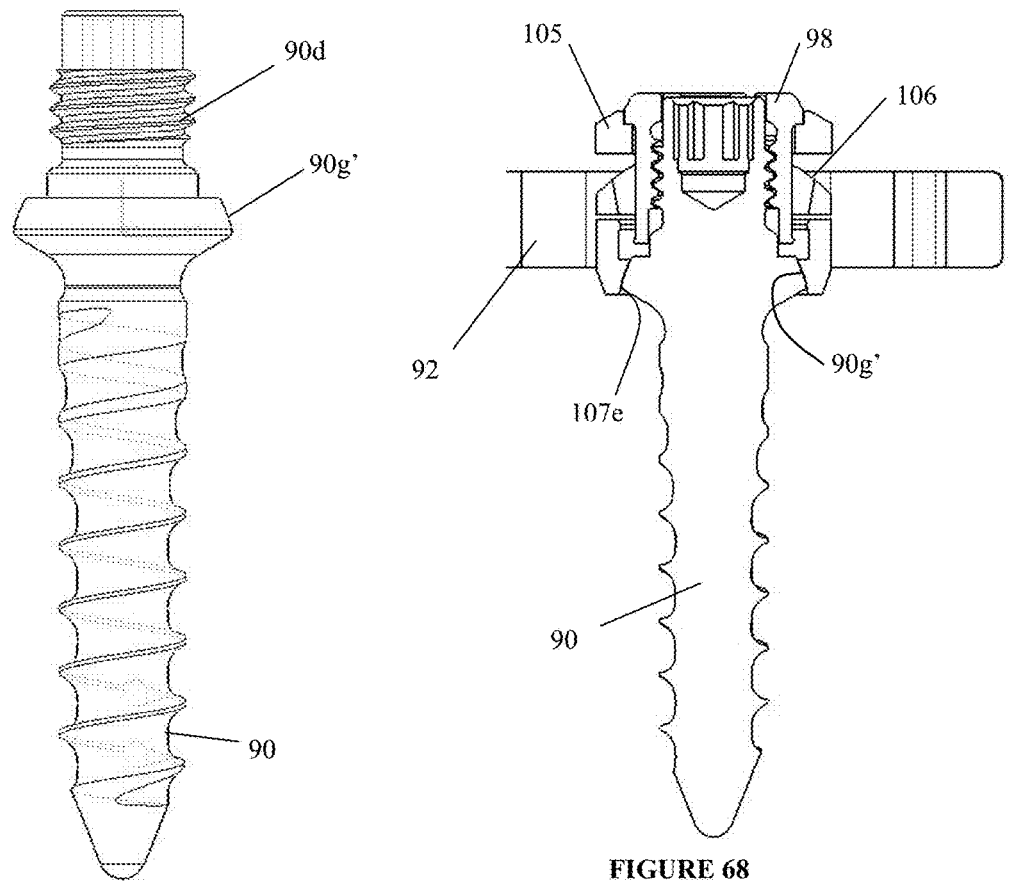
FIGURE 67
FIGURE 68
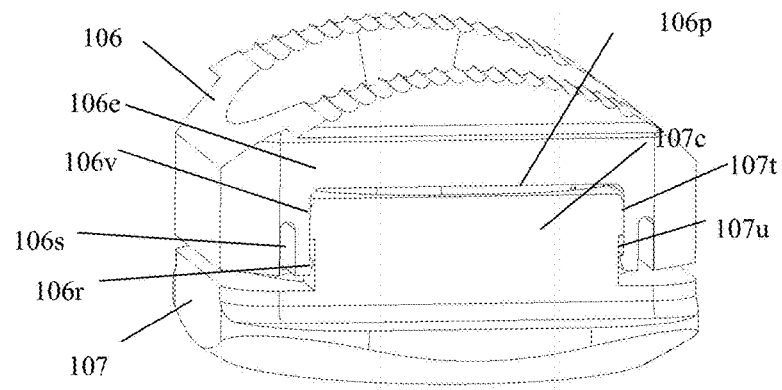
FIGURE 68A

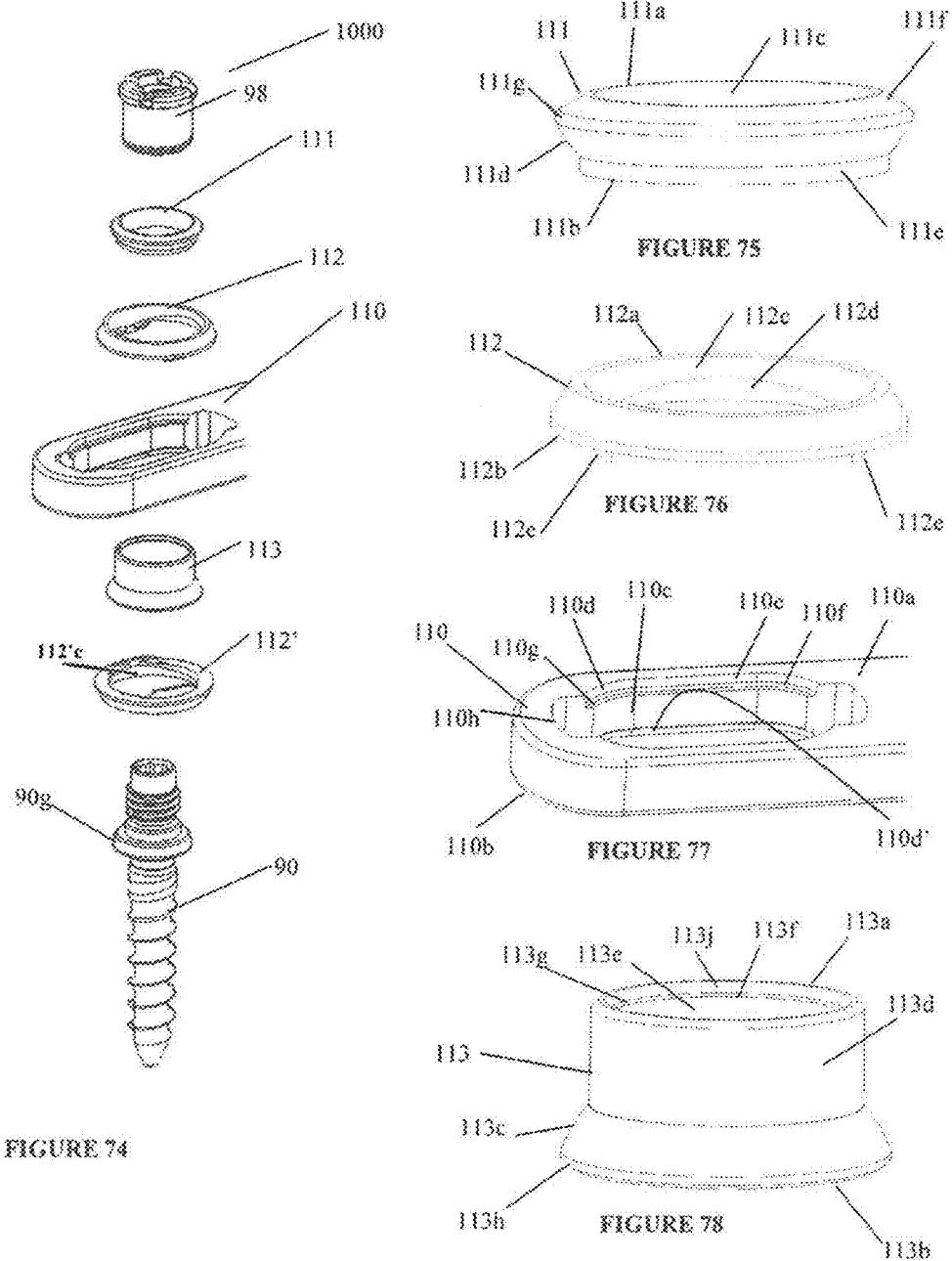

POLYAXIAL PLATE ROD SYSTEM AND SURGICAL PROCEDURE

CROSS-REFERENCE TO RELATED APPLICATIONS

This application:
is a divisional of U.S. patent application Ser. No. 14/697,362, filed on Apr. 27, 2015, which application:
 is a divisional of U.S. patent application Ser. No. 14/507,517, filed on Oct. 6, 2014, now U.S. Pat. No. 9,044,273, issued Jun. 2, 2015 (which application claims priority to U.S. Provisional Application Ser. Nos. 61/887,676, filed on Oct. 7, 2013, and 62/003,615, filed on May 28, 2014),
the entire disclosures of which are hereby incorporated herein by reference in their entireties.

FIELD OF THE INVENTION

The present invention lies in the field of spinal implants. The present disclosure relates to an implant and surgical procedure for insertion of a spinal implant. More specifically, the present invention relates to an implant connecting member that has the ability to connect multiple bone screws while adjusting for angulation and distance between the bone screws. This assists the surgeon in connecting implants at different angles without bending or contouring the connecting member. This provides the benefits of more accurate and easier connecting of two or more implants and significantly reducing surgical instrumentation while minimizing patient trauma and reducing surgical time.

BACKGROUND OF THE INVENTION

The insertion of pedicle screws into the spine for fixation has been commonly used for many years. In general, a set of implants is placed on both sides of the spinous process into the pedicles and the set on each side is connected by an individual rod. For example, in a single level fusion, whereby two vertebral bodies are intended to be fused together, four pedicle screws are used, two on each side of the spinous process. Each set of two is then connected by the rod. For multiple levels, more screws are used and connected by longer rods. The general technique is an open procedure, whereby the incision in the skin is long and spans the length of the affected area of the spine to be treated. As alternative to rod based systems, plating systems, where a plate forms the connector between two or more screws, has been used in the spine for a long time. Plating systems, such as those shown in U.S. Pat. No. 4,611,581 to Steffee and U.S. Pat. No. 4,887,595 to Heinig et al., use rigid plates to connect the screws placed within the pedicles. Rod-based systems are significantly more popular for fixation in the posterior lumbar spine due to the complexity of the anatomy.

The lumbar spine includes multiple vertebrae that, in a healthy spine, are flexibly held within a general S-curve. Each vertebra is a different size and different geometry. The pedicles on each vertebra, which are posts that extend from the vertebral body, vary in angle and distance apart from one vertebral body to the next. While a rod can be contoured or bent to meet the anatomy, this is extremely difficult, if not impossible to do well with a rigid plating system, as plates can be contoured to match the S curve, but resist contouring in other directions.

To avoid contouring, systems such as that covered under U.S. Pat. No. 6,379,354 by Rogozinski, break long plates into smaller plates that connect one pair of screws at a time. The system is difficult to use and requires significant implant inventory, as each link covers only one distance between two screws and has no adjustability. There are also other drawbacks such as overall system height and profile Therefore, while these prior plating systems and surgical procedures can be suitable for limited usage to which they somewhat address, they are not suitable to providing an implant and surgical approach that can accurately and securely connect multiple screws together, adjust for anatomical variations, provide a low profile system, and significantly reduce the quantity of implant and instruments needed while reducing surgical complexity.

Thus, a need exists to overcome the problems with the prior art systems, designs, and processes as discussed above.

SUMMARY OF THE INVENTION

The invention provides a new implant system for adjusting to the anatomy of the spine and connecting two or more vertebral bodies securely that overcomes the mentioned disadvantages of the heretofore-known devices and methods of this general type and that provide such features by substantially departing from the conventional concepts and designs of the prior art, and in so doing allow simpler and more accurate connection of multiple spinal implants while providing a small overall size leading to less trauma to soft tissue.

The present invention relates to a spinal connecting member. More specifically, the invention is directed to an implant connecting member that has the ability to adjust to angulation and distance of two or more bone screw anchors and to assist the surgeon in connecting implants at different angles and distances. When the angulation and distance needed is set, the device allows for locking of the angle and distance.

The present invention provides for a plate for attachment to spinal implants.

The present invention provides for a plate for attachment to spinal implants where the spinal implants are bone screws.

The present invention provides for a plate for attachment to spinal implants where the spinal implants are polyaxial bone screws The present invention provides for a plate for attachment to spinal implants where the spinal implants are monoaxial bone screws The present invention provides for a plate for attachment to spinal implants where the spinal implants are monoaxial bone screws with a spherical external shape.

The present invention provides for a plate for attachment to spinal implants where the spinal implants have at least one slot.

The present invention provides for a plate for attachment to spinal implants where the spinal implants have at multiple slots.

The present invention provides for a plate for attachment to spinal implants where the spinal implants have a locking feature.

The present invention provides for a plate for attachment to spinal implants where the spinal implants have a locking feature and a chamfer or taper.

The present invention provides for a plate for attachment to spinal implants where the spinal implants have a locking feature that causes at least a portion of the outside surface of the spinal implant to move outward.

The present invention provides for a plate for attachment to spinal implants where the spinal implants have a locking feature where the locking feature is a set screw having a section of the set screw with a chamfer or taper.

The present invention provides for a plate for attachment to spinal implants where the spinal implants have a locking feature where the locking feature is a set screw having a section of the set screw with a chamfer or taper, the set screw chamfer or taper engaging a chamfer or taper in the spinal implant, such that tightening the set screw causes at least a portion of the spinal implant body to flair outward.

The present invention provides for a plate for attachment to spinal implants where the spinal implants have a locking feature that is a set screw where the bottom of the set screw contacts an inside surface of the spinal implant such that tightening the set screw causes at least a portion of the spinal implant body to flair outward.

The present invention provides for a plate for attachment to spinal implants where the spinal implants have a locking feature that is a cam, whereby turning the cam causes at least a portion of the spinal implant body to flair outward.

The present invention provides for a plate for attachment to spinal implants where the spinal implants have a locking feature that is self-contained within the spinal implant.

The present invention provides for a plate for attachment to spinal implants, the plate having the ability to adjust for different distances between two spinal implants.

The present invention provides for a plate for attachment to spinal implants where the amount of adjustment for different distances between two spinal implants can be increased as the plate length is increased.

The present invention provides for a plate for attachment to spinal implants where the plate has the ability to adjust and compensate for differences in angulation between two spinal implants.

The present invention provides for a plate for attachment to spinal implants where the plate has the ability to adjust and compensate for differences in angulation between two spinal implants and the ability to adjust for different distances between two spinal implants.

The present invention provides for a series of plates for attachment to spinal implants where the plate has the ability to adjust and compensate for differences in angulation between two spinal implants and the ability to adjust for different distances between two spinal implants.

The present invention provides for a plate for attachment to spinal implants where the plate has the ability to adjust and compensate for differences in angulation between two spinal implants by attaching to a polyaxial screw assembly, the polyaxial assembly including a bone screw with a head, a polyaxial screw body and an insert that connects to and rotates about the bone screw head.

The present invention provides for a plate for attachment to spinal implants where the plate has the ability to adjust and compensate for differences in angulation between two spinal implants by attaching to a polyaxial screw assembly, the polyaxial assembly including a bone screw with a head, a polyaxial screw body and an insert that connects to and rotates about the bone screw head, where the angulation of the plate can be locked by locking the polyaxial assembly, thereby tightening the insert against the bone screw head.

The present invention provides for a plate for attachment to spinal implants where the plate has the ability to adjust and compensate for differences in angulation between two spinal implants by attaching to a polyaxial screw assembly, the polyaxial assembly including a bone screw with a head, a polyaxial screw body and an insert such that the bone screw and head can be attached to the bone first and the polyaxial screw body and insert snapped over the bone screw head prior to attaching the plate.

The present invention provides for a plate for attachment to spinal implants where the plate contains an opening for a spherical bearing and a spherical bearing that can rotate within the opening in the plate.

The present invention provides for a plate for attachment to spinal implants where the plate contains an opening for a spherical bearing and a spherical bearing that can rotate within the opening in the plate where the plate is contoured to match the curvature of the spine.

The present invention provides for a plate for attachment to spinal implants where the plate contains an opening for a spherical bearing and a spherical bearing that can rotate within the opening in the plate, the plate opening being shaped to retain the spherical bearing.

The present invention provides for a plate for attachment to spinal implants where the plate contains an opening for a spherical bearing and a spherical bearing that can rotate within the opening in the plate, the plate opening having at least a partially spherically surface to retain the spherical bearing.

The present invention provides for a plate for attachment to spinal implants where the plate contains an opening for a spherical bearing and a spherical bearing that can rotate within the opening in the plate, the plate opening having a shape other than spherical, such as a cylinder with two internal rings or chamfers to retain the spherical bearing.

The present invention provides for a plate for attachment to spinal implants where the plate contains an opening for a spherical bearing and the spherical bearing can be pressed into the opening in the plate.

The present invention provides for a plate for attachment to spinal implants where the plate contains an opening for a spherical bearing and a spherical bearing, the spherical bearing having at least one slot to allow the bearing to flex inward.

The present invention provides for a plate for attachment to spinal implants where the plate contains an opening for a spherical bearing and a spherical bearing having multiple slots to allow the bearing to flex inward.

The present invention provides for a plate for attachment to spinal implants where the plate contains an opening for a spherical bearing and a spherical bearing having multiple slots to allow the bearing to flex inward, and the slots are of uniform height and width.

The present invention provides for a plate for attachment to spinal implants where the plate contains an opening for a spherical bearing and a spherical bearing having multiple slots to allow the bearing to flex inward, and the slots are of varying height and/or width.

The present invention provides for a plate for attachment to spinal implants whereby the plate contains an opening for a spherical bearing and a spherical bearing where the spherical bearing is a section of a sphere and has a diameter and a length.

The present invention provides for a plate for attachment to spinal implants where the plate contains an opening for a spherical bearing and a spherical bearing being a section of a sphere and having a diameter and a length and an inner opening.

The present invention provides for a plate for attachment to spinal implants where the plate contains an opening for a spherical bearing and a spherical bearing being a section of a sphere and having a diameter and a length and an inner opening, the inner opening being a cylindrical bore for accepting a spinal implant.

The present invention provides for a plate for attachment to spinal implants where the plate contains an opening for a spherical bearing and a spherical bearing being a section of a sphere and having a diameter and a length and an inner opening, the inner opening being a cylindrical bore having additional features, such as a step, for attaching to a spinal implant.

The present invention provides for a plate for attachment to spinal implants where the plate contains an opening for a spherical bearing and a spherical bearing being a section of a sphere and having a diameter and a length and an inner opening, the inner opening not being cylindrical and another shape, such as square, hexagonal, or other shape, optionally having additional features, such as a step, for attaching to a spinal implant.

The present invention provides for a plate for attachment to spinal implants where the plate contains an opening for a spherical bearing and a spherical bearing having a smooth external surface.

The present invention provides for a plate for attachment to spinal implants where the plate contains an opening for a spherical bearing, the spherical bearing having an external surface that is textured or roughened by a machining, forming, or finishing process.

The present invention provides for a plate for attachment to spinal implants where the plate contains an opening for a spherical bearing and a spherical bearing having an external surface that is textured by machining a series of grooves into the surface of the bearing.

The present invention provides for a plate for attachment to spinal implants where the plate contains an oblong opening for accepting a spinal implant therewithin.

The present invention provides for a plate for attachment to spinal implants where the plate contains an oblong opening for accepting a spinal implant therewithin such that a portion of the inside surface of the plate oblong opening contacts or can be forced to contact the spinal implant when the spinal implant is locked to the plate.

The present invention provides for a plate for attachment to spinal implants where the plate contains an oblong opening for accepting a spinal implant therewithin and a spinal implant has a groove in the side such that a portion of the inside surface of the plate oblong opening fits within the groove in the side of the spinal implant.

The present invention provides for a plate for attachment to spinal implants where the plate contains an oblong opening for accepting a spinal implant therewithin and a spinal implant has a groove in the side such that a portion of the inside surface of the plate oblong opening fits within the groove in the side of the spinal implant and the spinal implant can slide within the oblong opening.

The present invention provides for a plate for attachment to spinal implants where the plate contains an oblong opening for accepting a sliding component therewithin.

The present invention provides for a plate for attachment to spinal implants where the plate contains an oblong opening for accepting a sliding component therewithin, the oblong opening having a recessed pocket to accept a sliding component.

The present invention provides for a plate for attachment to spinal implants where the plate contains an oblong opening for accepting a sliding component therewithin, the oblong opening having walls of the opening or a recessed pocket that is smooth.

The present invention provides for a plate for attachment to spinal implants where the plate contains an oblong opening for accepting a sliding component therewithin, the oblong opening whereby the walls of the opening or recessed pocket is textured.

The present invention provides for a plate for attachment to spinal implants where the plate contains an oblong opening for accepting a sliding component therewithin, the oblong opening having a length that is longer than the length of the sliding component.

The present invention provides for a plate for attachment to spinal implants where the plate contains an oblong opening for accepting a sliding component therewithin, the sliding component having an opening for accepting a spinal implant.

The present invention provides for a sliding component having an opening for accepting a spinal implant and at least one slot such that sliding component can contract and expand.

The present invention provides for a sliding component having an opening for accepting a spinal implant and at least one slot such that the sliding component can contract such that it can be pushed into the oblong opening in the plate and subsequently expanded so it can be retained in the plate.

The present invention provides for a sliding component shaped to fit within a recess in the plate.

The present invention provides for a sliding component shaped to fit within a recess in the plate while having a portion above and/or below the plate.

The present invention provides for a sliding component within an opening in a plate or other connector, the sliding component having an opening for accepting a spinal implant and at least one slot such that the sliding component can be forced outward by locking of the spinal implant such that at least a portion of the external wall of the slider is forced to engage at least a portion of the inside of the opening of the plate or connector.

The present invention provides for a sliding component within an opening in a plate or other connector, the sliding component having an opening for accepting a spinal implant and at least one slot such that the sliding component can be forced outward by locking of the spinal implant such that at least a portion of the external wall of the slider is forced to engage at least a portion of the inside of the opening of the plate or connector, effectively locking the position of the slider relative to the plate or connector.

The present invention provides for a sliding component within an opening in a plate or other connector, the sliding component having an opening for accepting a spherical bearing.

The present invention provides for a plate for attachment to spinal implants where the plate contains an opening to accept a spherical bearing or spinal implant with a spherical surface and an oblong opening for accepting a spinal implant therewithin such that the angle and length of the plate can be rigidly locked.

The present invention provides for a plate for attachment to spinal implants where the plate contains an opening to accept a spherical bearing or spinal implant with a spherical surface and an oblong opening for accepting a spinal implant therewithin and a section of the plate that can be contoured or bent to allow adjustment of the curvature of the plate.

The present invention provides for a plate construct for attachment to spinal implants, the plate construct containing an opening to accept a spherical bearing or spinal implant with a spherical surface and an oblong opening for accepting a slider and a spinal implant therewithin such that the angle and length of the plate can be rigidly locked.

The present invention provides for a plate construct for attachment to spinal implants, the plate construct connecting a first implant and a second implant, and an additional plate construct can be connected to the first or second spinal implant in the first construct and subsequently connected to a third implant to treat multiple level spine disorders.

The present invention provides for a plate construct for attachment to spinal implants, the plate construct connecting a first implant and a second implant, and an additional plate construct can be connected to the first or second spinal implant in the first construct and subsequently connected to a third implant to treat multiple level spine disorders, and additional plate constructs added as necessary to treat as many spinal levels as required.

The present invention provides for a plate construct for attachment to spinal implants, the plate construct connecting a short first implant and a taller second implant such that the second spinal implant is tall enough to accept an additional plate construct.

The present invention provides for a plate construct for attachment to spinal implants where multiple plate constructs can connect as many short implants and tall implants as needed to span the necessary levels in the spine.

The present invention provides for a plate construct for attachment to spinal implants where the spinal implants are attached to the pedicles first and the plate construct is placed over the spinal implants and secured to the spinal implants.

The present invention provides for a plate having a contourable section.

The present invention provides for a plate having a contourable section that is rectangular, square, round, half round, or any other geometric cross-section.

The present invention provides for combining the benefits of a plating system with the benefits of a rod system.

With the foregoing and other objects in view, there is provided, in accordance with the invention, a spinal fixation device includes at least one bone screw, at least one locking nut, a bearing, at least one slider, and an elongate plate construct. The bone screw has a head with a nut connection section and a screw portion shaped to screw into bone. The locking nut has an internal bore shaped to connect to the nut connection section of the at least one bone screw and an exterior wall. The bearing has an exterior and defining an internal bore shaped to fit therein the nut connection section of the head and the exterior wall of the at least one locking nut. The slider defines an internal bore shaped to fit the exterior wall of the at least one locking nut therewithin and has an exterior with a given shape. The elongate plate construct has a first end defining a first opening shaped to accept the exterior of the bearing therein and a second end defining a second opening shaped to accept the at least one slider therein and having a corresponding shape to the given shape to permit the at least one slider to slide in at least a portion of the second opening.

With the objects of the invention in view, there is also provided a bearing for a modular spinal fixation assembly having a plate construct, a bone screw with a nut connection section, and a locking nut with an exterior wall, the bearing comprising a spherical bearing body. The body defines an internal bore having an upper, outwardly chamfered surface, having an intermediate cylindrical surface, having a lower, outwardly chamfered surface, and shaped to fit therein the nut connection section of the bone screw and the exterior wall of the locking nut. The body has a circumference, an outer surface, a top face, a bottom face and at least one slot extending from each of the top and bottom faces towards the other one of the top and bottom faces and extending in depth from the internal bore to the outer surface. When connected to the plate construct between the bone screw and the locking nut, further clamping of the bone screw and the locking nut together expands the bearing evenly along the circumference.

With the objects of the invention in view, there is also provided a modular spinal fixation assembly includes at least two bone screws, at least two locking nuts, at least two bearings, at least one slider, first and second elongate plate constructs, and an elongate plate connector. A first of the bone screws has a head with a nut connection section with a cylindrical section and a screw portion shaped to screw into bone. A second of the bone screws has a head with a nut connection section with an extended cylindrical section and a screw portion shaped to screw into bone. The two locking nuts each has an internal bore shaped to connect to the nut connection section of each of the at least two bone screws and an exterior wall. The two bearings each have an exterior and define an internal bore shaped to fit therein the nut connection section of the head of the first and second bone screws and the exterior wall of each of the at least two locking nuts. The slider defines an internal bore shaped to fit the exterior wall of the at least one locking nut therewithin and has an exterior with a given shape. The first and second elongate plate constructs each have a first end defining a first opening shaped to accept the exterior of one of the at least two bearings therein and a second end defining a second opening shaped to accept the at least one slider therein and having a corresponding shape to the given shape to permit the at least one slider to slide in at least a portion of the second opening The elongate plate connector has a first end with a locking nut connection section shaped to connect to the internal bore of one of the locking nuts and has a second end defining a bore shaped to accept therein an exterior of the extended cylindrical section of the nut connection section of the second bone screw, and connects the first and second elongate plate constructs together with a first of the at least two locking nuts attached to the locking nut connection section and surrounded by a first of the at least two bearings within the first opening of the first end of the first elongate plate construct, and a second of the at least two locking nuts attached to the nut connection section of the second bone screw and surrounded by a second of the at least two bearings within the first opening of the first end of the second elongate plate construct, the extended cylindrical section of the second bone screw being disposed within the bore of the second end of the elongate plate connector.

When the bearing is placed within the first opening, and the head of the at least one bone screw is placed through the internal bore of the bearing, and the at least one locking nut is attached to the nut connection section to secure the bone screw head, the bearing, and the at least one locking nut therein, the bearing permits the bone screw head to move within the first opening relative to the elongate plate construct.

In accordance with another feature of the invention, when the head of the at least one bone screw is placed within the internal bore of the at least one slider, and the at least one slider is placed slidably in the second opening of the elongate plate construct, and the at least one locking nut is attached to the nut connection section through the internal bore, the at least one slider permits the bone screw to move and slide within the second opening relative to the elongate plate construct.

In accordance with a further feature of the invention, the nut connection section includes a threaded portion, a non-threaded portion next to the threaded portion opposite the screw portion, a cylindrical section, a recess between the cylindrical section and the threaded portion, and a tapered section between the cylindrical section and the screw portion.

In accordance with an added feature of the invention, the internal bore of the at least one locking nut releasably connects to the nut connection section of the at least one bone screw.

In accordance with an additional feature of the invention, the at least one locking nut has features shaped to connect to a tool that removably connects the at least one locking nut to the nut connection section of the at least one bone screw.

In accordance with yet another feature of the invention, the exterior of the bearing is spherical in shape and the internal bore of the bearing has an upper, outwardly chamfered surface, an intermediate cylindrical surface, and a lower, outwardly chamfered surface.

In accordance with yet a further feature of the invention, the exterior wall of the at least one locking nut has a given outer diameter, the at least one locking nut has interior threads shaped to mate with the exterior threads of the nut connection section, a head with a head diameter greater than the given outer diameter, a lower lip with a lip diameter greater than the given outer diameter, and a lower-facing, chamfered surface tapering from the head at the head diameter to the exterior wall at the given outer diameter, the exterior wall being disposed between the lower lip and the upper chamfered surface, and the nut connection section of the at least one bone screw has exterior threads and an expanded section between the exterior threads and the screw portion and wider in diameter than the exterior threads and the screw portion and having an upper chamfered surface tapering inwards and upwards from a larger outer diameter to a smaller inner diameter.

In accordance with yet an added feature of the invention, when the head of the at least one bone screw is placed through the internal bore of the bearing and the at least one locking nut is attached to the nut connection section to secure the bearing between the upper chamfered surface of the at least one bone screw and the lower-facing, chamfered surface of the at least one locking nut, the bearing expands at the upper, outwardly chamfered surface and the lower, outwardly chamfered surface circumferentially as the at least one locking nut is tightened onto the exterior threads.

In accordance with yet an additional feature of the invention, the bearing has a top face, a bottom face, and at least one slot extending from one of the top and bottom faces towards the other one of the top and bottom faces.

In accordance with again another feature of the invention, the at least one slot is at least one of at least one slot extending from each of the top and bottom faces and slots extending from each of the top and bottom faces.

In accordance with again a further feature of the invention, the internal bore of the bearing is shaped to fit therein both the nut connection section of the head and the exterior wall of the at least one locking nut.

In accordance with again an added feature of the invention, the slider is a slider assembly with a top sliding component having a bore shaped to accommodate therein the exterior wall of the at least one locking nut and being disposed on a side of the elongate plate construct opposite the screw portion of the at least one bone screw and a bottom sliding component having a bore shaped to accommodate therein the exterior wall of the at least one locking nut and being disposed on a side of the elongate plate construct opposite the top sliding component.

In accordance with again an additional feature of the invention, the slider assembly includes a top washer having a bore shaped to accommodate therein the exterior wall of the at least one locking nut and being disposed between the at least one locking nut and the top sliding component, when the head of the at least one bone screw is placed within the bore of the bottom sliding component, the bore of the top sliding component, and the bore of the top washer, and the at least one locking nut is partially tightened to the nut connection section, the top washer and the top sliding component permit the bone screw to move and slide within the second opening relative to the elongate plate construct, and when the head of the at least one bone screw is placed within the bore of the bottom sliding component, the bore of the top sliding component, and the bore of the top washer, and the at least one locking nut is fully tightened to the nut connection section, the top washer and the top sliding component prevent the bone screw from moving or sliding within the second opening relative to the elongate plate construct.

In accordance with still another feature of the invention, the first opening is shaped to accept the bone screw head, the bearing, and the at least one locking nut therein and the second opening is shaped to accept the bone screw head, the bearing, and the at least one slider therein.

In accordance with still a further feature of the invention, the first opening is shaped to allow pitch, roll, and yaw movement of the bearing therein.

In accordance with still an added feature of the invention, when the bearing is placed within the first opening, and the head of the at least one bone screw is placed through the internal bore of the bearing, and the at least one locking nut is removably attached to the nut connection section to secure the bone screw head, the bearing, and the at least one locking nut therein, the bearing permits the bone screw head to at least partially roll, pitch, and yaw within the first opening relative to the elongate plate construct.

In accordance with still an additional feature of the invention, when the head of the at least one bone screw is placed within the internal bore of the at least one slider, and the at least one slider is placed slidably in the second opening of the elongate plate construct, and the at least one locking nut is removably attached to the nut connection section through the internal bore, the at least one slider permits the bone screw to rock and slide within the second opening relative to the elongate plate construct.

In accordance with another feature of the invention, the elongate plate construct has a rod portion connecting the first end to the second end.

In accordance with a further feature of the invention, the first end is plate shaped and the second end is plate shaped.

In accordance with an added feature of the invention, the bearing is two bearings, both having a given longitudinal length through the bore, the elongate plate construct is at least first and second elongate plate constructs, at least one locking nut has internal threads and connects the first and second elongate plate constructs together at the respective first ends by placing the two bearings one on top of the other on the nut connection section and tightening the internal threads of the extended locking nut onto the threaded portion of the at least one bone screw, and an overall length of at least one of the nut connection section of the at least one bone screw and the at least one locking nut is at least twice as long as the given longitudinal length.

In accordance with an additional feature of the invention, the at least one bone screw is at least two bone screws, a first of the at least two bone screws having the nut connection section with a cylindrical section and the second of the at least two bone screws having the nut connection section with an extended cylindrical section, the at least one locking nut is at least two locking nuts, the bearing is at least two bearings, the elongate plate construct is at least first and second elongate plate constructs, and further comprising an elongate plate connector having a first end with a locking nut connection section shaped to connect to the internal bore of one of the locking nuts, having a second end defining a bore shaped to accept therein an exterior of the extended cylindrical section of the nut connection section of the second bone screw, and connecting the first and second elongate plate constructs together with a first of the at least two locking nuts attached to the locking nut connection section and surrounded by a first of the at least two bearings within the first opening of the first end of the first elongate plate construct, and a second of the at least two locking nuts attached to the nut connection section of the second bone screw and surrounded by a second of the at least two bearings within the first opening of the first end of the second elongate plate construct, the extended cylindrical section of the second bone screw being disposed within the bore of the second end of the elongate plate connector.

In accordance with yet another feature of the invention, when the exterior of the extended cylindrical section of the nut connection section of the second bone screw is place through the bore of the second end of the elongate plate connector, and the head of the second bone screw is placed through the internal bore of one of the bearings, and the one of the bearings and the head of the second bone screw are placed within the first opening of the first plate construct, and one of the locking nuts is attached to the locking nut connection section to secure the head of the second bone screw, the one of the bearings, and the one locking nut therein, the one bearing permits the bone screw head to move within the first opening relative to the first plate construct.

In accordance with yet a further feature of the invention, when the head of the first bone screw is placed within the internal bore of the at least one slider, and the at least one slider is placed slidably in the second opening of one of the first and second elongate plate constructs, and one of the locking nuts is attached to the nut connection section of the first bone screw through the internal bore of the at least one slider, the at least one slider permits the bone screw to move and slide within the second opening relative to the one of the first and second plate constructs.

In accordance with yet an added feature of the invention, the plate connector removably connects the first and second elongate plate constructs together.

In accordance with yet an additional feature of the invention, the extended cylindrical section of the second bone screw is rotatably disposed within the bore of the second end of the elongate plate connector.

In accordance with again another feature of the invention, the first opening is shaped to accept the bone screw head, the bearing, and the at least one locking nut therein and the second opening is shaped to accept the bone screw head, the bearing, and the at least one slider therein.

In accordance with a concomitant feature of the invention, the first opening is shaped to allow pitch, roll, and yaw movement of the bearing therein.

With the foregoing and other objects in view, there is provided, in accordance with the invention, an orthopedic fixation device comprising a bearing and a retaining portion. The bearing defines a bearing internal bore and has a rounded exterior surface, an upper surface, an intermediate surface, and a lower surface, and at least one slot in the bearing extending from the exterior surface to the internal bore. The retaining portion defines a recess shaped to accept the exterior surface of the bearing therein such that in a steady state of the bearing, the bearing can move within the recess, and, when at least one force is imparted against one of the upper and lower surfaces of the bearing, the bearing deforms outwardly to fix the bearing in place within the recess.

In accordance with another feature, the bearing has a spherically shaped exterior in the steady state and the exterior of the bearing deforms from spherical to removably fix the bearing in place within the recess.

In accordance with a further feature, the bearing has an ovoid shaped exterior in the steady state and the exterior of the bearing deforms from ovoid to removably fix the bearing in place within the recess.

In accordance with an added feature, the upper surface of the bearing internal bore is an upper, outwardly chamfered surface and the lower surface of the bearing internal bore is a lower, outwardly chamfered surface.

In accordance with an additional feature, the upper surface of the bearing internal bore is an arcuate surface and the lower surface of the bearing internal bore is an arcuate surface.

In accordance with yet another feature, the at least one force is forces imparted against the upper and lower surfaces of the bearing, and, when the forces are imparted against the upper surface and the lower surface of the bearing, the bearing deforms outwardly to fix the bearing in place within the recess.

In accordance with yet a further feature, the at least one slot in the bearing is at least one slot that extends from the upper surface to the lower surface.

In accordance with yet an added feature, the at least one slot in the bearing is at least one first blind slot having an open end at the upper surface, a blind end adjacent the lower surface, and extending from the open end at the upper surface to the blind end and at least one second blind slot having an open end at the lower surface, a blind end adjacent the upper surface, and extending from the open end at the lower surface to the blind end.

In accordance with yet an additional feature, the at least one slot in the bearing is one slot that extends from the upper surface to the lower surface and at least one first blind slot extending from at least one of the upper surface and the lower surface.

In accordance with again another feature, the recess is shaped to allow pitch, roll, and yaw movement of the bearing therein.

In accordance with again a further feature, the bearing internal bore is shaped to fit therein a portion of a fastener comprising at least one bone screw having a screw portion shaped to screw into bone and a head with a nut connection section having exterior threads, and an expanded section between the exterior threads and the screw portion and wider in diameter than the exterior threads and the screw portion and having an upper chamfered surface tapering inwards and away from the screw portion from a larger outer diameter to a smaller inner diameter to correspond in shape with the lower surface of the bearing internal bore. At least one locking nut has a nut internal bore with interior threads shaped to mate with the exterior threads of the nut connection section to connect the at least one locking nut to the at least one bone screw, an exterior wall having a given outer diameter to fit within intermediate surface of the bearing internal bore, a head having a head outer diameter greater than the given outer diameter, a lower lip having a lip outer diameter greater than the given outer diameter, and a lower-facing, chamfered surface tapering from the head at the head diameter to the exterior wall at the given outer diameter to correspond in shape with the upper surface of the bearing internal bore, the exterior wall being disposed between the lower lip and the upper chamfered surface.

In accordance with again an added feature, the at least one locking nut is a locking nut assembly having a locking nut having the nut internal bore, the exterior wall, the head, and the lower lip and a collar having the lower-facing, chamfered surface and being a separate component from the locking nut and configured to rotate about the exterior wall.

In accordance with again an additional feature, the bearing internal bore is shaped to fit therein a portion of a fastener comprising at least one bone screw and at least one locking nut. The at least one bone screw has a screw portion shaped to screw into bone and a head with a nut connection section having exterior threads and an expanded section between the exterior threads and the screw portion and wider in diameter than the exterior threads and the screw portion and having an upper surface directed inwards and away from the screw portion from a larger outer diameter to a smaller inner diameter to correspond in shape with the lower surface of the bearing internal bore. The at least one locking nut has a nut internal bore with interior threads shaped to mate with the exterior threads of the nut connection section to connect the at least one locking nut to the at least one bone screw, an exterior wall having a given outer diameter to fit within intermediate surface of the bearing internal bore, a head having a head outer diameter greater than the given outer diameter, a lower lip having a lip outer diameter greater than the given outer diameter, and a lower-facing surface directed from the head at the head diameter to the exterior wall at the given outer diameter to correspond in shape with the upper surface of the bearing internal bore, the exterior wall being disposed between the lower lip and the upper chamfered surface and, when the head of the at least one bone screw is placed through the bearing internal bore and the at least one locking nut is attached to the nut connection section to secure the bearing between the upper surface of the at least one bone screw and the lower-facing surface of the at least one locking nut, the bearing expands at the upper surface and the lower surface circumferentially as the at least one locking nut is tightened onto the exterior threads.

In accordance with still another feature, when the bearing is placed within the recess, and the head of the at least one bone screw is placed through the bearing internal bore, and the at least one locking nut is removably attached to the nut connection section to secure the bone screw head, the bearing, and the at least one locking nut therein, the bearing permits the bone screw head to at least partially roll, pitch, and yaw within the recess relative to the retaining portion.

In accordance with still a further feature, the portion of the fastener that the bearing internal bore is shaped to fit is a nut connection section of a head of a screw.

In accordance with still an added feature, the exterior wall and the lower lip of the at least one locking nut are shaped to removably retain the at least one locking nut within a portion of the bearing internal bore.

In accordance with still an additional feature, the at least one first blind slot is a plurality of first blind slots and the at least one second blind slot is a plurality of second blind slots.

In accordance with again an added feature, at least some of the plurality of first blind slots are symmetrically disposed about the bearing internal bore.

In accordance with again an additional feature, at least some of the plurality of second blind slots are non-symmetrically disposed about the bearing internal bore.

In accordance with still another feature, the plurality of second blind slots are disposed about the bearing internal bore offset from the plurality of first blind slots.

In accordance with still a further feature, the recess is shaped to accept the bone screw head, the bearing, and the at least one locking nut therein.

In accordance with still an added feature, wherein the at least one locking nut has features shaped to connect to a tool that removably connects the at least one locking nut to the nut connection section of the at least one bone screw.

With the objects in view, there is also provided a an orthopedic fixation device, comprising a bearing and a retaining portion. The bearing defining a bearing internal bore and having a rounded exterior surface, an upper surface, an intermediate surface, and a lower surface, and at least one slot in the bearing extending from the exterior surface to the internal bore. The retaining portion has a recess, an upper edge, and a lower edge and is shaped to accept the bearing therein such that, in a steady state of the bearing, the bearing can move within the recess, and, when at least one force is imparted against one of the upper and lower surfaces of the bearing, the bearing deforms outwardly to engage the upper and lower edges and fix the bearing in place in the recess.

Although the invention is illustrated and described herein as embodied in a polyaxial plate rod system and surgical procedures for insertion of the polyaxial plate rod system, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Additional advantages and other features characteristic of the present invention will be set forth in the detailed description that follows and may be apparent from the detailed description or may be learned by practice of exemplary embodiments of the invention. Still other advantages of the invention may be realized by any of the instrumentalities, methods, or combinations particularly pointed out in the claims.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the present invention. Advantages of embodiments of the present invention will be apparent from the following detailed description of the exemplary embodiments thereof, which description should be considered in conjunction with the accompanying drawings in which:

FIG. 2 is a perspective view of an exemplary embodiment of a bone screw of the plate assembly of FIG. 1;

FIG. 3 is an exploded perspective view of an exemplary embodiment of a polyaxial body of the plate assembly of FIG. 1 aligned with a bone screw head;

FIG. 54 is an exploded view of an exemplary embodiment of a plate-rod construct assembly;

FIG. 55 is an exploded perspective view of an exemplary embodiment of a slider assembly;

FIG. 56 is an exploded side elevational view of the slider top and bottom washers;

FIG. 62 is a perspective view of the upper sliding component of the assembly of FIG. 58;

FIG. 63 is a side elevational view of the upper sliding component of the assembly of FIG. 58;

FIG. 64 is a perspective view of an exemplary embodiment of a washer of the assembly of FIG. 59;

FIG. 67 is an enlarged view of a bone screw with an arcuate bone screw face.

FIG. 68 is a fragmentary, cross-sectional view of the slider assembly of FIG. 65 with the arcuate face bone screw of FIG. 67;

FIG. 68A is a cross-sectional view of an exemplary embodiment of a slider assembly;

FIG. 74 is a fragmentary, exploded, perspective view of another exemplary embodiment of a slider assembly that allows rotation;

FIG. 75 is a perspective view of a top washer of the assembly of FIG. 74;

FIG. 76 is a perspective view of a pivot sliding component of the assembly of FIG. 74;

FIG. 77 is a fragmentary, perspective view of the plate or rod end of the assembly of FIG. 74;

FIG. 78 is a perspective view of a lower bearing or pivot of the assembly of FIG. 74;

DETAILED DESCRIPTION OF THE INVENTION

Figure 1:
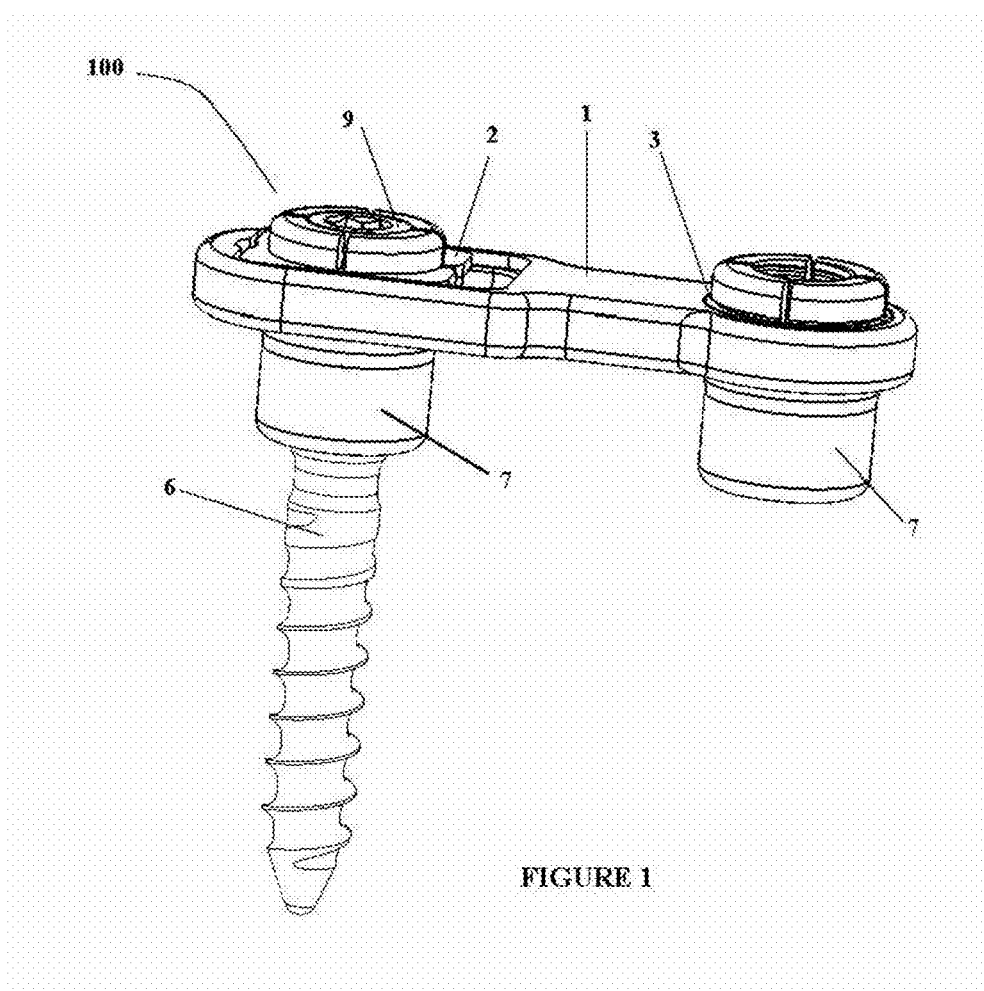
FIG. 1 is a perspective view of an exemplary embodiment of a plate assembly with polyaxial screws.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

Herein various embodiments of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Described now are exemplary embodiments of the present invention. Referring now to the figures of the drawings in detail, there is shown a first exemplary embodiment of a new implant assembly illustrated generally at 100 in FIGS. 1 through 10, that, by its novel construction, permits the implant 100 to attach to bone screws while compensating for anatomic considerations and breaking down complex multilevel surgical procedures into simpler single level procedures.

Plate 1 is substantially rectangular in shape. Of course, the plate 1 does not need to be rectangular, but can also be other shapes. Plate 1, as well as the other components of the implant can be made of various materials, such as, but not limited to, metals, such as titanium, or stainless steels, polymers, or a combination of both.

The assembly 100 has various features as shown in FIG. 1. These features include the plate 1, a slider component 2, a spherical or partially spherical bearing 3 (see, e.g., FIGS. 18 and 19), a bone screw 6 for engagement with a bone, a polyaxial screw body 7, and a set screw 9.

FIG. 2 details a version of the bone screw 6. The bone screw 6 has a threaded portion 6a having a tip 6b, a spherical head 6c, a top of the spherical section 6d, a driving feature 6e for turning and advancing or removing the screw from the bone, a neck portion 6f between the spherical head 6c and threads 6a, and blend radii 6g to blend the neck 6f into the spherical head 6c to avoid any sharp transitions. The bone screw 6 is designed to engage bone, and, in the lumbar spine, a wall of the pedicles. The thread 6a can be any appropriate thread to engage bone, and the minor diameter can be straight or tapered. Also, the spherical head 6c can be textured or smooth. While the screw driving feature 6e is shown as a hex for an Allen key type driver, this feature can be one of many different kinds, including a square drive, a star drive, torx, and others.

FIG. 3 shows the bone screw 6 and head 6c as well as a polyaxial screw body 7 and set screw 9. In this exemplary embodiment, the polyaxial screw body 7 can be securely attached to the bone screw head 6c, details of which follow in the figures. The polyaxial screw body 7 includes a top 7a and a bottom surface 7b. The polyaxial screw body 7 has a recessed portion 7c, at least one slot 7d through a wall of the polyaxial screw body 7, a blend radius 7e to avoid any sharp edges that might impinge soft tissue, and a blend radius 7f to avoid impingement with soft tissue and bone. The recess 7c creates an upper surface 7j and a lower surface 7h. In this example, the polyaxial screw body 7 is generally cylindrical and has a lower diameter 7k. To create a larger lower and/or upper lip, the body diameter can be increased above the lower diameter 7k, allowing a larger diameter lip 7m without increasing the depth of the recess 7c. When this extended lip 7m is presented, it is preferable to have a blend radius 7g to avoid any stress risers. The polyaxial body 7 can be cylindrical without the changes in diameter; however, in general, having the smallest possible diameter where the lower portion of the body will potentially contact bone is a benefit.

Figure 4:
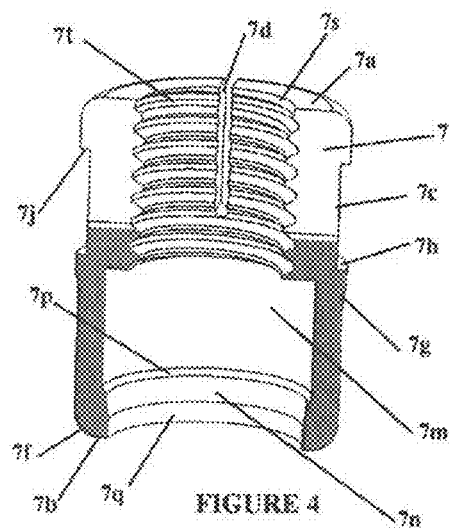
FIG. 4 is a cross-sectional view of the polyaxial body of the plate assembly of FIG. 1.

FIG. 4 details the inside of a polyaxial screw body 7. The section view shows the polyaxial screw body 7 having the top 7a and a threaded section 7t extending downward towards the lower surface 7b and extending into a recess or pocket 7m. The recess or pocket 7m transitions to a smaller diameter by an inwardly directed chamfer 7p, and a longer chamfer or taper 7n, which then transitions to opening 7q in the polyaxial screw body 7. The screw thread in this example has a chamfer or taper 7s at the top of thread 7k. The thread 7k can be cut into the chamfer or taper 7s, as shown, or the chamfer or taper 7s can be partially cut into or large enough where the threads do not cut into the taper or chamfer 7s feature. To allow the polyaxial screw body 7 to be flexible, at least one slot 7d is cut into the polyaxial screw body 7. The depth of slot 7d can be varied according to requirements. If there are multiple slots 7d, the depths of the slots 7d can also vary to better distribute stresses and/or vary flexibility of the polyaxial screw body 7.

Figure 5:
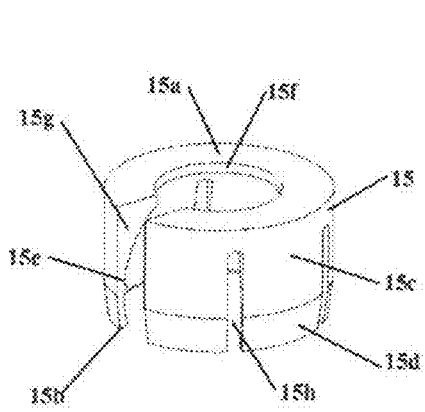
FIG. 5 is a perspective view of the polyaxial insert of the plate assembly of FIG. 1 from a side thereof.
Figure 6:
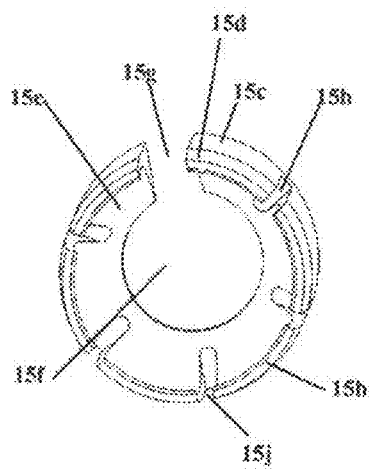
FIG. 6 is a perspective view of the polyaxial insert of the plate assembly of FIG. 1 from a bottom thereof.

FIGS. 5 and 6 show a polyaxial insert 15 having a top surface 15a and a bottom surface 15b, an external wall 15c generally cylindrical in shape, a chamfered or tapered portion 15d, a spherical or partially spherical internal feature 15e, an opening 15f extending into the spherical feature 15e, a slot 15g in the wall 15c to provide flexibility to the polyaxial screw insert 15 so that the insert 15 can be compressed to fit within the polyaxial screw body 7, and additional slots 15h to provide further flexibility. Slots 15h are optional, as are the quantity used, and the height of the slots 15h can vary. The slot 15j opposite the main slot 15g can partially penetrate the top surface 15a of the polyaxial insert 15 or the top surface 15a of the insert 15 can be formed or machined such that the wall thickness of the insert 15 is thinner in the location of slot 15j to allow the polyaxial insert 15 to flex more easily for insertion into the polyaxial screw body 7.

Figure 7:
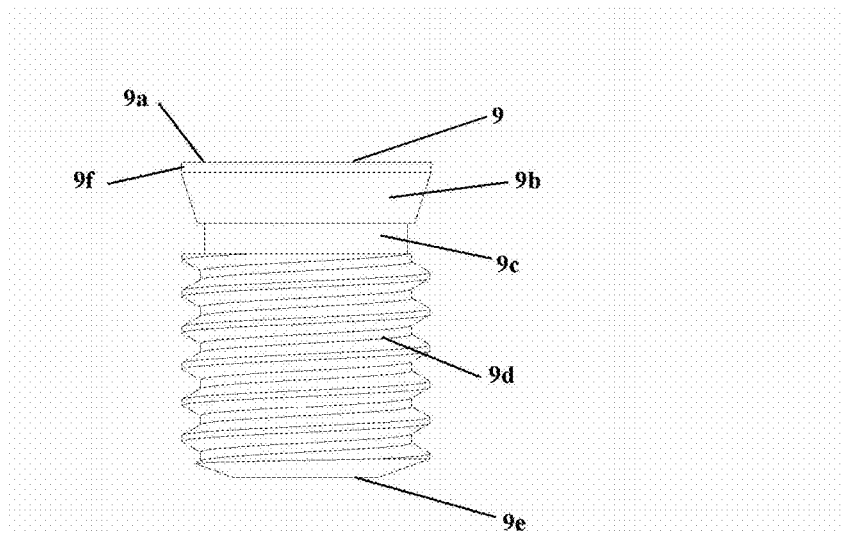
FIG. 7 is a side elevational view of an exemplary embodiment of a set screw of the plate assembly of FIG. 1.
Figure 8:
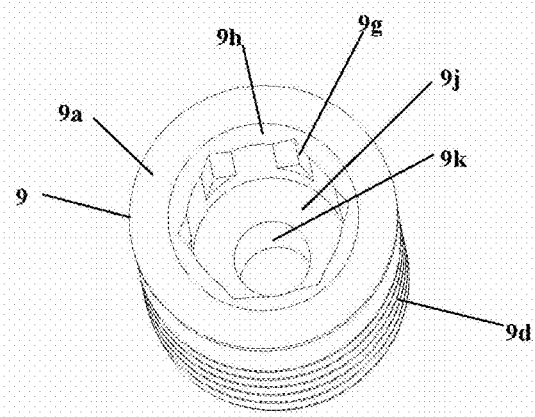
FIG. 8 is a perspective view of the set screw of FIG. 7 from above.

FIGS. 7 and 8 show a variation of the set screw 9 having a top 9a, a tip 9e, a tapered portion 9b, a neck 9c, a threaded section 9d, and a small lip 9f, which helps avoid a sharp edge where the taper 9b meets the top 9a. A hex drive or Allen key type drive 9g is provided Shown in FIG. 8 for turning the set screw 9. However, this feature can be of any variety used to turn a screw, such as square drive, a star drive, torx, or any other. A chamfer 9h avoids sharp edges at the top 9a where the driving feature intersects and provides easier attachment to an instrument. The set screw 9 can be machined with the driving feature 9g cut to a specific depth, leaving a lower face 9j in set screw 9. Also, a hole 9k can be machined or drilled into set screw 9 to allow a K-wire to pass therethrough. In addition, the driving feature 9g can be cut completely through set screw 9 so that no lower face 9j remains. Furthermore, the set screw 9 can be formed without a chamfer 9b for certain embodiments.

Figures 9, 10:
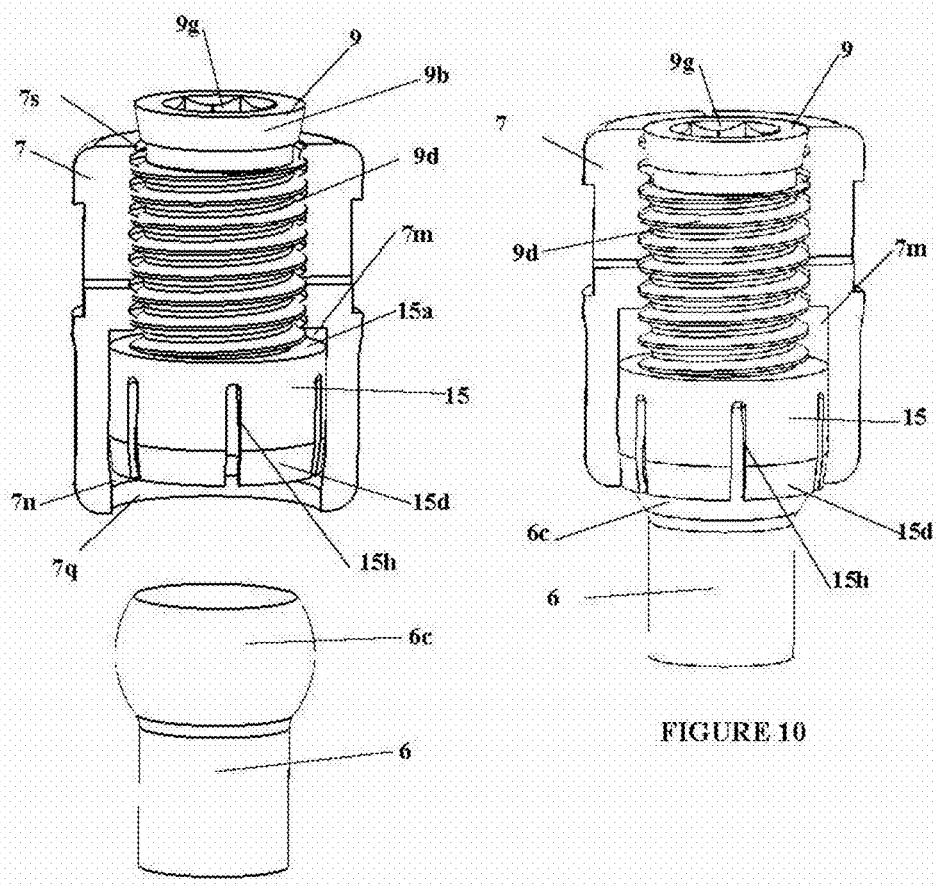
FIG. 9 is a partially cross-sectional, perspective view of an exemplary embodiment of a polyaxial assembly of the plate assembly of FIG. 1 in an unlocked position.
FIG. 10 is partially cross-sectional, perspective view of the polyaxial assembly of the plate assembly of FIG. 1 in a locked position.

FIG. 9 shows a cross-sectional view of a polyaxial screw assembly in an unlocked condition. The polyaxial screw body 7 contains the insert 15 and the set screw 9. The tapered portion of the set screw 9 is outside the polyaxial screw body 7 and the polyaxial insert 15 is not compressed against the taper 7n in the body 7, but is contained within the pocket or recess 7m in the polyaxial body 7. In this position, the polyaxial insert 15 is able to expand to accept the bone screw head 6c, such that the head 6c will fit and be contained within the spherical seat 15e in the polyaxial insert 15. Once the bone screw head 6c is contained within the polyaxial insert 15, the assembly is still free at this point to rotate around the bone screw head 6c.

FIG. 10 shows a cross-sectional view of the polyaxial screw assembly in a locked condition. The set screw 9 is advanced such that the tip 9e of the set screw 9 contacts the polyaxial insert 15 and forces it downward while the taper 9b engages the taper or chamfer 7s in the polyaxial screw body 7. This contact forces the polyaxial insert 15 to be compressed around the screw head 6c by engagement of the tapers or chamfers while forcing the upper section of body 7 to at least partially splay outward. While shown with the set screw 9 having taper 9b, a non-tapered set screw can also be used, as sufficient force against insert 15 will cause the threads 9d to exert an outward force against the polyaxial screw body threads 7t. As screw threads create force vectors, a portion of the force is directed outward, which can also cause the polyaxial screw body 7 to flex outward in the desired region. Of course, set screw 9 does not have to be fully threaded, but can have a longer neck 9c or a longer unthreaded tip 9e.

Figures 11, 12:
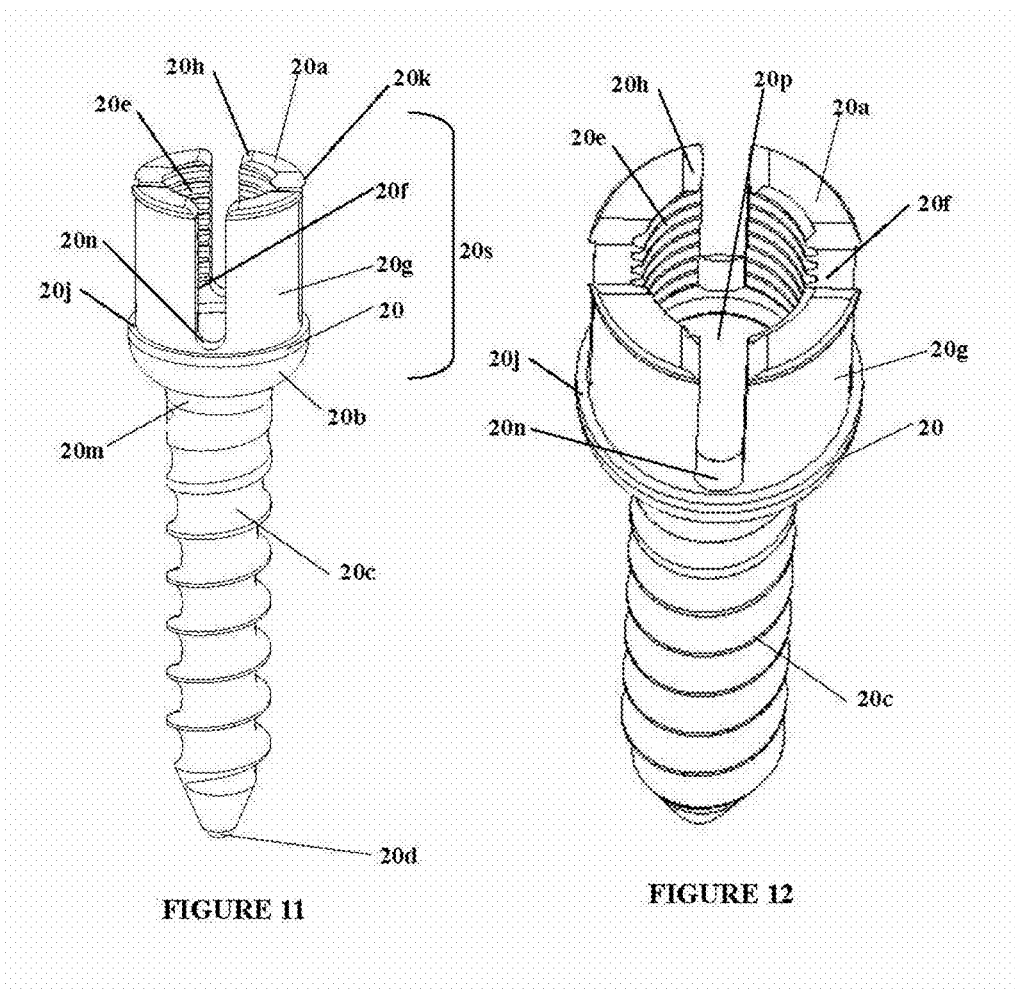
FIG. 11 is a perspective view of an exemplary embodiment of a monoaxial or fixed screw.
FIG. 12 is a perspective view of the monoaxial or fixed screw of FIG. 11 from above.

FIGS. 11 and 12 show a variation of a bone screw whereby the head 20s of the screw 20 is one piece or integral with the bone threads and shank. The monoaxial screw 20 includes the head 20s having a top 20a and a lower section 20b transitioning into the bone screw thread 20c. Preferably, this is machined as a single piece, but it could be assembled from two components. The monoaxial screw 20 has a tip 20d. The head portion 20s has an internal thread 20e extending downward from the face of the top 20a, at least one slot 20f, a recess 20g, a chamfer 20h at the top of the slot or slots 20f, and an upper lip 20k and lower lip 20j created by the recess 20g. The slots 20f preferably end in a radius 20n to avoid any stress risers. The depth of hole having the thread 20e is restricted to the larger diameter of head portion 20s, and creates a bottom surface 20p that may be flat, drill point shaped, rounded, or another shape as required. In addition, a non-illustrated hole for a k-wire can be provided that runs through the center of the monoaxial screw 20.

Figure 13:
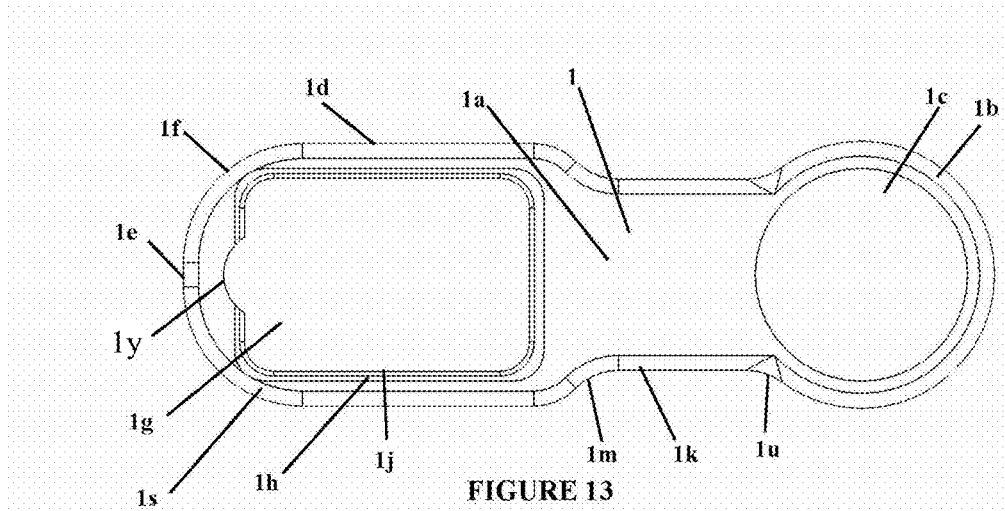
FIG. 13 is a top plan view of an exemplary embodiment of a plate of the plate assembly of FIG. 1.
Figure 14:
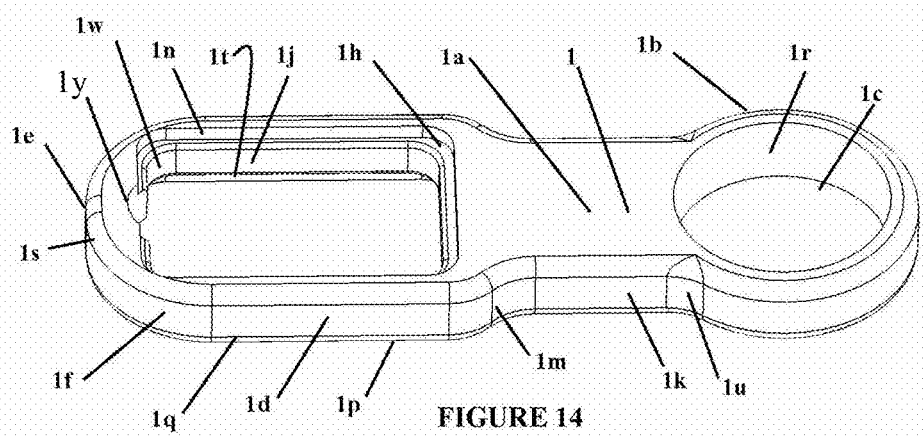
FIG. 14 is a perspective view of the plate of FIG. 13 from above.

FIGS. 13 and 14 show the plate 1 in greater detail. Plate 1 has a top surface 1a, a first end 1b defining an opening 1c, a rectangular section 1d having an end 1e and an edge radius 1f, and a rectangular opening 1g. In this preferred example, the first end 1b is generally round and transitions to the rectangular section 1d via a smaller middle section 1k. To avoid any sharp areas or stress risers, blend radius 1u transitions the round end 1b into the smaller rectangular section 1k, and radius 1m transitions the smaller middle section 1k to the larger rectangular section 1d. While the plate 1 can be machined as a uniform rectangle, by having a smaller section 1k, the plate can be more easily contoured or bent to match patient anatomy when needed. The rectangular opening 1g includes a recessed pocket with a surface 1h recessed into top surface 1a, which creates a small side wall 1n. A smaller rectangular opening is machined through the plate 1, which creates an inwardly directed lip 1j. The bottom of the plate has a recessed pocket 1t larger than the smaller rectangular opening. The edges of lip 1j transition by blend radii 1w, and the edges of the plate 1 have an upper blend radius 1s and a lower radius 1q to avoid any sharp edges that might cause tissue impingement. In this exemplary embodiment, the opening 1c is generally round and has a spherically shaped wall 1r. It is also possible to construct the wall 1r by the use of two inwardly directed opposed chamfers. At least one opening 1y, provides a location for an instrument to fit therein.

Figure 15:
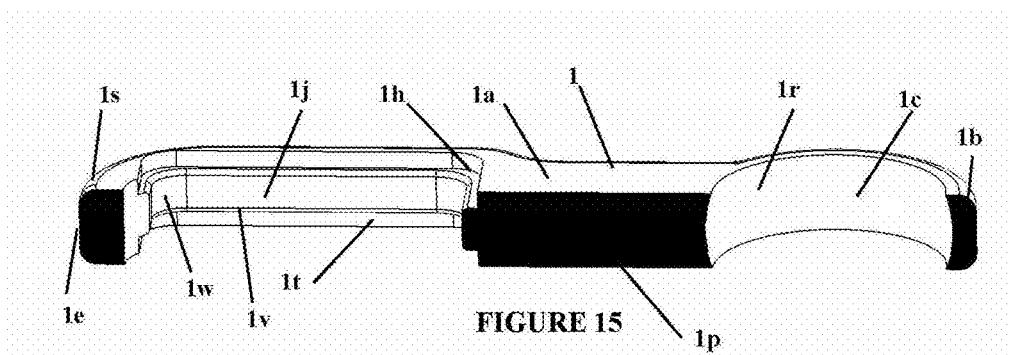
FIG. 15 is a cross-sectional view of the plate of FIG. 13.

FIG. 15 is a cross-sectional view that better shows the recessed feature. By cutting a pocket in the top 1a of plate 1 and a pocket in the bottom 1p of the plate 1 and cutting a smaller rectangle through both pockets, the machining leaves a ledge 1h that runs around the top of the pocket and a ledge 1v that runs around the bottom of the pocket. This allows a sliding component 2 to fit within the pocket to have the top 2a of the slider 2 be flush with the top 1a of plate 1 and the bottom 2b of the slider 2 be flush with the bottom 1p of plate 1. The spherical shape of wall 1r is also shown much clearer in this sectional view.

Figure 16:
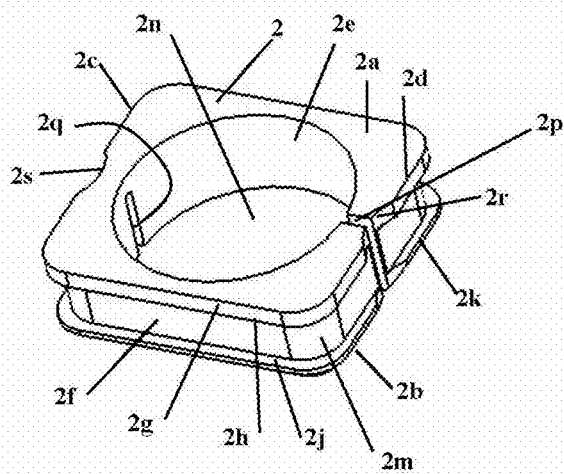
FIG. 16 is a perspective view of an exemplary embodiment of a slider of the plate assembly of FIG. 1.
Figure 17:
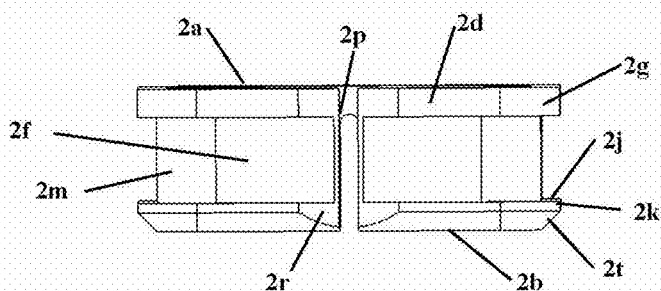
FIG. 17 is a side elevational view of the slider of FIG. 16.

FIGS. 16 and 17 show a variation of the slider 2 configured to fit into the recessed plate 1. This exemplary slider 2 has a top surface 2a and a lower surface 2b, a back edge 2c and a front edge 2d, a hole 2n through the slider 2 creates a side wall 2e, a recess 2f machined into the side of the slider 2 creates an upper lip 2g and face 2h, a lower lip 2j and face 2k, blend radii 2m at the corners of the recess, a slot 2p that cuts through the front edge 2d and extends into hole 2n, an optional additional slot 2q that partially extends into the slider 2 to increase slider flexibility, a small pocket 2r cut into front edge 2d, and a small pocket 2s cut into the rear edge 2c, and a chamfer 2t to make it easier to insert slider 2 into plate 1.

Figures 18, 19:
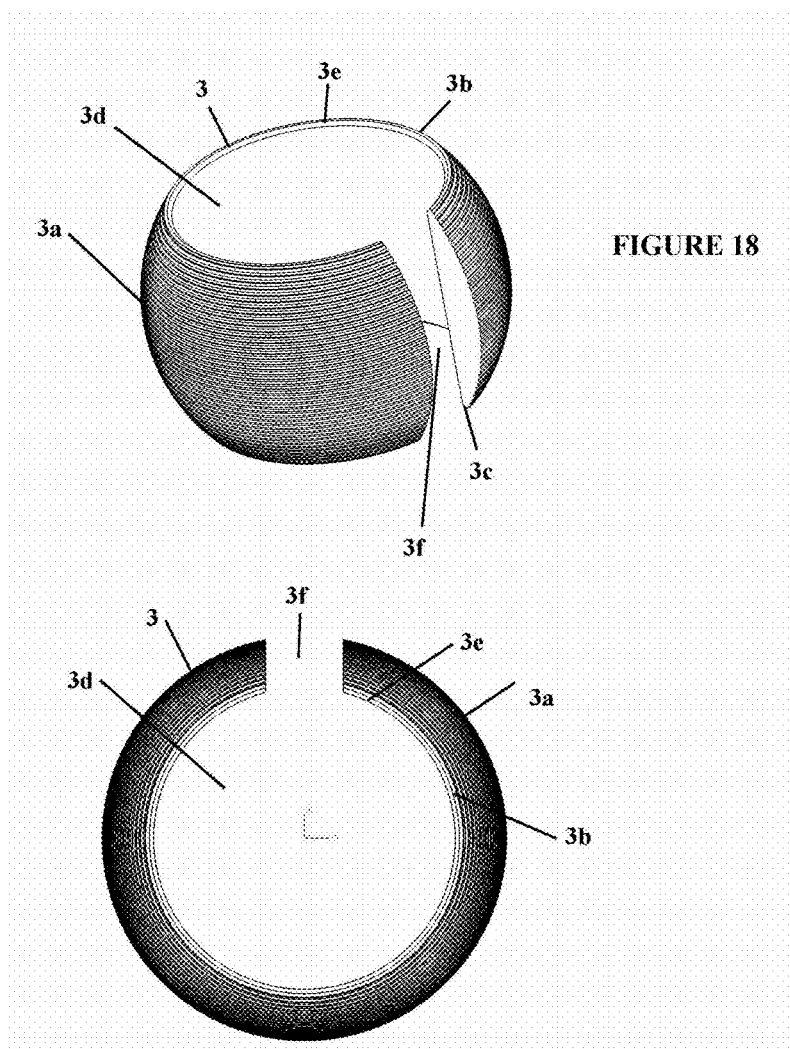
FIG. 18 is a perspective view of an exemplary embodiment of a spherical bearing for the plate assembly of FIG. 21.
FIG. 19 is a top plan view of the spherical bearing of FIG. 18.

FIGS. 18 and 19 show a variation of a spherical bearing 3 having an external spherical surface 3a that is either smooth or, as shown here, textured, a top edge 3b, a bottom edge 3c, a central hole 3d, a chamfer 3e, and a slot 3f which allows the spherical bearing to expand and contract.

Figure 20:
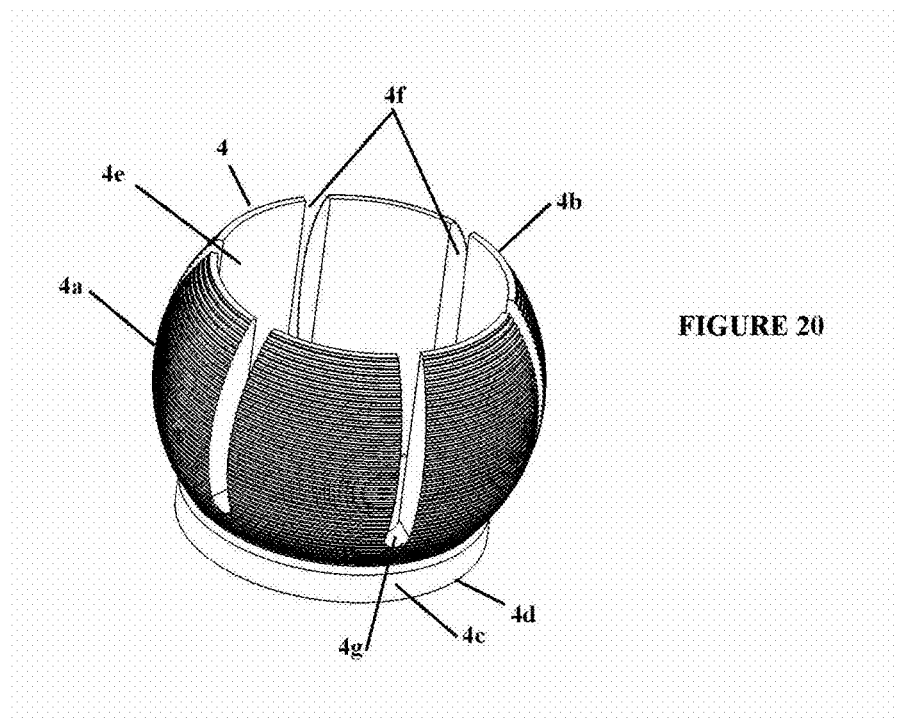
FIG. 20 is a perspective view of another exemplary embodiment of a spherical bearing for the plate assembly of FIG. 21.

FIG. 20 shows another variation of the spherical bearing whereby the bearing 4 has a spherical external surface 4a, a top surface 4b, a cylindrical section 4c, a lower edge 4d, an internal bore 4e, and multiple slots 4f that cut part way through the bearing such that the bearing is flexible but not split as in bearing 3. The slots preferably end in radii 4g to avoid stress risers, and the heights of the slots 4f can vary independently.

Figure 21:
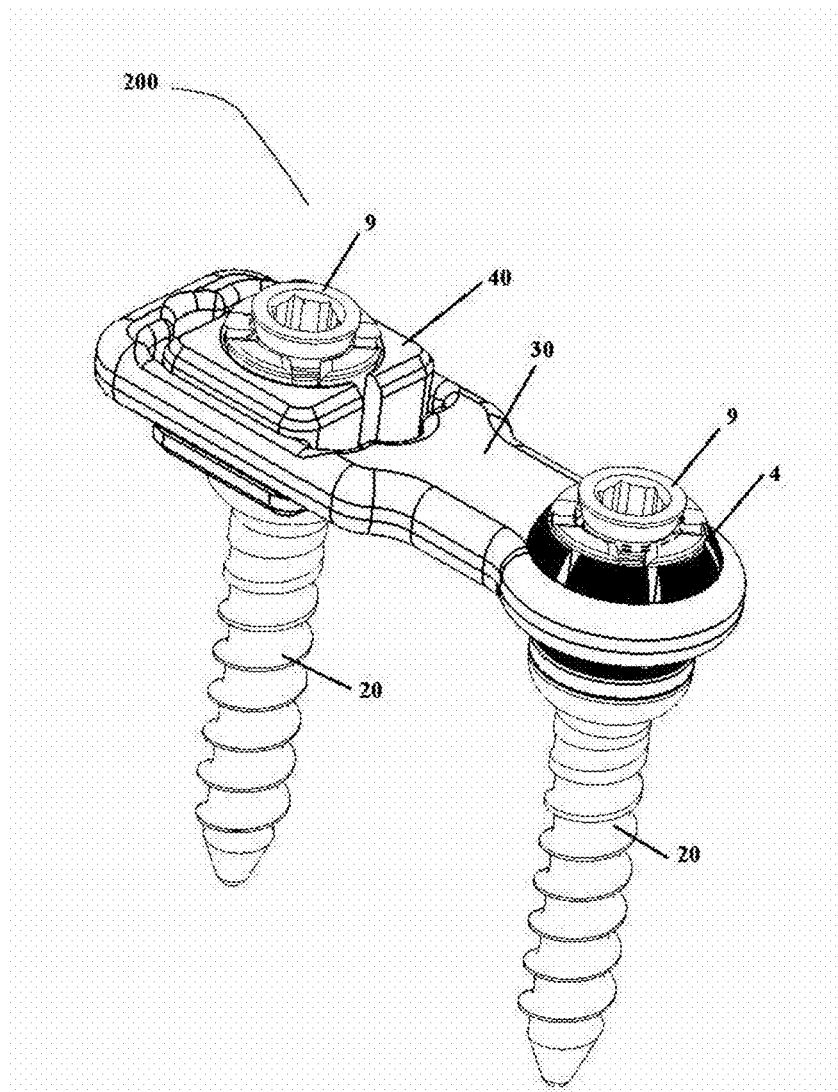
FIG. 21 is a perspective view of another exemplary embodiment of a plate assembly.

FIG. 21 shows another variation of a plate assembly, generally shown as 200. In this example, monoaxial screws 20 are used as the bone anchors. Plate 30 has a spherical opening to accept a spherical bearing, shown in this case as bearing 4, although alternatives, such as bearing 3 are acceptable, and an opening to accept an alternative slider 40. When the set screws 9 are tightened, the head of the first monoaxial screw 20 is forced outward, locking the monoaxial screw 20 to slider 40 and slider 40 to plate 30, and the second monoaxial screw 20 locks to the spherical bearing 4 and the bearing 4 to plate 30, thus locking the assembly in the desired orientation.

Figure 22:
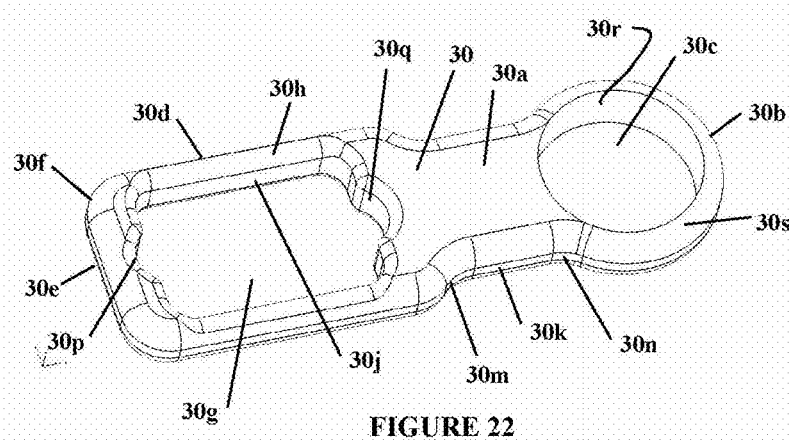
FIG. 22 is a perspective view of an exemplary embodiment of a plate of the plate assembly of FIG. 21.
Figure 23:
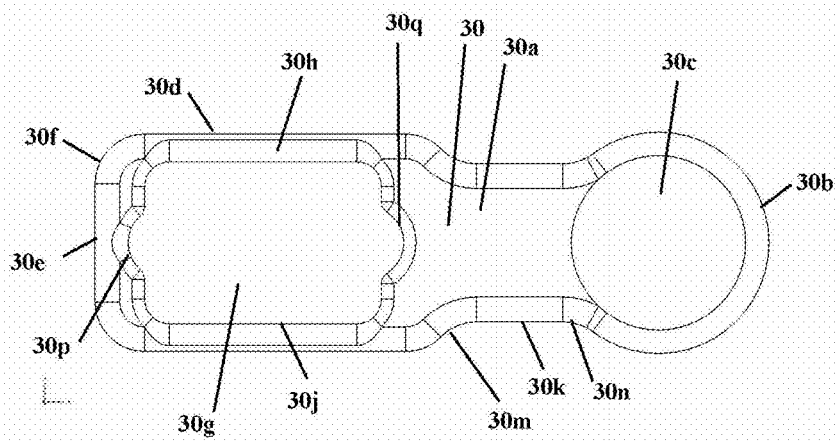
FIG. 23 is a top plan view of the plate of FIG. 22.

FIGS. 22 and 23 show an alternative plate 30 having a top surface 30a, a front section with a front round edge 30b and a central hole 30c with an interior surface 30r, and a rectangular section 30d with a back edge 30e, corner radii 30f and a rectangular opening 30g. The rectangular opening 30g has an upper blend radius 30h and a lower blend radii, and a side wall 30j. A smaller rectangular section 30k is present to allow for a more bendable or contourable zone that is transitioned into the front round section by radii 30n and to the rectangular section by radii 30m. Two openings in the plate: 30p in the back and 30q in the front of the rectangular opening 30g allow for instrument access.

Figure 24:
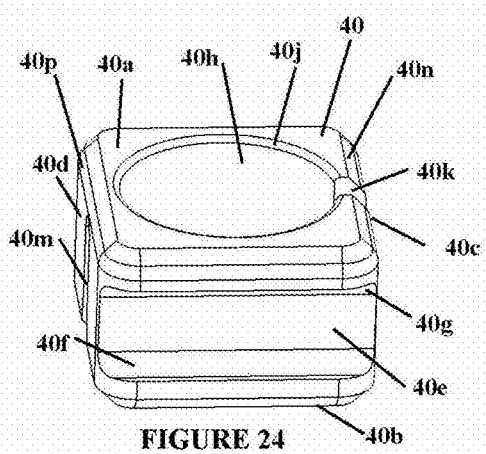
FIG. 24 is a perspective view of an exemplary embodiment of a slider of the plate assembly of FIG. 21 from above.
Figure 25:
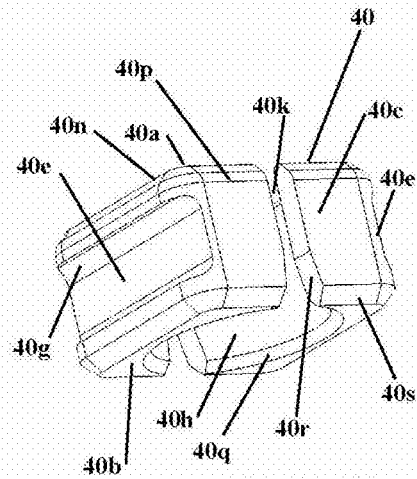
FIG. 25 is perspective view of the slider of FIG. 24 from a side thereof.

FIGS. 24 and 25 show the slider 40 generally used with plate assembly 200. Slider 40 has a square or rectangular shape with a top surface 40a, a bottom surface 40b, a front face 40c, a back face 40d, a groove 40e on both sides of slider 40, preferably machined with blend radii 40f and 40g to avoid any stress risers, a central hole 40h, and a chamfer 40j to break the sharp edge on the hole 40h where it meets top face 40a. A slot 40k cut through the front face 40c into the central hole 40h provides flexibility to the slider 40, and an additional rear slot 40m provides additional flexibility and a hinge point about which to flex. A chamfer 40n and radius 40p run around the top surface 40a to break any sharp edges and provide a smooth transition to avoid tissue impingement. A lower chamfer 40q transitions the bottom surface 40b and the central opening 40h, which helps make placement over a spinal implant easier. As the slider 40 must be compressed into plate opening 30g, chamfers 40r can be provided to allow for additional clearance in the slot for the slider 40 to be compressed, as the slider 40 will compress at an angle as it is inserted into plate 30. An additional chamfer, 40s allows the slider 40 to slide into plate opening 30g.

Figure 26:
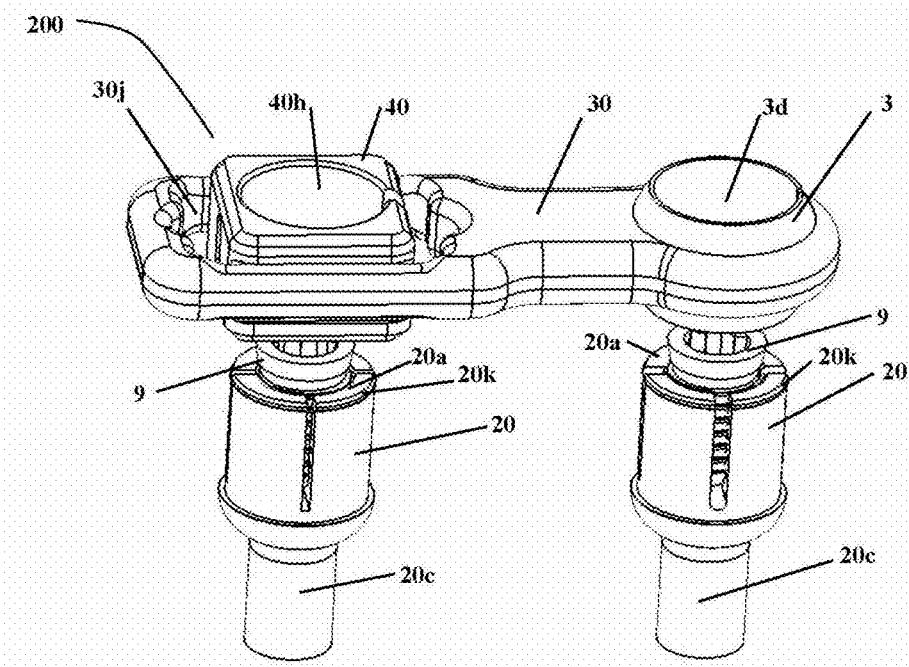
FIG. 26 is a perspective view of the plate assembly of FIGS. 22 to 25 placed above monoaxial screws.

FIG. 26 shows a plate assembly 200 with the plate 30 assembled with the spherical bearing 3 and slider 40 therein and the plate assembly 200 placed over the top of the monoaxial screws 20. Distance between the screws 20 can be compensated for by slider 40 and angulation of the screws compensated for by the spherical bearing 3. In FIG. 26, the plate assembly 20 is not engaged with the screw bodies.

Figure 27:
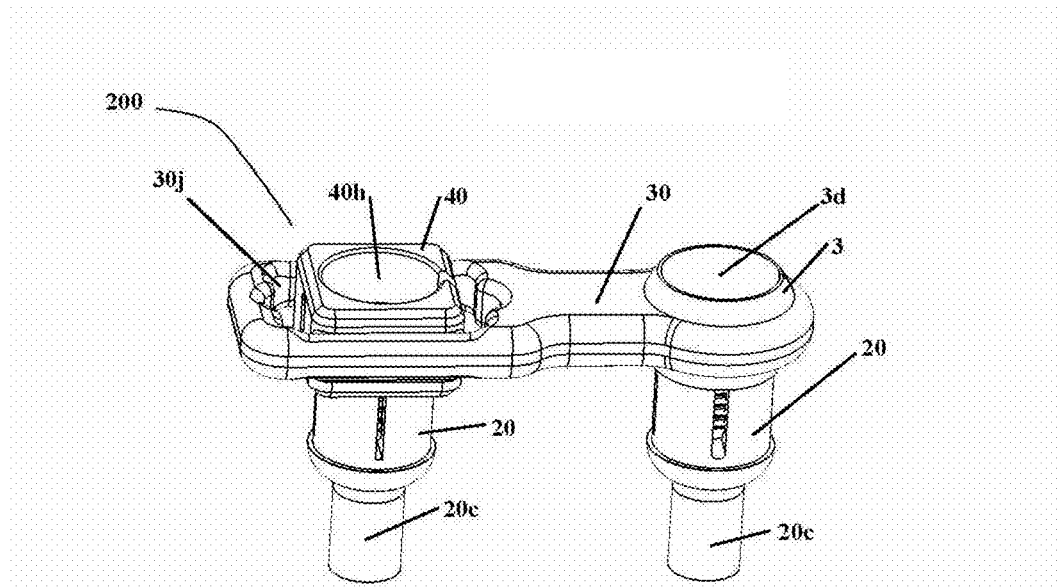
FIG. 27 is a perspective view of the plate assembly of FIG. 26 partially engaged with the monoaxial screws.

FIG. 27 shows the plate assembly 200 with the plate 30 assembled with the spherical bearing 3 and slider 40 therein and the plate assembly 200 placed over the top of the monoaxial screws 20. Distance between the screws 20 has been compensated for by slider 40 and angulation of the screws 20 has been compensated for by the spherical bearing 3. In FIG. 27, the plate assembly 200 is partially engaged with the top of the screw bodies 20.

Figure 28:
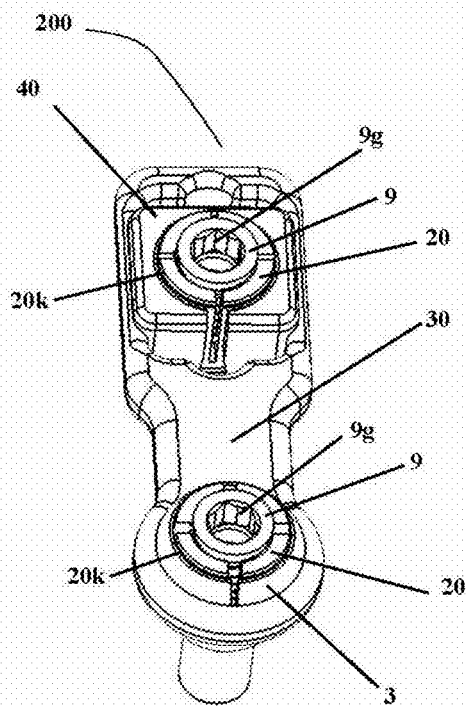
FIG. 28 is a perspective view of the plate assembly of FIG. 26 fully engaged with the monoaxial screws.

FIG. 28 shows the plate assembly 200 with the plate 30 assembled with the spherical bearing 3 and slider 40 therein and the plate assembly 200 placed over the top of the monoaxial screws 20. Distance between the screws 20 has been compensated for by slider 40 and angulation of the screws 20 has been compensated for by the spherical bearing 3. In FIG. 28, the plate assembly 200 is fully engaged with the screw bodies 20. By tightening the set screws 9, the slider 40 and the spherical connection will be fully locked, along with the plate 30 to the screws 20.

Figure 29:
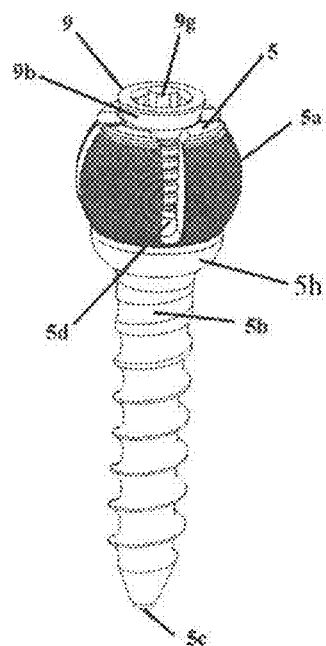
FIG. 29 is a perspective view of an exemplary embodiment of a fixed screw with a spherical head.
Figure 30:
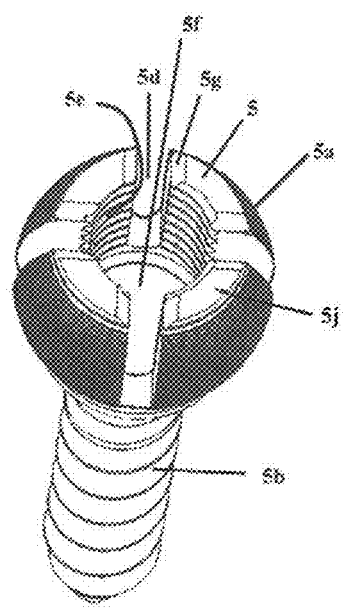
FIG. 30 is a perspective view of the fixed screw of FIG. 29 from above.

FIGS. 29 and 30 show a monoaxial screw 5 having a spherical bearing surface 5a machined into the surface thereof, such that the bearing and screw are a one-piece construction. The screw 5, having a top surface 5j, a bone thread 5b, and a tip 5c, has a threaded central hole 5e that extends to a desired depth and a bottom surface 5f, which is formed during machining and can be flat, round, drill point, or another shape. The screw 5 can also be cannulated such that a small hole is provided through the entire part to allow a k-wire to pass. At least one slot 5d in the side of the sphere allows the sphere to be flexible and flex outward when the set screw 9 is tightened. A transition or neck 5h extending from the bone thread 5b to the sphere can be provided to prevent the sphere from resting directly on a bone, which would inhibit polyaxial motion. For purposes hereof, this screw construct is defined as a monospherical screw.

Figure 31:
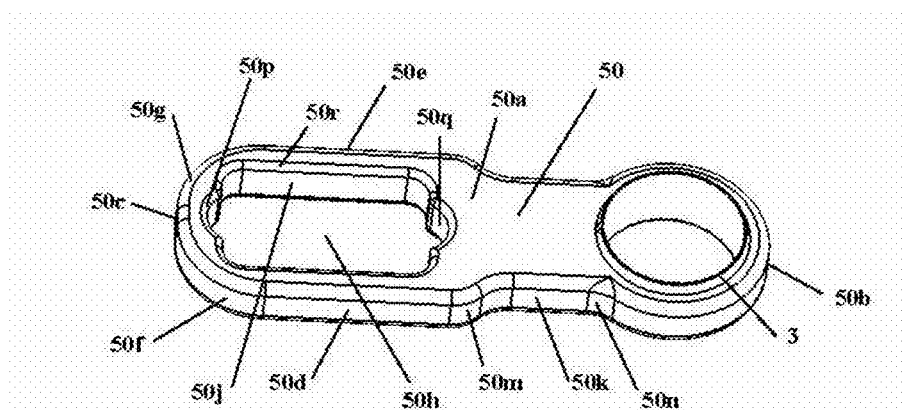
FIG. 31 is a perspective view of a further exemplary embodiment of a plate for the plate assembly of FIG. 33.

FIG. 31 shows an alternative plate 50 having a top surface 50a, a front round edge 50b, a central hole for containing or accepting a spherical bearing or monospherical screw, a rectangular section 50d with a back edge 50c, corner radii 50f and a rectangular opening 50h. The rectangular opening 50h has an upper blend radius 50r, a lower blend radii, and a side wall 50j. A smaller rectangular section 50k is present to allow for a more bendable or contourable zone that is transitioned into the front round section by radii 50n and to the rectangular section by radii 50m. Two openings in the plate: 50p in the back and 50q in the front of the rectangular opening 50h allow for instrument access. This plate configuration allows adjustment of plate length without the use of a separate slider component.

Figure 32:
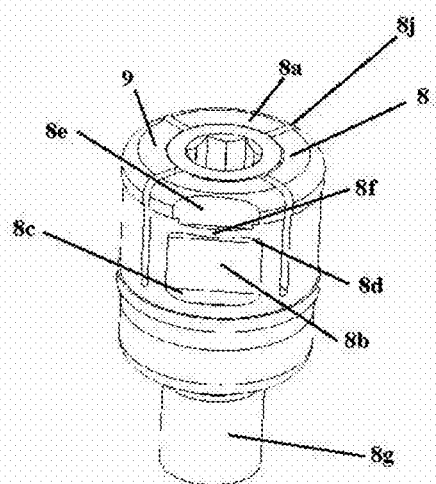
FIG. 32 is a perspective view of another exemplary embodiment of a screw body for the plate of FIG. 31.

FIG. 32 shows a screw body 8 having a top surface 8a and two grooves 8b machined into the wall of the screw body 8 opposite each other. The groove 8b has a blend radius 8d at the top and a blend radius 8c at the bottom. Cutting the groove 8b creates a lip 8f. A flat 8e can be added to provide an easier way to slide plate 50 onto the implant and also provide a visual alignment clue for the surgeon. Slots 8j are cut to allow the groove section to have sufficient flexibility such that tightening set screw 9 forces the groove outward against the rectangular side wall 50j of the plate 50 to lock the screw body to the plate 50. It is noted that the body in FIG. 32 is shown as a polyaxial screw body having a bone screw with a spherical head 8g. However, any of the screws mentioned herein, such as the monoaxial screw, can have the simple groove configuration.

Figure 33:
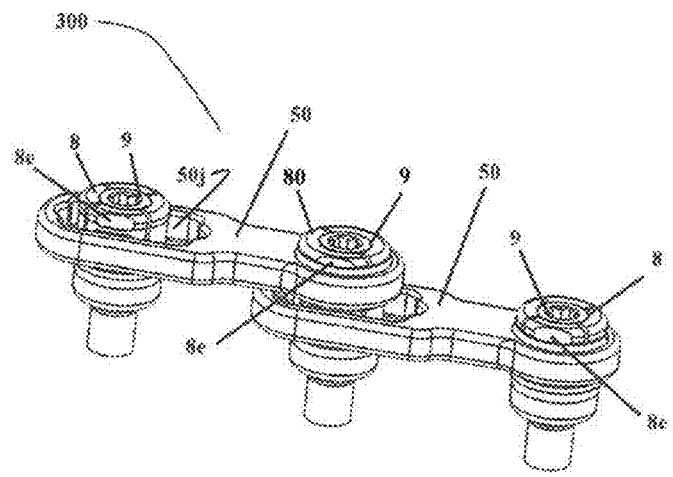
FIG. 33 is a perspective view of an exemplary embodiment of a dual level construct with the plate of FIG. 31.

FIG. 33 shows a dual level construct whereby two plate assemblies are placed over screws 8, 80 and are subsequently locked by tightening respective set screws 9. In this configuration, screw 80 is simply a longer body version of the polyaxial screw body or monoaxial screw. The extended body of screw 80 has the same features but is longer to accept the two stacked plates 50. It is noted that the plates 50 are stacked so that the taller central screw 80 fits one spherical bearing from one plate (left) and slides within the second plate (right). Of course, this can be inverted, such that the plates 50 join at the identically shaped ends.

Figure 34:
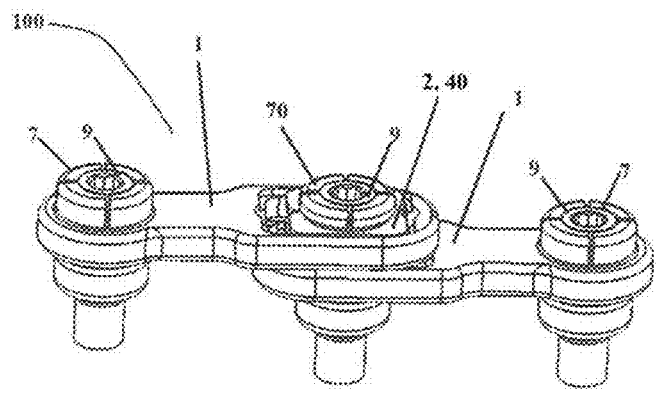
FIG. 34 is a perspective view of an exemplary embodiment of a dual level construct with the plate of FIG. 1.

FIG. 34 shows a dual level construct whereby two plate assemblies are placed over screws 7, 70 and are subsequently locked by tightening respective set screws 9. In this configuration, screw 70 is simply a longer body version of the polyaxial screw body or monoaxial screw. The extended body of screw 70 has the same features but is longer to accept the two stacked plates 1. It is noted that the plates 1 are stacked so that, in one embodiment, the taller central screw 70 fits one spherical bearing from one plate and fits within the slider of the second plate or this configuration can be inverted as shown in FIG. 34 so that the plates 1 join at the identically shaped ends to have the screw 70 fit within two stacked sliders, e.g., sliders 2, 40.

Figure 35:
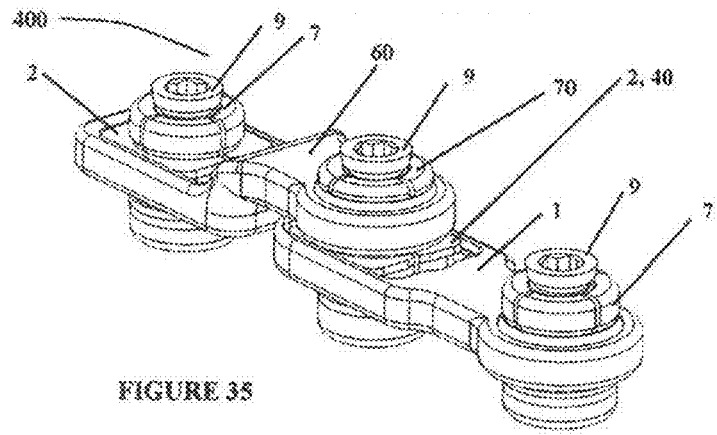
FIG. 35 is a perspective view of an exemplary embodiment of an offset plate dual level construct with the plate of FIG. 1.

FIG. 35 shows a dual level construct whereby one plate assembly with plate 1 is connected to an offset plate assembly having an offset plate 60 by placing the plates 1, 60 over screws 7, 70 and subsequently locking them by tightening the respective set screws 9. In this configuration, the screw 70 is simply a longer body version of the polyaxial screw body or monoaxial screw. The extended body of screw 70 has the same features but is longer to accept the two stacked plates 1, 60. It is noted that the plates 1, 60 are stacked so that the taller central screw 70 fits one spherical bearing from one plate (here, plate 60) and fits within the slider 2, 40 of the second plate (here, plate 1). Of course, this configuration can be inverted so that the plates 1, 60 join at the identically shaped ends.

Figure 36:
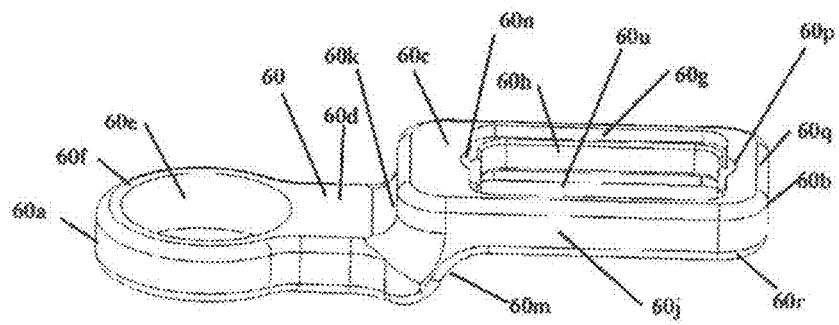
FIG. 36 is a perspective view of the bottom the offset plate of FIG. 35.
Figure 37:
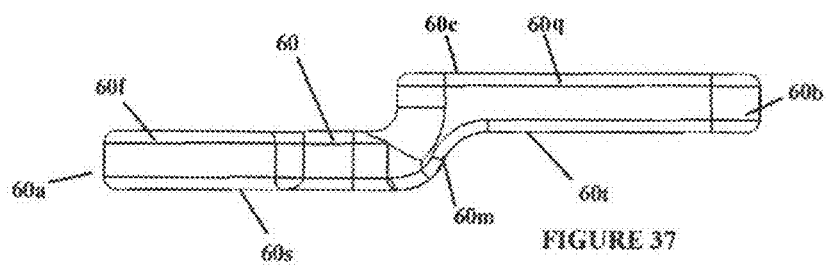
FIG. 37 is a side elevational view of the offset plate of FIG. 35.

FIGS. 36 and 37 show the offset plate 60. When stacking two plates without offset, one plate is higher than the other plate, which raises the height of the screw body at the end of the higher plate. This height difference can be compensated for by offsetting the plate. The offset is effectively the thickness of the plate. The offset plate 60 is shown here as a recessed plate, but it can be any of the versions and variations discussed herein. The offset plate 60 has a top surface 60t on the rectangular section 60j that is offset from the top surface 60s of the round section of the offset plate 60. This configuration also creates an offset of bottom faces 60d and 60c. To blend the steps together, blend radii 60m and 60k, blend the top and back together to avoid any sharp edges. Blend radii 60f and 60r run around the plate to smooth the outside edges. The recessed pocket and other features are the same as plate 1. Provided is a front round edge 60a and a central hole 60e for containing or accepting a spherical bearing or monospherical screw, a rectangular section 60j with a back edge 60b, and a rectangular opening 60u. The rectangular opening 60u has an upper blend radius 60r and lower blend radii 60g, 60q, and a side wall 60h. Two openings in the plate: 60n in the back and 60p in the front of the rectangular opening 60u allow for instrument access.

Figure 38:
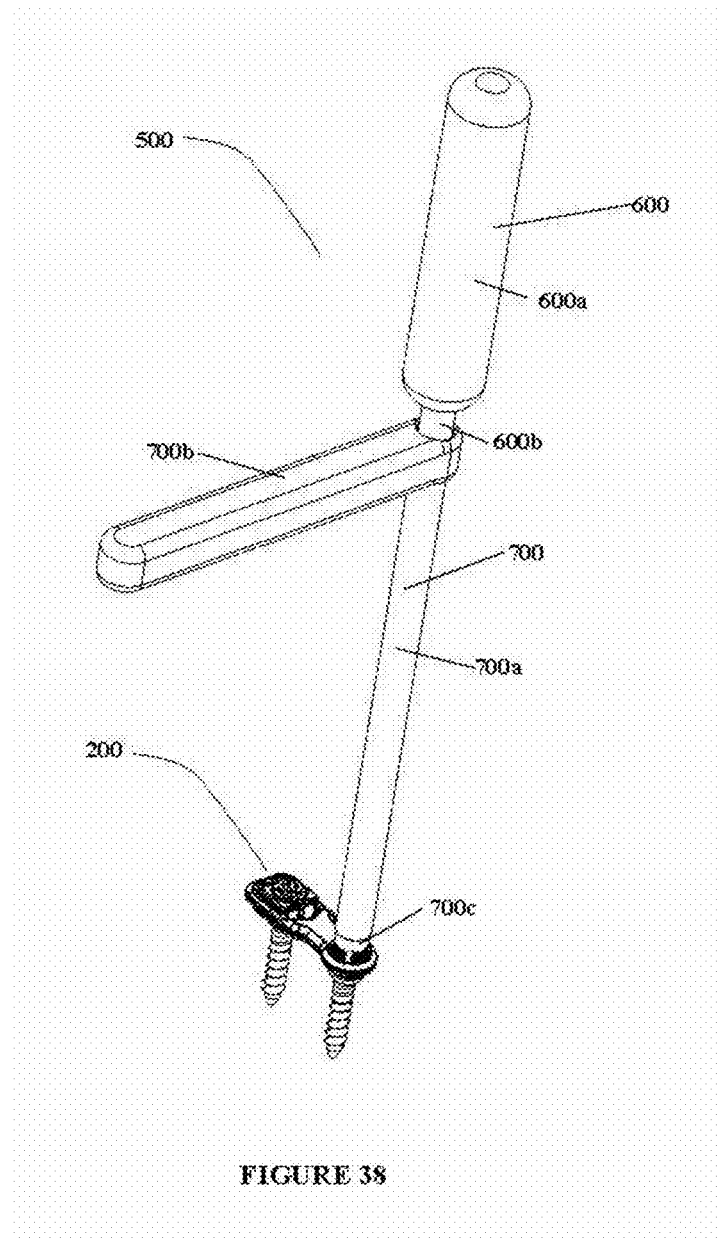
FIG. 38 is a perspective view of exemplary embodiments of a plate assembly, a set screw driver, and a counter torque-screwdriver.

FIG. 38 is a general illustration 500, showing one instrument variation for locking the assembly as well as providing features for turning a monoaxial or monospherical screw into bone. Shown is an implant assembly, generally represented by 200, and an instrument 700 that engages the slots (e.g., 5d, 7d, 8j, 20r) in the body of the screw head at the tip 700c. The shaft 700a of the instrument 700 connects to a handle 700b that can be permanently or temporarily attached thereto. A screw driver 600 has a handle 600a connected to shaft 600b can turn and lock the set screw (e.g., set screw 9) when instrument 700 acts as a counter torque instrument to prevent rotation of the plate and the screws.

Figures 39, 40, 41:
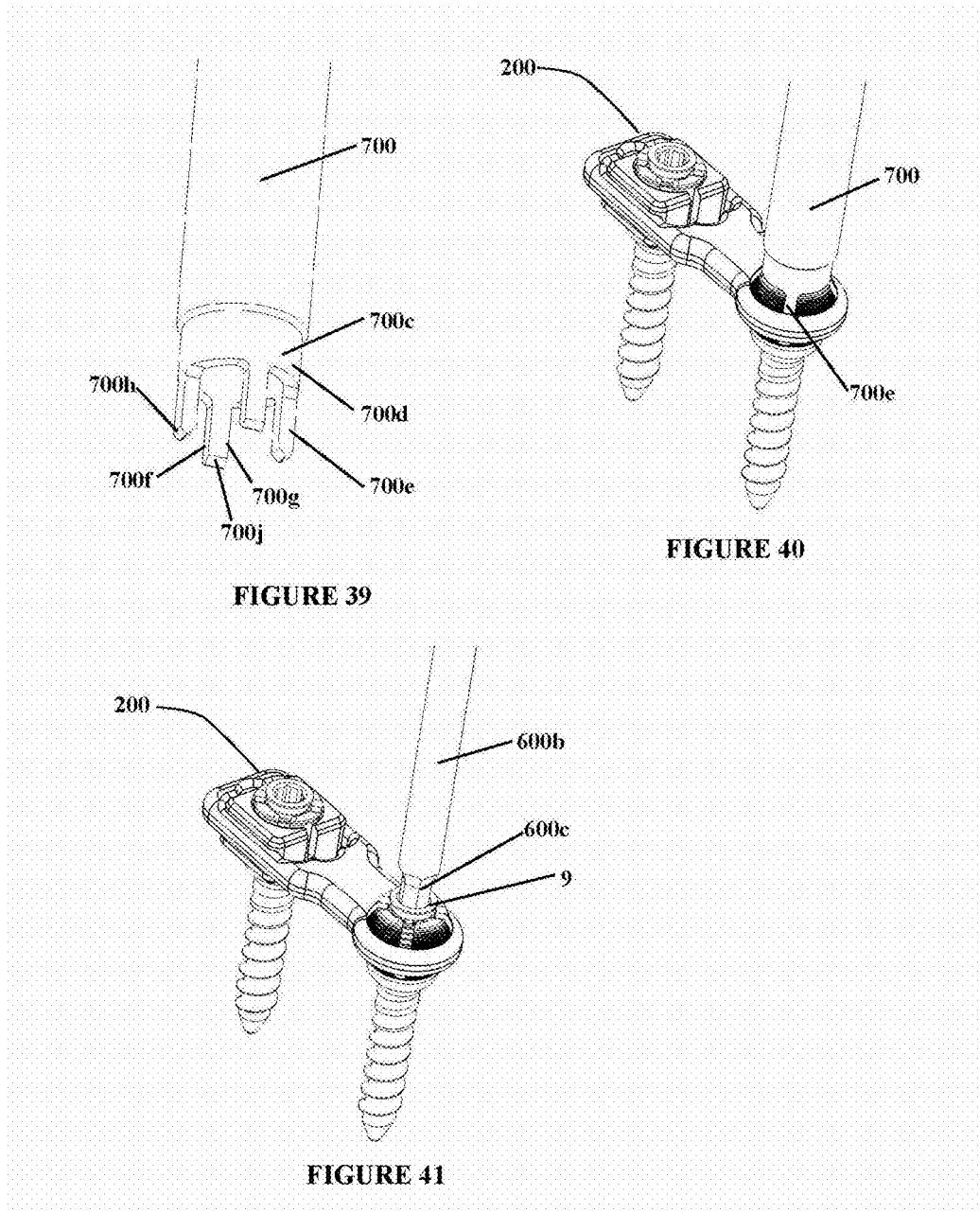
FIG. 39 is a perspective view of a tip of the counter torque-screwdriver of FIG. 38.
FIG. 40 is a perspective view of the tip of the counter torque-screwdriver of FIG. 38 engaging an assembly.
FIG. 41 is a perspective view of the tip of the set screw driver of FIG. 38 engaging an assembly.

FIG. 39 details screw engagement features of instrument 700. In an exemplary embodiment, instrument 700 is a tube having a bore. The tip 700c can be recessed to reduce its diameter where it engages the top of the bone screw body. To engage the slots, a series of prongs 700e are provided, having a first side 700f and a second side 700g, such that flats are formed that can at least partially engage with the side walls of the slots in the screw heads. Depending on the direction of rotation, not all sides and flats will be in contact. An external chamfer 700h allows the instrument easier sliding within the bearing, when that variation is used. A second chamfer 700j aids in starting the instrument 700 within the slots of the screw body. This exemplary configuration works as a bone screw driver as well, and can drive the monoaxial and monospherical screws into a bone.

FIG. 40 shows instrument 700 and prongs 700e engaged with a screw, which, in this example, is a monospherical screw, but the screw can be any of the variations described herein.

FIG. 41 shows the set screw driver shaft 600b and tip 600c engaged with set screw 9. As previously described, the tip 600c of the driver can be of a myriad of different designs, including hex, torx, square, star, or other variations.

Figure 42:
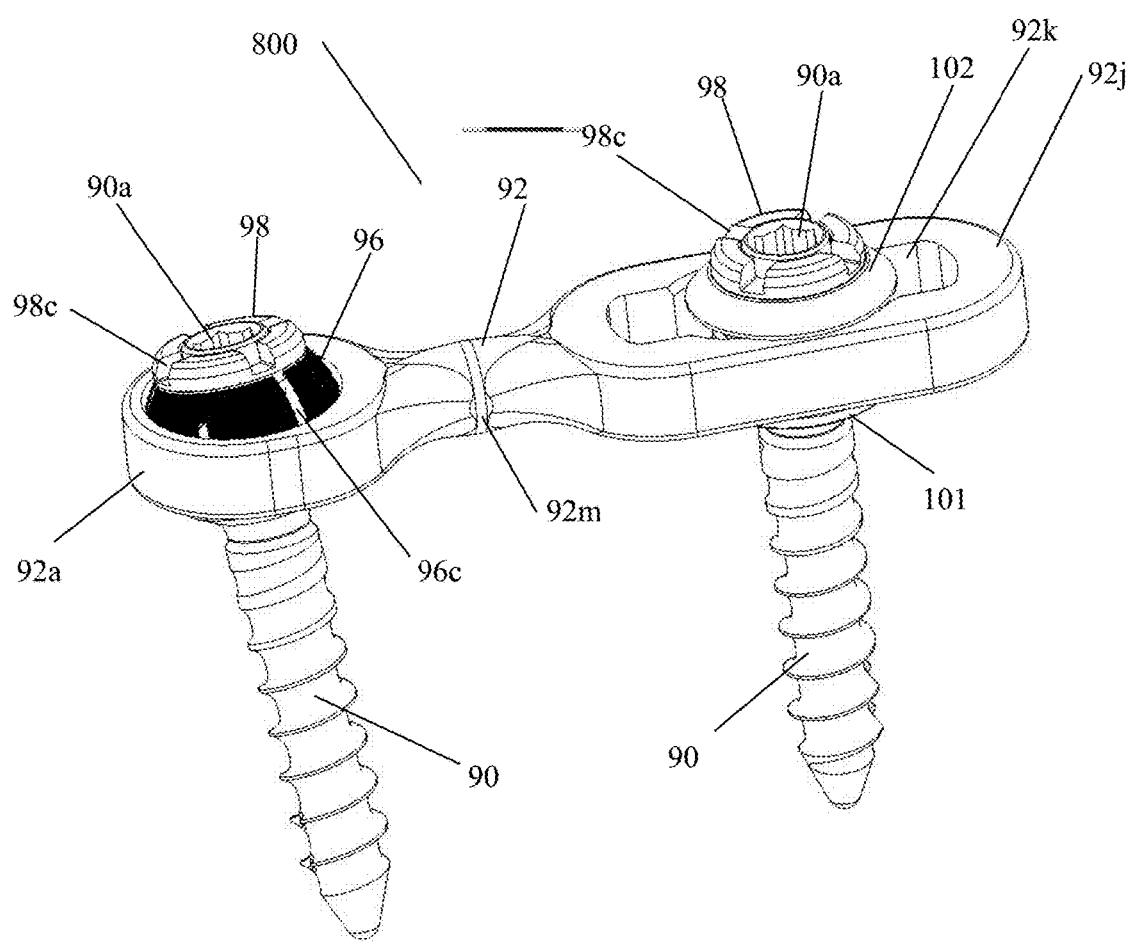
FIG. 42 is a perspective view of an exemplary embodiment of a plate rod construct having a round or semi-round center section and an alternative sphere and slider mechanism.

FIG. 42 details a variation of an assembly 800 of a plate rod construct 92, which is similar to plate 1. However, the middle section 92m is shown with an alternative round geometry. This configuration creates a more rod-like structure between the first end 92a, configured to hold the spherical bearing 96, and the second end 92j, configured to hold a sliding mechanism within a slot 92k. The spherical bearing 96 is slotted, as in previous descriptions, which allows the bearing to be flexible enough to fit within a pocket in the first end 92a of the plate rod construct 92. The bearing is then retained within the first end pocket, but is free to rotate. The nut 98 is then inserted into the bearing 96, which has the ability to retain the nut 98 therewithin. This eliminates the need for having a separate nut and saves the surgeon an extra step of placing a nut after the construct 92 is in place over the bone screws 90. A locking nut 98 is turned by features therein with an instrument. In this case, the instrument engages slots 98c to turn the nut 98. The locking nut 98 can be shaped in other ways, such as hexagonal, torx, or other forms, to engage the instrument. To prevent the bone screw from turning in the bone, the bone screw is held rotationally stable by a screw driver shaft engaged with feature 90a, which, in this example, is shown as a hexagon, but it may be other forms. The slider second end 92j has an upper washer 102 and a lower washer 101. These washers are assembled to the plate 92 with the locking nut 98. A retention feature in washer 101 engages a feature on the locking nut 98, which holds the assembly in slot 92k of the plate rod construct 92. Thus, the locking nut 98 can also be one-piece with the slider, eliminating the need to place a separate nut. When the nut 98 engages the top threads on the bone screw 90, the washers 101, 102 are compressed against the plate rod construct 92, locking the assembly to the plate rod construct 92. More details of the components in the assembly view of FIG. 42 follow in further figures.

Figure 43:
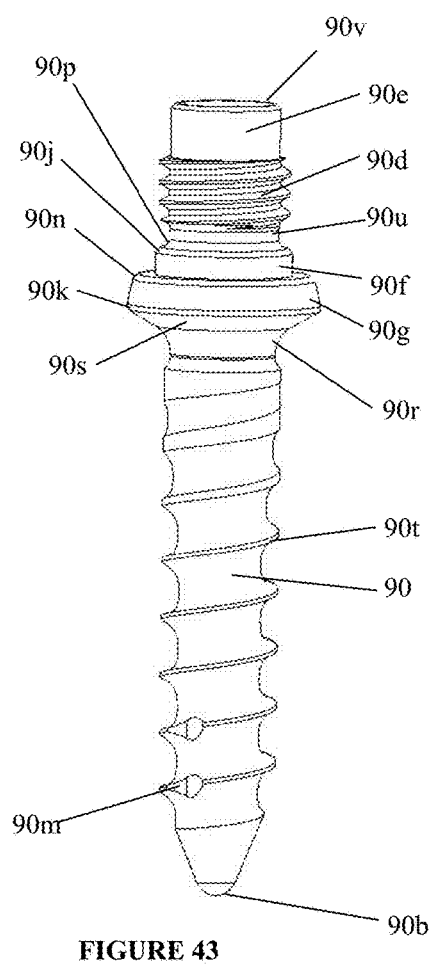
FIG. 43 is an elevational view of an exemplary embodiment of a bone screw, such as the bone screw in FIG. 42.
Figure 44:
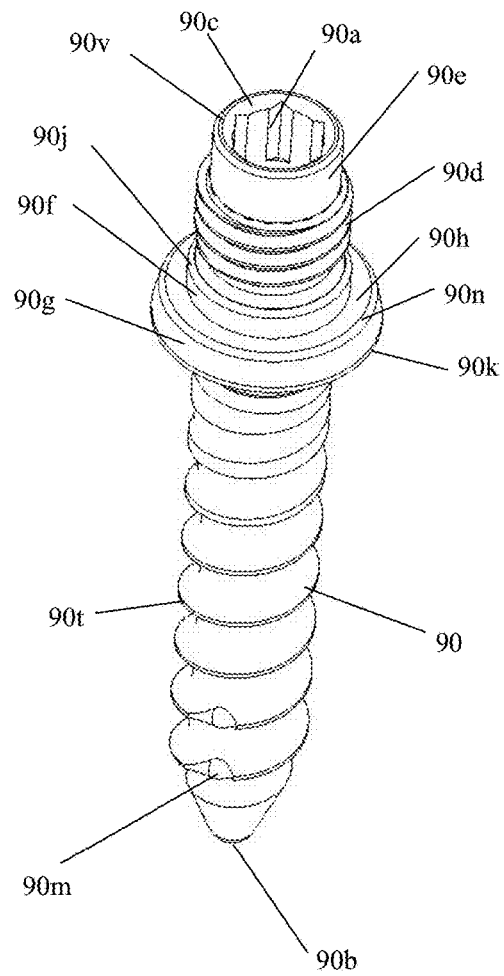
FIG. 44 is a perspective view of the bone screw of FIG. 43.

FIGS. 43 and 44 detail the bone screw 90. Bone screw 90 has a thread 90t constructed to engage bone, a first end 90b, and a second end 90v. The bone thread 90t has the option as shown for self-cutting and tapping features 90m, which allow the screw 90 to tap the bone without a separate tap. The top of the bone screw 90 has a post with a threaded portion 90d, a non-threaded portion 90e, an undercut 90u, a cylindrical section 90f, and a blend radius 90p along with a small chamfer 90j. The top of the bone screw 90 also has a feature 90a for connecting with a screw driver. This is shown in FIG. 44 as a hexagon, but it can be a variety of other forms, including torx, square drive, or others. The non-threaded portion 90e allows the nut 98 to engage the post of the bone screw 90 without having the need to engage the threads first. This makes it much easier to align the threads of the nut 98 to the threads 90d on the post. The undercut 90u is used in manufacturing to eliminate any partial or incomplete threads. This prevents the threads from cutting too far down the post and allows the locking nut 98 the ability to use the entire thread without binding on a partial thread. The cylindrical section 90f fits within the bottom of the locking nut to help maintain the concentricity of the locking nut to the post under loading. Additionally, the cylindrical section 90f also adds in additional material to reinforce the screw post. While these features are beneficial, they could be eliminated and the device could still be functional. A tapered or chamfered portion 90g engages various features, such as part of the spherical bearing 96 and various slider components, the details of which follow in further figures. Between the thread 90t and the non-threaded portion 90e of the bone screw 90, is an expanded section including a blend radius 90r from the thread 90t to an outer edge 90k, which has the tapered portion 90g tapering inwards and upwards from the outer edge 90k to a blend radius 90n and then to a shelf 90h, which connects to the outer surface of the cylindrical section 90f. The tapered/chamfered portion 90g can also be of other shapes, such as partially spherical or elliptical.

Figure 45:
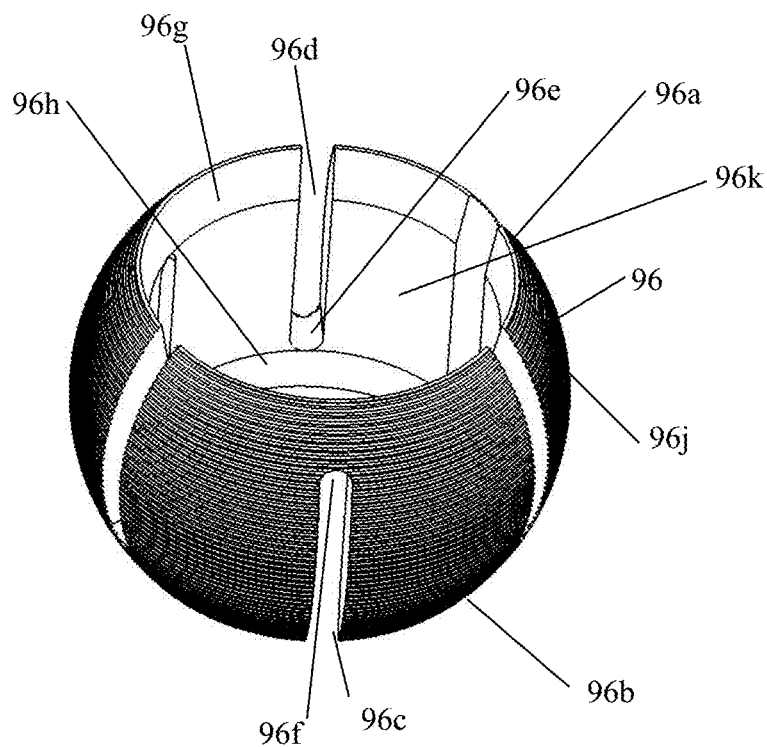
FIG. 45 is a perspective view of an exemplary embodiment of a spherical bearing.

FIG. 45 details a variation of the spherical bearing 96. The spherical bearing has a top face 96a and a bottom face 96b. While similar to the spherical bearing shown in previous figures, a set of slots 96d in the spherical bearing 96 extend from the top face 96a towards the bottom face 96b, and a set of slots 96c extends from the bottom face 96b towards the top face 96a. These slots 96c, 96d do not cut entirely through the spherical bearing 96, but terminate in blend radii 96e and 96f. These slots 96c, 96d make the bearing 96 flexible and capable of being compressed and expanded. A bore 96k extends through the bearing 96. A small top taper or chamfer 96g extends from the bore 96k to the top 96a, and a small bottom taper or chamfer extends from the bore 96k to the bottom face 96b. While it is preferable that the top and bottom tapers or chamfers be of the same angle and size for purposes of manufacturing and assembly, they can be of different angles. Also, instead of a taper of chamfer, the faces can be arcuate. As stiffness of the bearing 96 is directly related to wall thickness of the bearing 96 and the length of the slots 96c, 96d, stiffness of the bearing 96 can be readily adjusted as required. While the surface of the bearing 96 can be smooth, a surface pattern or roughness 96j can be machined or applied thereto. In this example, concentric rings are machined into the surface. This pattern can also be made by running a helical thread pattern over the spherical surface. Material properties of the spherical bearing 96 can also have an effect. Softer materials, such as various grades of commercially pure titanium can be used, as well as stronger materials, such as heat treated Ti-6Al-4V. Preferably, Ti-6Al-4V ELI with a surface pattern is used. This configuration can be replicated in other alloys, such as various stainless steels, and in composite and plastic materials.

Figure 46:
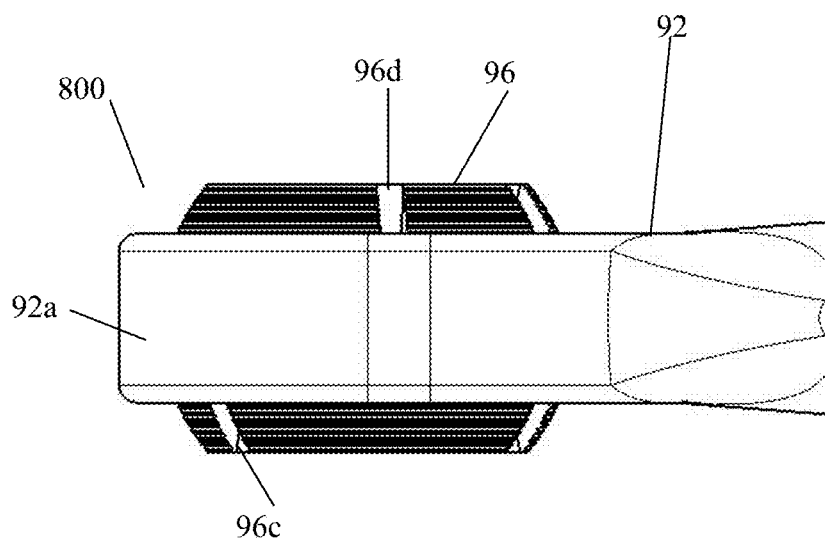
FIG. 46 is a fragmentary, side elevational view of the spherical bearing of FIG. 45 in a plate or rod end.

FIG. 46 shows part of the general assembly 800 and includes the spherical bearing shown in FIG. 45 held within the spherical bearing end or rod end 92a. The bearing 96 is elastic enough to be compressed to fit into the end 92a and expand enough to remain within the pocket in the end of the plate or rod end 92a.

Figure 47:
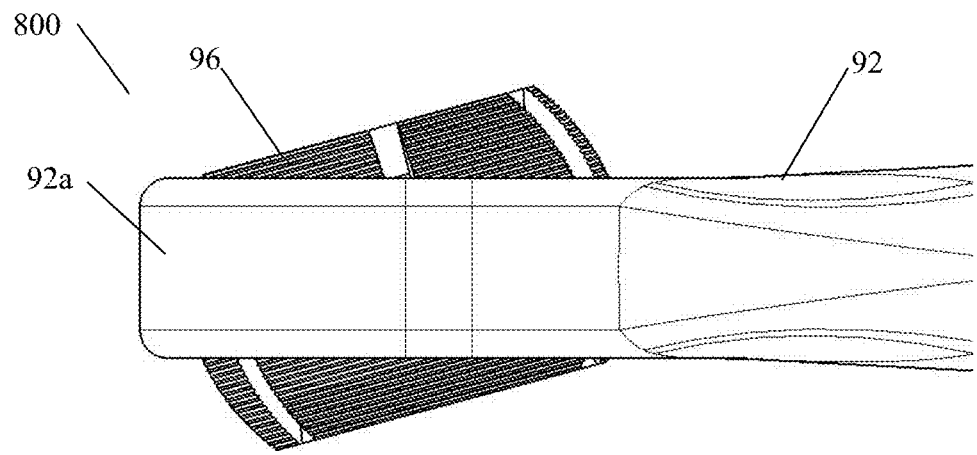
FIG. 47 is a fragmentary, side elevational view of the spherical bearing of FIG. 46 with the bearing rotated.

FIG. 47 shows that the bearing 96, although held within the plate/rod construct 92 can rotate within the pocket in end 92a.

Figure 48:
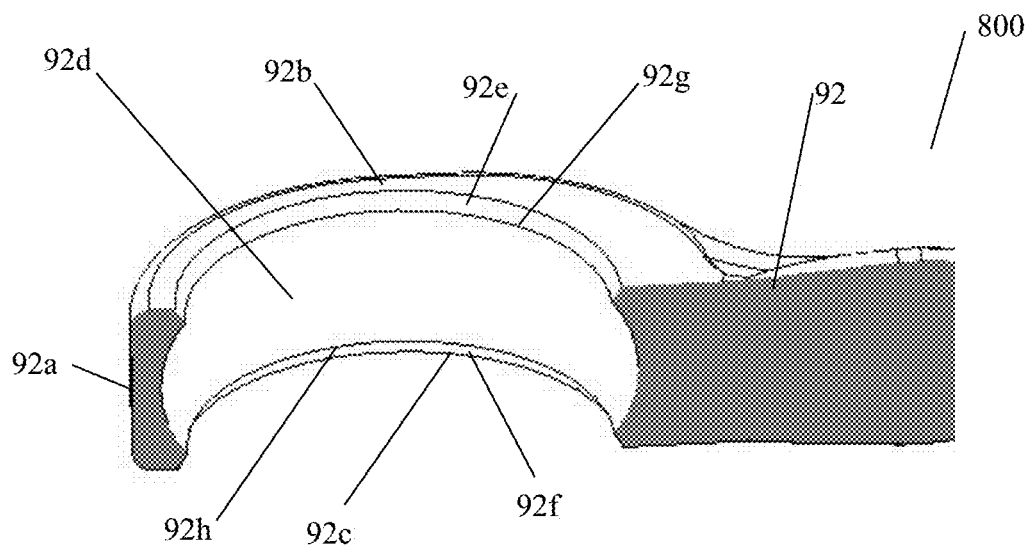
FIG. 48 is a fragmentary, cross-sectional view of the bearing housing in the plate or rod end of FIGS. 46 and 47.

FIG. 48 shows a cross-section of the plate or rod end 92a. A recess 92d is cut into end 92a. This recess 92d can be spherical, as shown, or an undercut of a different geometry. The spherical recess 92d or undercut does not need to match the dimensions of the spherical bearing 96, and testing has shown that having a spherical recess that is larger in diameter than the spherical bearing diameter provides better testing results. A chamfer 92e extends from the top surface 92b to the spherical opening, which creates an edge 92g where the chamfer 92e and spherical surface intersect. A chamfer 92f extends from the bottom surface 92c to the spherical opening, which creates an edge 92h where the chamfer 92f and spherical surface intersect. These edges help to bite into and grip the spherical bearing 96. By allowing the spherical seat of the recess 92d to be larger than the spherical bearing diameter, the bearing 96 can better engage edges 92g and 92h. As mentioned above, other undercut geometry can also create the proud edge geometry.

Figure 49:
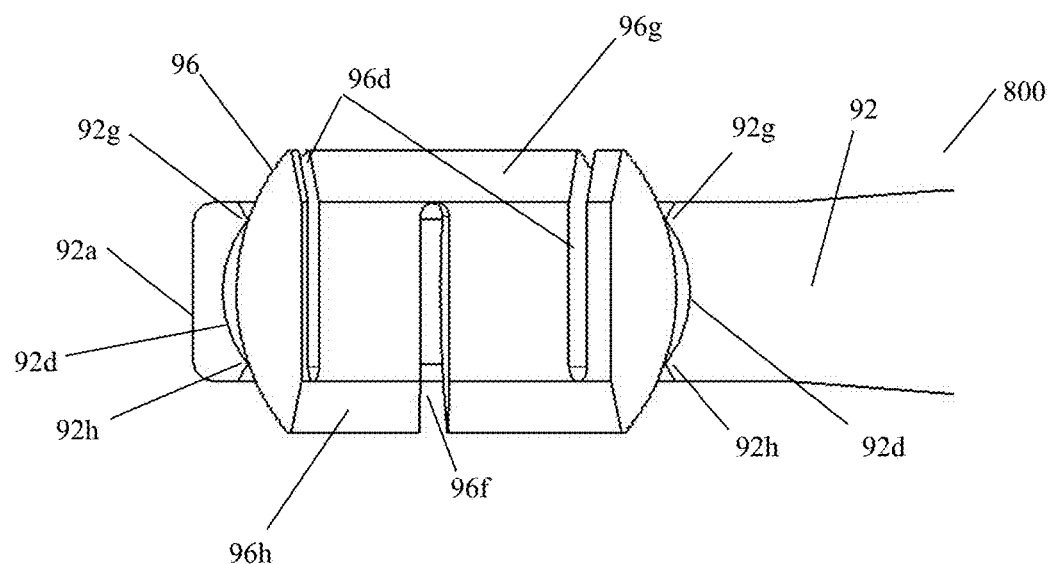
FIG. 49 is a fragmentary, cross-sectional view of the bearing and bearing housing of FIG. 46.

FIG. 49 is a cross-sectional view showing the bearing 96 seating within the plate or rod end 92a. As can been seen, the bearing 96 contacts edges 92g and 92h, and not the surface of the spherical recess 92d. As the bearing 96 is not constrained, it can rotate in all planes. The diameter of bearing 96 is sufficient to allow the bearing 96 to stay within the seat that is created by the spherical recess 92 and the edges 92g and 92h while still allowing the bearing 96 to rotate.

Figure 50:
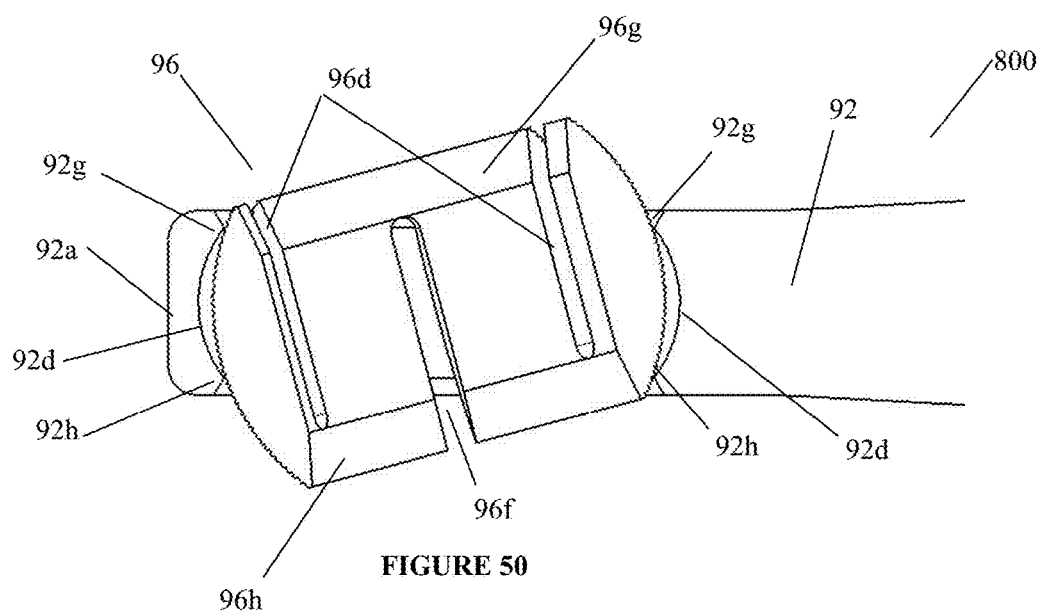
FIG. 50 is a fragmentary, cross-sectional view of the bearing and the bearing housing of FIG. 47 with the bearing rotated.

FIG. 50 is a cross-sectional view showing the spherical bearing 96 rotated within the plate or rod end 92a. This view makes it clear that the contact points of the bearing are the edges 92g and 92h. It is be possible to leave a small cylindrical portion between the spherical seat 92d and the chamfers 92g and 92h or to alter the geometry.

Figure 51:
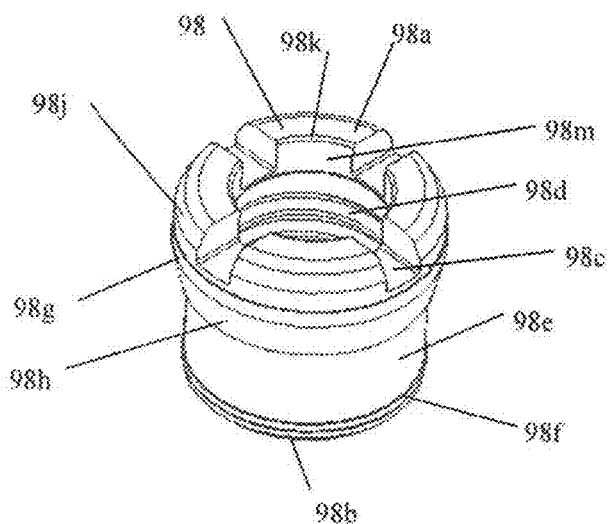
FIG. 51 is an perspective view of an exemplary embodiment of a locking nut.

FIG. 51 shows the locking nut 98 having a top surface or face 98a and a bottom surface or face 98b. A feature, such as grooves 98c, are provided in the locking nut 98 so the locking nut 98 can engage and be turned by an instrument. The locking nut can be provided with different features, such as hexagonal, torx, or other features that can engage an instrument. A threaded bore 98d extends from the bottom face 98b towards top face 98a. While the threaded bore 98d can extend through the entire locking nut 98, it is also possible to leave a non-threaded portion 98m. This non-threaded portion 98m provides additional material reinforcement to the instrument engagement features 98c, as the major diameter of the thread would cut through and reduce the material in this area. In certain cases, such as reduction of various spinal disorders, it is beneficial to have a bone screw 90 with a longer threaded region 90d. A fully threaded locking nut 98 allows the locking nut 98 to engage the threads and still fully seat and lock the assembly. As the screw driver and/or counter torque shaft that engages bone screw 90 (and, more specifically, the driving feature 90a) passes through the center of the locking nut 98, a chamfer or blend radius 98k is provided to help guide the screw driver or shaft into the locking nut 98. This variation of the locking nut 98 has a tapered collar 98h, which extends outward from the external cylindrical wall 98e. This taper contacts the taper 96g within the spherical bearing 96. While the taper 98g of the collar 98h can extend the length of the collar 98h, it can also be truncated to a cylinder to reduce the exterior diameter while providing clearance for the taper to fully engage in the spherical bearing taper. A lip or small extension 98f extends from the cylindrical wall 98e. This lip 98f can provide a retention ring to hold the locking nut 98 inside other components. For example, the spherical bearing 96 can have a groove that allows the lip 98f to fit therewithin, thereby holding the locking nut 98 within the spherical bearing 96 while allowing the locking nut 98 to turn within the spherical bearing 96. The outside edge 98j of the locking nut 98 is radiused and/or chamfered to prevent soft tissue impingement.

Figure 52:
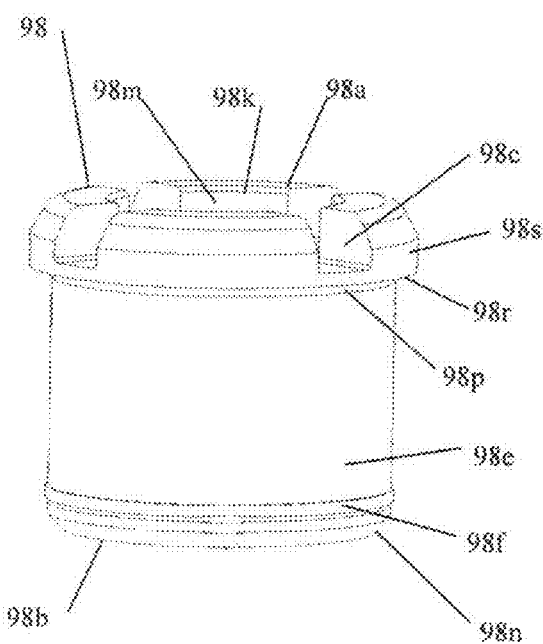
FIG. 52 is a side elevational view of the locking nut of FIG. 51.

FIG. 52 also shows the locking nut, however, this variation removes the tapered collar. A blend radius 98p minimizes a stress riser where the cylindrical wall 98e connects to the face 98r of the larger diameter section 98s.

Figure 53:
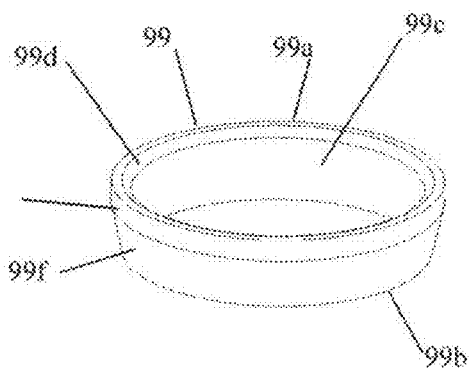
FIG. 53 is a perspective view of an exemplary embodiment of a tapered collar or ring.

FIG. 53 shows a separate tapered collar 99. This collar 99 has an upper surface 99a that rests against face 98r of the locking nut 98 shown in FIG. 52 and a bore 99c that allows the collar to be slid over lip 98f. This fit can be just sufficient to allow the collar 99 to slide over the lip 98f, but still be retained on the locking nut 98. A chamfer or radius 99d is provided to allow clearance for the blend radius 98p in the locking nut 98. This separate collar 99 and locking nut 96 configuration is preferable to the all-in-one locking nut 98 shown in FIG. 51 because the collar 99 can rotate independently of the locking nut 98. When the locking nut 98 is a one-piece construction, assembly torque creates friction that binds the tapered collar 98h in the tapered seat 96g of the spherical bearing. As the torque increases, the locking nut rotation starts to exert rotational forces on the construct. By having a separate collar 99, the collar 99 rotates independently, thereby reducing the rotational forces to the construct significantly.

FIG. 54 is an exploded view of the assembly 800, which is a preferred version having the locking nut 98 with the separate collar 99. For assembly, the bearing 96 is pressed into the plate/rod construct. As discussed previously, the slots allow the bearing 96 to be squeezed down in diameter to fit the smaller opening in the rod/plate construct. After assembly, the bearing 96 can rotate within the rod/plate construct. The locking nut 98 and collar 99 are assembled and the locking nut 98 inserted into the spherical bearing 96, where it is retained. With the bone screw placed in the pedicle, the locking nut 98 is aligned with the non-threaded post 90e to find the start of the threads and is turned to secure the plate/rod construct onto the bone screw 90. To fully lock the assembly 800, torque is applied to the locking nut 98 while preventing the bone screw 90 from turning by use of a counter torque shaft. As the locking nut 98 is tightened, the taper features 90g on the bone screw and 99f on the collar 99 engage the matching features 96g and 96h on the spherical bearing. This engagement causes the spherical bearing 96 to spread outward. As the spherical bearing 96 expands, the surface of the bearing 96 engages edges 92g and 92h in the plate 92. Additional torque generates significant locking of the spherical bearing 98 to the plate/rod construct, thereby locking the angle of the plate/rod construct relative to the bearing 96 and the bone screw 90 while locking the entire assembly to the bone screw 90. As force is exerted, the bearing 96 may be elastically deforming around the edges 92g and 92h so that the spherical bearing 97 is no longer spherical, but partially elongated.

Moving away from the spherical bearing, FIGS. 55 and 56 show a variation of the slider. Here, locking nut 98 passes through a top washer 102, through the plate/rod construct (not shown for clarity), and into a lower washer 101. The top washer has a top face 102a and a bottom face 102b. A bore 102d extends from the top face 102a through to the bottom face 102b. To provide a smooth and reduced outside profile of the top washer 102, the outside surface 102c is tapered. Of course, it can be radiused or have some combination of features, such as radiused and tapered. A blend radius or chamfer 102h between the bore 102d and the top face 102a allows for clearance of the blend radius 98p in the locking nut 98. A maximum outside diameter of the washer is large enough to cover at least a portion of the plate/rod connector face. A small cylindrical section 102g is provided to eliminate a sharp edge where the chamfered surface would intersect the middle face 102f. A conical section 102e engages the plate/rod construct so that compression of the conical section into the construct creates interference that locks the slider in position. The lower washer 101 has a top face 101a and a bottom face 101b. A cylindrical surface 101c has flats 101d machined into the surface. These flats 101d align and slide within the slot of the plate and prevent rotation of the lower washer 101 relative to the plate/rod construct. The lower washer section 101c can also be square or rectangular. A radius or chamfer 101j between face 101d and where the face would intersect face 101e is preferred to help provide a feature that the plate/rod construct can bite into, which, in practice, provides better gripping strength to the construct. This radius/chamfer feature 101j can be removed and the locking can still be sufficient under high enough torque. Surface 101e is a flat surface for engaging a bottom of the rod/plate construct. As with the top washer 102, a chamfer 101g or radius helps to reduce the profile and bulk of the lower washer 101. To avoid a sharp edge, a radius 101k and a small cylindrical section 101f are provided. Inside the lower washer 101, a lip 101n extends inward from bore 101h, and a chamfer 101p extends from the lip 101n to the top surface 101a. This lip 101n and chamfer 101p allow locking nut feature 98f to be pressed into the lower washer 101. Once the feature 98f is passed the lip 101n, the individual components become securely fastened together while still allowing the locking nut 98 to turn freely, as the locking nut lip 98f is within the larger bore 101h. This plate/rod construct provides a self-contained single functional unit that does not require any assembly or the addition of a locking nut at the time of surgery.

Figure 57:
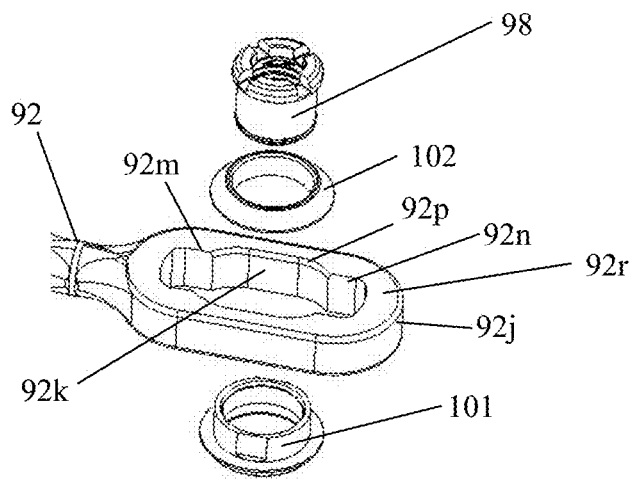
FIG. 57 is a, fragmentary, exploded, perspective view of an exemplary embodiment of a slider and a plate/rod end assembly.

The components in FIGS. 55 and 56 are shown in FIG. 57 with the plate/rod construct 92. The lower washer 101 slides within pocket 92k such that the flat surfaces 101d are aligned parallel to the long axis of the pocket. Smaller openings 92m and 92n extend through to pocket 92k. This allows the slide assembly to slide within pocket 92k but, even at the end of travel within the pocket, openings 92m and 92m still remain accessible. This accessibility allows an instrument to be inserted to act as a lever and move the sliding assembly in a desired direction. This ease of movement allows very effective compression or distraction of the spinal elements, by lengthening or shortening the distance between the center of the sliding assembly and the center of the spherical bearing.

Figure 58:
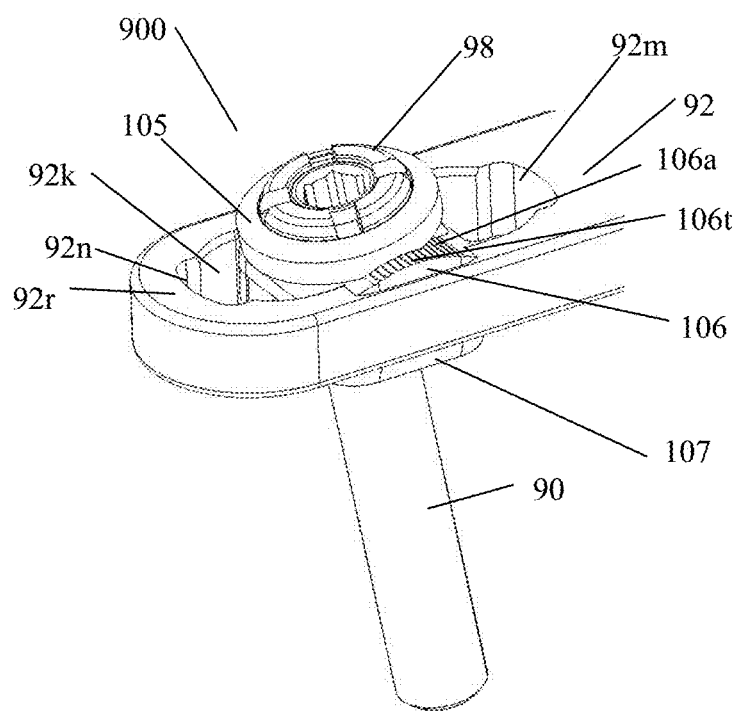
FIG. 58 is a fragmentary, perspective view of an assembly with an exemplary embodiment of a slider variation allowing bone screw rotation.
Figure 59:
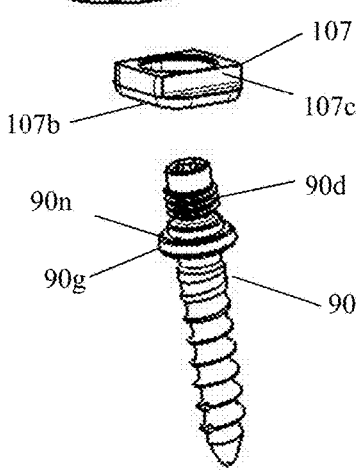
FIG. 59 is an exploded perspective view of the slider variation of FIG. 58.

FIGS. 58 and 59 show an alternative slider 900 that also allows rotation of the bone screw 90. Using the same bone screw as the spherical bearing end reduces inventory and simplifies a surgical procedure. In particular, by providing a spherical seat in a lower sliding component 107, the bone screw taper or arcuate surface 90g can rotate within the seat. This rotation is in a single plane. The upper sliding component 106 has an arcuate surface 106a, here shown with a grooved or tooth pattern 106t. The arc surface 106a is on approximately the same center of rotation as the spherical seat in lower sliding component 107. When the locking nut 98 is tightened, the nut 98 forces upper and lower sliding components 106, 107 against the plate/rod construct 92, while forcing washer 105 against upper sliding component 106, thereby simultaneously locking the assembly to the plate and the angulation of the bone screw 90. FIG. 59 shows the exploded view of the assembly and the order in which the components are assembled. The details of the components are shown in FIGS. 60 through 64.

Figure 60:
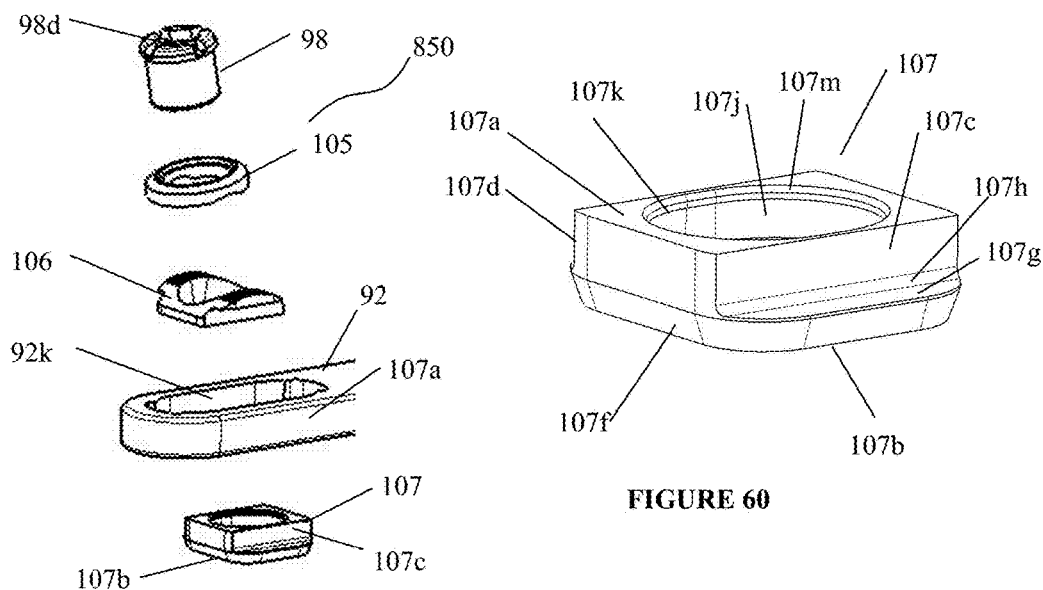
FIG. 60 is a perspective view of the lower sliding component of the assembly of FIG. 58.
Figure 61:
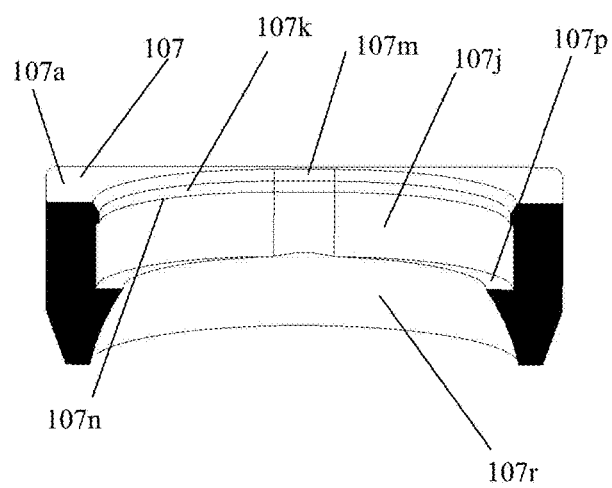
FIG. 61 is a cross-sectional view of the lower sliding component of the assembly of FIG. 58.

The lower sliding component 107 shown in FIGS. 60 and 61 includes a rectangular block having a upper surface 107a, a lower surface 107b, and side walls 107c, which are of sufficient dimensions to fit within the slot 92k in the plate 92 and allow sliding therein. Surface 107g is configured to contact the bottom of the plate/rod construct 92 with a bend radius 107h that reduces stress risers while providing material for the bottom edge of plate slot 92k to engage for better locking of the assembly to the plate. Of course, it is possible to configure the lower sliding component 107 so that the plate 92 contacts the radius 107h and not surface 107g and still achieve assembly locking. The feature 107h can also be a small chamfer and not a radius. The internal bore 107j is an oblong or oval pocket and the lip 107k that extends inwards is also oval or oblong. This oval or oblong shape gives the locking nut 98 clearance to pivot and allows angulation of the bone screw 90. The lip 107k is present to retain the locking nut 98 in the assembly by allowing the lip 98f on the locking nut 98 to be pressed past it until the lip 98f is in the larger oval or oblong shaped bore 107j. This retains the locking nut 98 but still allows the nut 98 freedom to turn, slide, and move up and down within the internal bore 107j. A chamfer 107m helps the locking nut lip 98f enter the bore 107j. A spherical seat 107r allows the bone screw's tapered or arcuate surface 90g to sit therewithin and rotate. Where the oblong or oval bore and the spherical seat 107r intersect, a small shelve 107p is created. To reduce bulk of the lower sliding component, blend radii and chamfers 107f are machined into the component 107. The lower sliding component 107 can also have a feature to engage the top sliding component 106. This can be, for example, a groove or slot in the side wall 107c that matches an extension from the top sliding component 106. This can be a single tab in a slot or multiple tabs into multiple slots as well or a variety of other engagement approaches, such as a groove or slot in the top sliding component 106 and a tab extending from the lower sliding component 107.

As shown in FIGS. 62 and 63, the top sliding component 106 includes a top arcuate surface 106*a* and a bottom surface 106*b*. The top surface 106*a* can be roughened or textured, such as is shown. In this example, small grooves are machined into surface 106*a*. This is one example; there are different ways to apply a textured surface, including crosshatching, blasting, chemical etching, and/or wire EDM cutting of splines or features, among other approaches. This surface can also be smooth without texture; however, better grip is provided with the mating component when a texture is present. A front wall 106*c* and a back wall 106*d*, along with the longer side walls 106*e*, 106*f* form a rectangular shape that can fit within the plate/rod construct opening 92*k* and have sufficient clearance to slide. Like other components described previously, the geometry of the part can be different, such as square or round, with features cut into the shape to work in the manner described herein. The sides 106*e*, 106*f* are cut into the rectangular shape so that the top surface 106*a* extends beyond and is wider than the rectangular section that fits within the plate opening 92*k*. Tapers or chamfers 106*h* allow for the sides of the rectangular section that fits within the plate/rod construct to contact the sides of the opening 92*k*, to provide a press fit with the plate when the top sliding component is fully seated in the slot. The tapers or chamfers can be eliminated; however, they provide additional strength to the construct and further resistance to sliding when the assembly is locked. An oblong or elliptical bore 106*g* allows the locking nut 98 to pass through the top sliding component 106. To reduce the amount of material removed from the top sliding component 106 by the bore 106*g*, the bore 106*g* is machined at a taper angle, such that faces 106*j* and 106*k* are angled or conical in shape.

The top washer 105, as shown in FIG. 64, has a top surface 105*a* and a bottom surface 105*b*. The generally cylindrical outer wall 105*h* is chamfered towards the top surface 105*a* to provide a smooth surface with less bulk for reducing tissue impingement. Of course, this surface can be partially spherical or arcuate or a combination thereof. It is preferable to cut an arced surface 105*c* into the bottom surface 105*b* in the washer 105 to create edges 105*j* and 105*k*, which help to engage the surface roughness feature 106*t* on the top sliding component 106. The arc in this case does not need to match the same dimension as the top surface 106*a* and can be smaller. Of course, the arcs can match exactly and the surface roughness or teeth can also be added to arc 105*c* or to some part of the bottom of the washer 105 to also engage the surface of the top sliding component 106. The top washer 105 also has a through-bore 105*d* and, preferably, a counter bore 105*e*, which allows the head of the locking nut 98 to sit within to reduce overall height and profile of the locked assembly.

Figure 65:
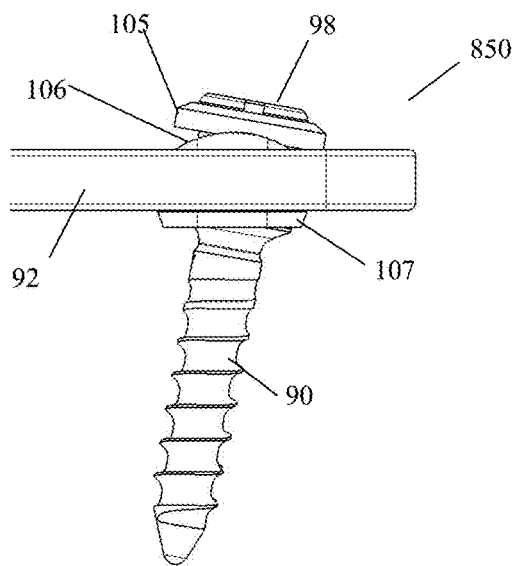
FIG. 65 is a fragmentary, side elevational view of an exemplary embodiment of a slider with the assembly in a partially rotated position.

As shown in FIG. 65, in which the locking nut 98 is tightened, the locking nut 98 engages the thread on the bone screw 90, which compresses the top sliding component 106 and the bottom sliding component 107 against the plate rod construct 92 while simultaneously locking the angle and location of the slider. Partial locking can also be accomplished by tightening the locking nut 98 to less than a full torque value, which can allow the slider to still slide while resisting changes in screw angle.

Figure 66:
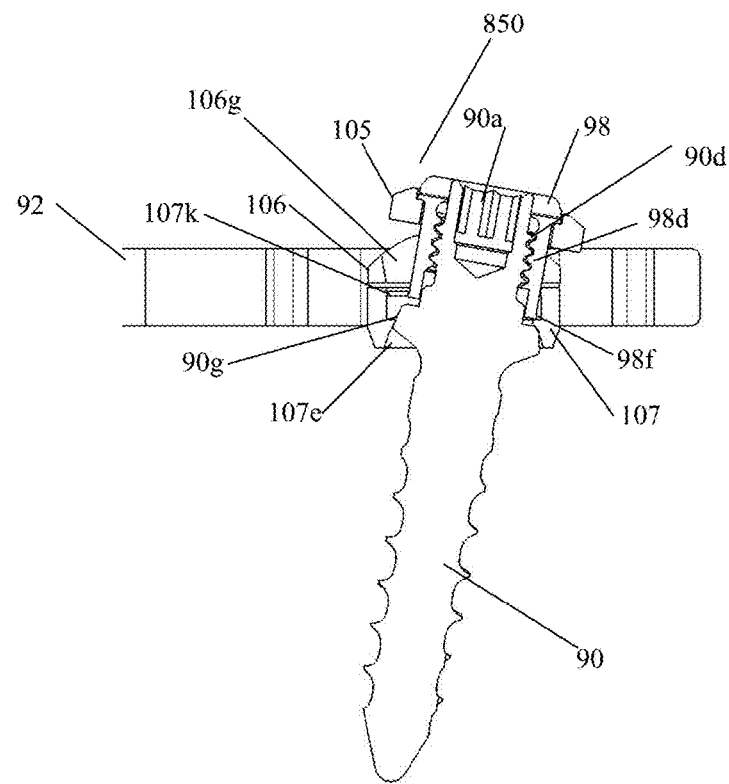
FIG. 66 is a fragmentary, cross-sectional view of the slider of FIG. 65 with the assembly shown in a partially rotated position.

FIG. 66 shows in the assembly in a sectional view to detail how the various components fit together. As shown, the locking nut lip 98*f* fits within the lower sliding component 107 and is retained by lip 107*k*. The surface 90*g* of the bone screw 90 rests in the spherical seat 107*e* of the lower sliding component 107. When tightened, which is done by using a counter torque driver engaged with the driving feature of the bone screw 90*a* and by turning the locking nut 98 clockwise, all the components are drawn together and locked together.

FIG. 67 highlights the bone screw engaging feature 90*g* can be partially spherical or arcuate, and is shown with reference numeral 90*g'*. This has been discussed earlier but, for clarity, is shown herein.

FIG. 68 is the same as FIG. 66, but has the bone screw shown in FIG. 67 with the arcuate or partially spherical surface 90*g'* replacing the taper 90*g*.

As discussed above, it can be beneficial for the top sliding component 106 to engage with the lower sliding component 107. During flexion-extension loading, whereby force is placed on the screw, the load tends to force the sliding components apart in opposite directions. If the washer 105 is fully engaged with the teeth 106*t* on the top sliding component 106, the lower sliding component 107 may slide more than the top sliding component 106. To prevent this from occurring, an anti-sliding feature or features in the two components is beneficial. These can be tabs in slots or grooves, or other ways, such as a pin or pins in holes. In addition, the top sliding component 106 and the lower sliding component 107 can be secured together in the plate rod construct so that tabs engaged in slots lock the two components 106, 107 together, such as in a snap together fit. The two components can also be loosely press fit together, although any approach to locking the upper sliding component 106 and lower sliding component 107 must allow the components the ability to move towards each other so that compression against the plate rod construct can occur to lock the assembly and the sliding components to the plate rod construct. Details of one variation of this are shown in FIG. 68A.

FIG. 68A shows that the top sliding component 106 has a slot 106*p* cut into the side wall 106*e*. This slot 106*p* extends through the side of the part. The shape is cut leaving prongs, hooks, or small extensions 106*r* that extend inward. This creates small features that can engage the lower sliding component 107. Small slots 106*s* can be provided to make the small hooks flexible, to allow for easier engagement with the lower sliding component 107. The lower sliding component 107 has part of the side wall 107*c* cut away, leaving two tabs or arms that extend upwards. A recess 107*u* is cut into the wall, which leaves an overhang 107*t* left behind. Thus, the prongs or hooks 106*r* can slide over the overhang 107*t* and snap into the recess 107*u*. This effectively holds the two components together. The overhang 107*t* in the lower sliding component 107 is shaped to contact wall 106*v* in the top sliding component 106 so that there is minimal clearance between wall 106*v* and overhang 107*t*. This configuration allows for sufficient room for the hooks or prongs to slide up and down within the recess 107*u*, which allows top sliding component 106 to slide up and down relative to bottom sliding component 107 and, when in a final locking state, overhang 107*t* engages wall 106*v*. This minimizes any possible sliding of the two components after locking the assembly. This makes the assembly more rigid and increases flexion-extension test values.

Figure 70:
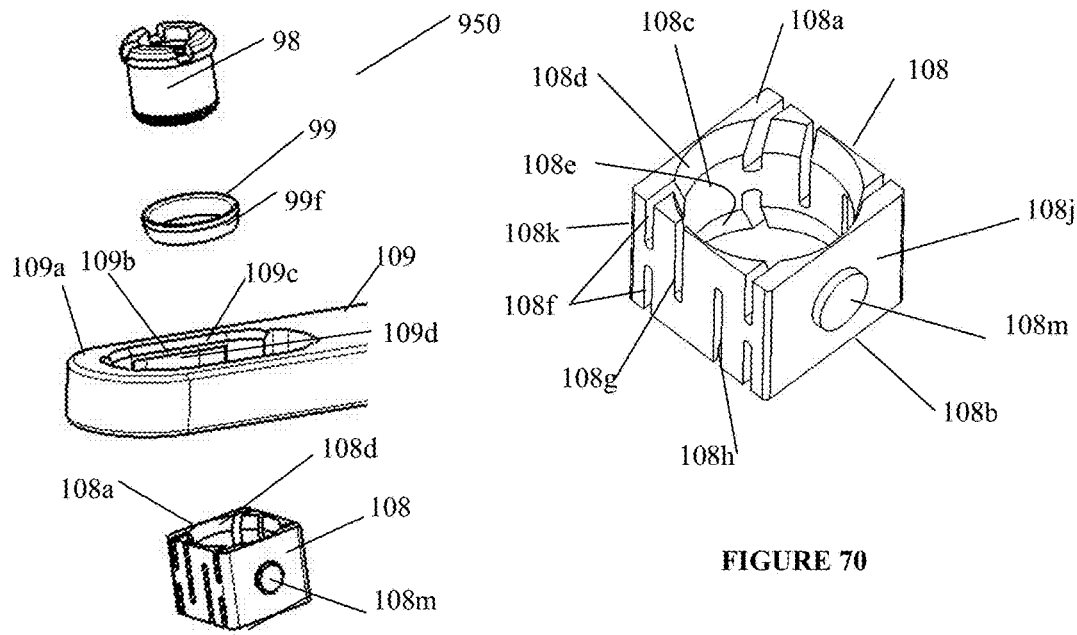
FIG. 70 is a perspective view of an exemplary embodiment of a slider block of the assembly of FIG. 69.
Figure 69:
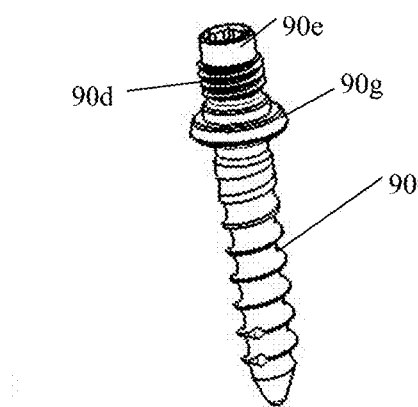
FIG. 69 is a fragmentary, exploded perspective view of an exemplary embodiment of a slider assembly.

FIG. 69 is an alternative slider 950 that also allows angulation. The basis of this variation is a cube 108 configured to flex outward when the locking nut 98 and collar 99 engage the top internal tapered surface 108*d* of cube 108 and the screw surface 90*g* engages the bottom taper 108*e* within the cube 108. As seen in FIG. 70, the cube 108 is cut with a series of small slots 108*f*, 108*g*, 108*h*. These slots, such as 108*g*, can extend from the top face 108*a* or from the bottom face 108*b*, such as slot 108*h*. These slots reduce the rigidity of the cube 108 and allow it to expand outward as the locking nut 98 is tightened on the post of the bone screw 90. Shorter length slots, such as 108*f*, direct the force partially above and below a lip 109*b* and chamfer 109*c* in plate 109. Small cylinders 108*m*, 108*n* are machined into the cube 108 to form pivot points. These cylinders 108*m*, 108*n* also help to retain the cube 108 in the plate/rod construct while allowing rotation of the cube 108. These cylinders 108*m*, 108*n* fit within an undercut 109*d* in plate 109. As the cube 108 is flexible, it can be pushed down into the plate/rod construct and, when properly seated, the cylinders 108*m*, 108*n* will expand outward to fit within the undercut 109*d*. During locking, surfaces 108*j* and 108*k* at least partially engage the internal surface of the plate/rod construct 109.

Figure 71:
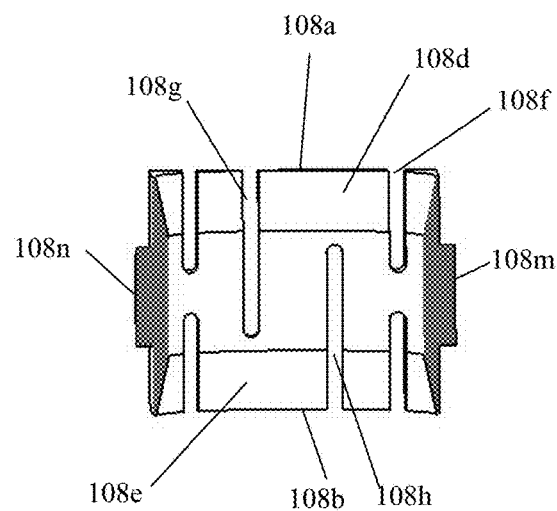
FIG. 71 is a cross-sectional view of the slider block of FIG. 69.

FIG. 71 is a cross-sectional view of the cube 108 that better shows the tapered features 108*d*, 108*e* connected to the bore 108*c*. The amount of flexibility of the cube 108 is directly affected by the length, number, and placement of the various slots. Thus, the slots can be tailored to the application. The cube 108, does not need to be a cube; it can be other shapes, such as rectangular, modified cylinder with flats, or another shape as desired. The engagement of the tapered surfaces 108*d*, 108*e* of the cube 108 and the surface 90*g* of the bone screw as well as the collar 99 and the locking nut 98 can cause significant outwardly directed force to lock the location and angle of the cube 108.

Figure 72:
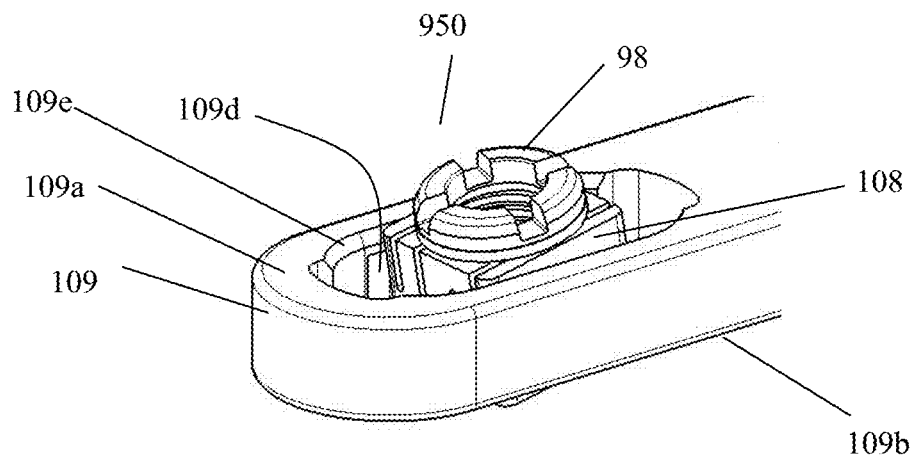
FIG. 72 is a fragmentary, perspective view of the slider assembly of FIG. 69 without the bone screw.
Figure 73:
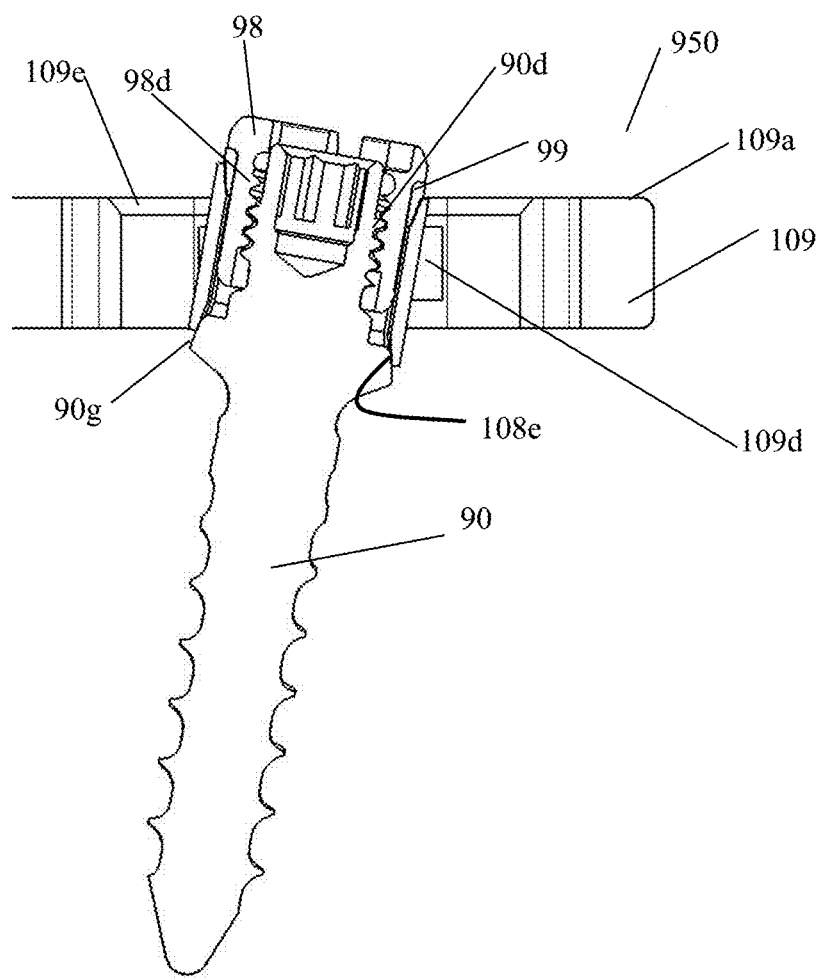
FIG. 73 is a fragmentary, cross-sectional view of the slider assembly of FIG. 72 with the bone screw.
Figure 79:
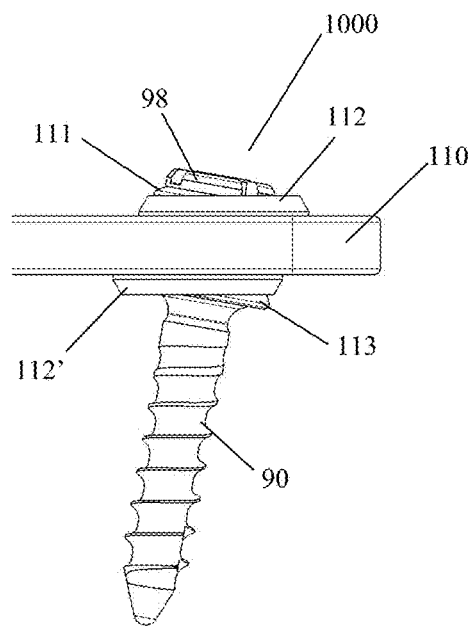
FIG. 79 is a fragmentary, side elevational view of the slider assembly of FIG. 74 with the screw locked at an angle.

FIG. 72 shows the assembly of FIGS. 69 to 71 prior to placement on the bone screw. As in previous embodiments, the locking nut 98 can be incorporated into the cube 108 making easier for the surgeon to use. Either the locking nut 98 can be slightly press fit into the cube 108, or retained in the cube 108 by engagement of the lip 98*f* of the locking nut 98 in a groove cut inside the bore 108*c* of the cube 108. The detailed sectional view of the locked assembly 950 is shown in FIG. 73.

FIG. 74 shows an exploded view of an alternative slider 1000. This slider 1000 allows for screw angulation and sliding and includes a top washer or collar 111, a upper sliding seat 112, a plate/rod construct 110, a lower bearing 113, and a lower sliding seat 112'. This variation can function with bone screw 90 having the taper 90*g* or arcuate surface 90*g'*.

Detailing the components shown in FIG. 74, FIG. 75 shows the collar 111 having an upper surface 111*a*, a lower surface 111*b*, and a central bore 111*c*. Surface 111*d* is spherical or partially spherical. A small cylindrical portion 111*e* is below the surface 111*d* (e.g., spherical portion). The face 111*f* is radiused or tapered to reduce soft tissue impingement and the intersection between 111*f* and surface 111*d* is radiused 111*g* to avoid any sharp edges. In FIGS. 74 and 76, the upper sliding seat 112 and the lower sliding seat 112' (which is similar in shape to upper sliding seat 112 but turned over) include an upper surface 112*a* and a lower surface 112*b*. A spherical seat 112*c* is machined in the top face and a through-bore 112*d* extends through the part. Two arms 112*e* are conical in shape and engage the chamfered surfaces 110*d* and 110*d'* of the plate or rod construct. FIG. 77 details the plate or rod construct 110, which has an upper surface 110*a* and a lower surface 110*b*. A slot 110*c* extends through the construct 110. A step cut into the top and bottom surfaces 110*f* creates a ledge 110*g*. A chamfer 110*e* is configured to engage the arms 112*e* on the upper sliding seat 112. Two small pockets 110*h* are smaller than slot 110*c*. The lower bearing 113, as shown in FIG. 78, has an upper surface 113*a*, a lower surface 113*b*, a spherical or partially spherical seat 113*c*, a cylindrical wall 113*d*, and a blend radius 113*h* to avoid any sharp edges. A bore 113*e* extends through the lower bearing 113 and a lip 113*f* extends inward into the bore 113*e* to create a ledge 113*g*. A chamfer 113*j* runs from top edge 113*b* to the lip 113*f* to provide a smooth transition and guide surface. During assembly, the locking nut 98 is pressed through the upper bearing 111, the upper sliding seat 112, the slot 110*c* in the plate/rod construct, and the lower sliding seat 113. The locking nut 98 is then pressed into the lower bearing 113 so that the lip 98*f* on the locking nut 98 engages and slides under the lip 113*f*. This locks the assembly together while allowing it to be loose enough to slide and move in the slot 110*c*. The bone screw 90 seats in the bottom of the lower bearing 113 in a tapered seat machined in the bottom of surface 113*a* and is configured to lock to the tapered surface 90*g* on the bone screw 90.

In use, the assembly and components generally shown as 1000 and in FIGS. 72 through 78 work such that the upper sliding seat 112 and the lower sliding seat 112' can slide independently relative to each other. This allows angulation and sliding of the assembly and is shown in FIG. 77. As the upper sliding seat 112 and the lower sliding seat 112' move, the spherical seats 111*d* and 113*c* can move within the matching spherical seats in the upper and lower sliding seats 112*c*, 112'*c*. It is noted that, as the upper and lower seats 112, 112' slide, the distance from center to center of the spherical seats 112*c*, 112'*c* increase. The locking nut 98 has sufficient threads to compensate for this nominal difference. When the assembly is locked, the conical feature 112*e* and both 112 and 112' lock into the tapered features 110*d* and 110*d'*, respectively, thereby locking the sliding and angulation of the assembly.

Figure 80:
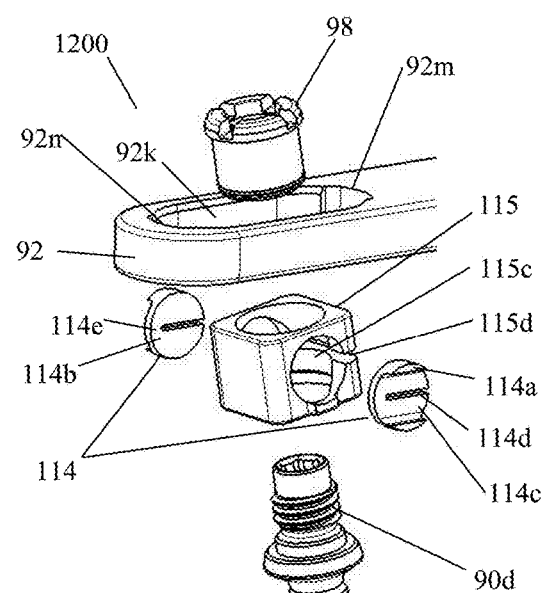
FIG. 80 is a fragmentary, exploded perspective view of an exemplary embodiment of a slider assembly that allows rotation.
Figure 81:
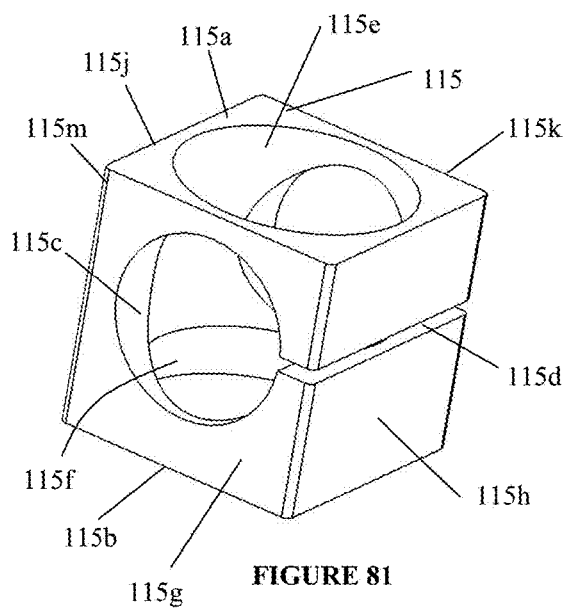
FIG. 81 is a perspective view of a rotation block of the assembly of FIG. 80.
Figure 82:
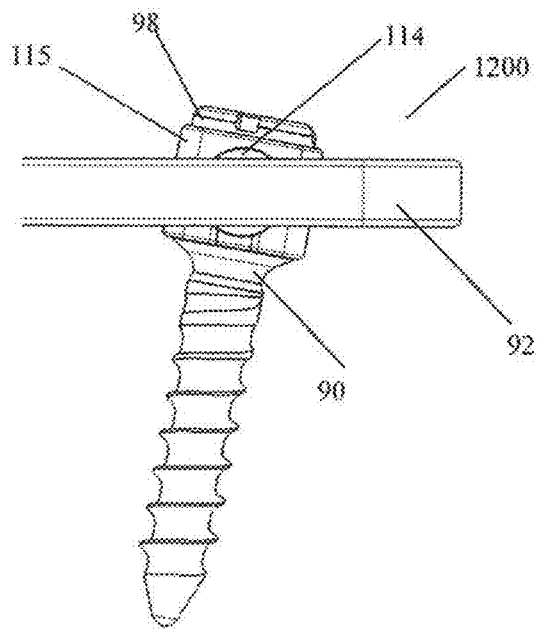
FIG. 82 is a fragmentary, side elevational view of the assembly of FIG. 80 with the screw locked at an angle.

Another variation of the assembly, as generally shown as 1200 and in FIG. 80, uses a flexible cube 115, slotted pins 114 that fit over the edges of the plate, and a locking approach whereby tightening locking nut 98 on the threads 90*d* of bone screw 90 cause the flexible cube 115 to compress against the pins 114, which compress against the top and bottom surfaces of the plate/rod construct 92 and lock the angle and location of the flexible cube 115 and assembly 1200. As shown in FIGS. 80 through 82, the flexible cube 115 has a top surface 115*a*, a bottom surface 115*b*, a front surface 115*h*, a back surface 115*j*, a first side 115*g*, and a second side 115*k*. A bore 115*e* extends through the flexible cube 115 from the top surface 115*a* to the bottom surface 115*b*, and a chamfer 115*f* extends from the bottom face 115*b* to the bore 115*e* and is configured to match the taper feature 90*g* on the bone screw 90. A side hole 115*c* extends through the cube 115 from first side 115*g* to second side 115*k*. This side hole 115*c* allows the pins 114 to fit and turn therewithin. A slot 115*d* allows the cube 115 to be flexible so that force on the top surface 115*a* and the bottom surface 115*b* causes the cube 115 to squeeze inward, thus reducing the diameter of opening 115*c* and apply pressure against the pins 114. The pins 114 have a front surface 114*a*, a back surface 114*b*, a slot 114*c* of a width to fit a width of plate 92 and a small slot 114*d*, which creates a small area of material/metal 114*e* that acts as a hinge to allow the pins 114 flexibility and to be compressed by the cube 115. As shown in FIG. 82, when the locking nut 98 is tightened on the threads 90*d* of the bone screw 90, the locking nut 98 and screw feature 90*g* compress the cube 115 against the pins 114, which causes pins 114 to compress against the plate 92, thereby locking the angulation and sliding of the assembly.

Figure 83:
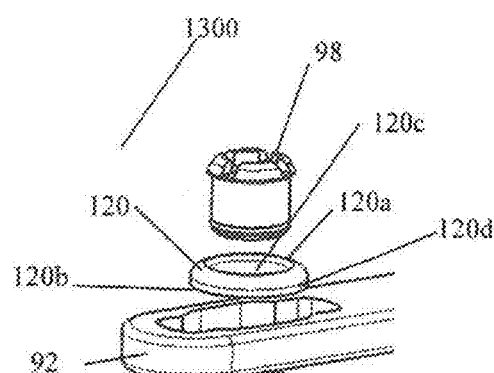
FIG. 83 is a fragmentary, exploded, perspective view of an exemplary embodiment of a slider assembly that allows polyaxial rotation.
Figure 86:
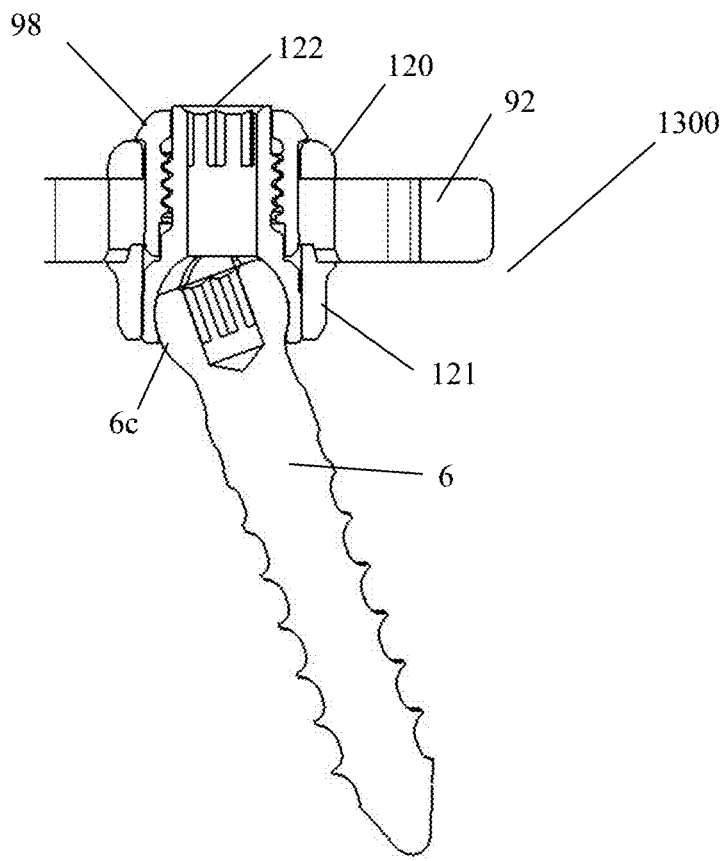
FIG. 86 is a fragmentary, cross-sectional view of the polyaxial assembly of FIG. 83.

FIG. 83 shows a variation of a polyaxial screw assembly 1300, which is similar to previous polyaxial assemblies. However, the key component 122 is effectively a collet with external threads. The locking nut 98 extends through a top washer 120 and plate 92 and engages sleeve 121. The collet 122 snaps over the head 6c of the bone screw 6. When the collet 122 is drawn up into the sleeve 121, the collet 122 is compressed against the screw head 6c while the washer 120 and sleeve 121 are simultaneously compressed against the plate/rod construct 92, thereby locking sliding and angulation. It is also possible to partially lock angulation and still have sliding capability until the locking nut 98 is turned further. The top washer 120, also shown in FIG. 86, is simply a washer with a top surface 120a and a bottom surface 120b configured to contact the surface of the plate/rod construct 92. An internal bore 120c allows the locking nut 98 to pass through.

Figure 84:
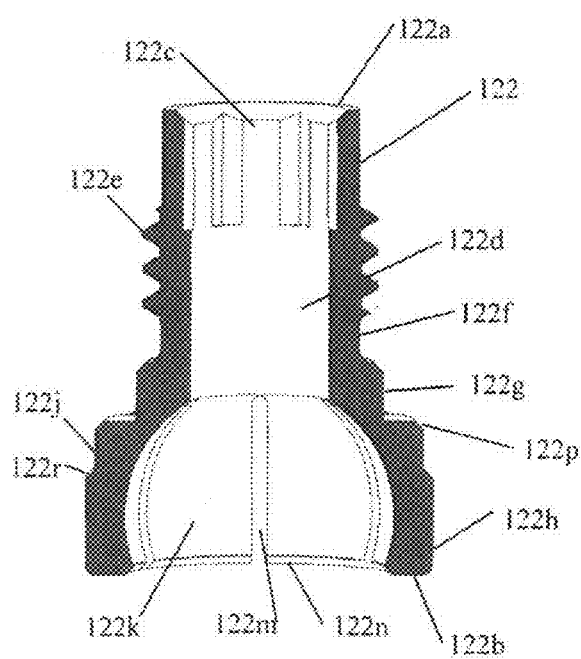
FIG. 84 is a cross-sectional view of a polyaxial body component of the assembly of FIG. 83.

FIG. 84 details the collet 122 of the polyaxial screw assembly 1300. The collet 122 has a top surface 122a, a bottom surface 122b, a driving feature 122c for engaging a driver instrument, and a bore 122d extending through the collet 122. A spherical seat 122k engages the head 6c of the bone screw 6. The head 6c of the bone screw 6 can be larger than the diameter of spherical seat 122k so that the screw head 6c causes interference with the spherical seat 122k and spreads the collet 122 outward. The slots 122m allow the collet 122 the flexibility to spread. These slots 122m can vary in height in number, as needed. A threaded portion 122e engages the threads 98d in the locking nut 98 and an undercut feature 122f eliminates any incomplete threads and allows locking nut 98 to fully seat and use the entire thread length, if necessary. The external collet section shown as 122h is configured to engage sleeve 121. While shown here as cylindrical, it can be tapered. Also, if the head 6c of the bone screw 6 is larger than the diameter of the spherical seat 122k, it will cause the collet 122 to flex outward, created a tapered shape. A small cylindrical section 122j allows the collet 122 to be partially drawn into sleeve 121 without causing a tightening of the assembly. Two chamfers 122p, 122r allow the collet 122 to slide within the sleeve 121 without catching on sharp edges. Of course, there are multiple variations possible, such as extending section 122h and eliminating the step 122j, or tapering the surface such that no step is necessary. The sleeve 121 can also have an internal taper to match or interfere with the tapered surface.

Figure 85:
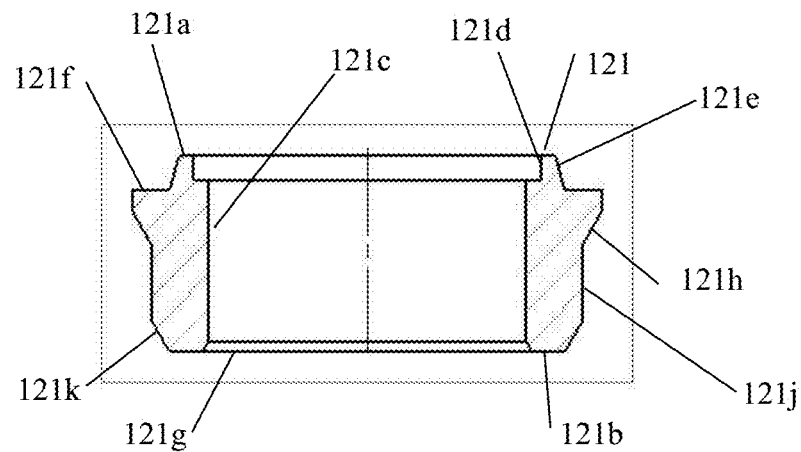
FIG. 85 is a cross-sectional view of a lower sliding component of the assembly of FIG. 83.

FIG. 85 shows sleeve 121 with an upper surface 121a and a lower surface 121b. A cylindrical bore 121c extends through the sleeve 121. It can also be tapered or partially cylindrical and partially tapered. A counter-bore 121d allows clearance for the bottom of the locking nut 98. A conical surface 121e engages with the plate rod construct 92 so that, as the assembly is tightened, the conical surface 121e engages the edge and/or chamfer on the plate rod construct 92 to assist in locking the sleeve 121 to the plate 92. If the edge is sharp or minimal radius, the edge will deform the conical face, which creates a binding and locking feature. The outer lip 121f of the sleeve creates a flat surface for engaging the bottom face of the plate rod construct 92 or prevents the sleeve 121 from travelling any further than necessary. If the conical feature 121e fully engages, the outer lip 121f may not engage part or all of the bottom of the plate 92. A chamfer 121g allows for easier assembly and sliding of the sleeve 121 on the collet 122.

Figure 87:
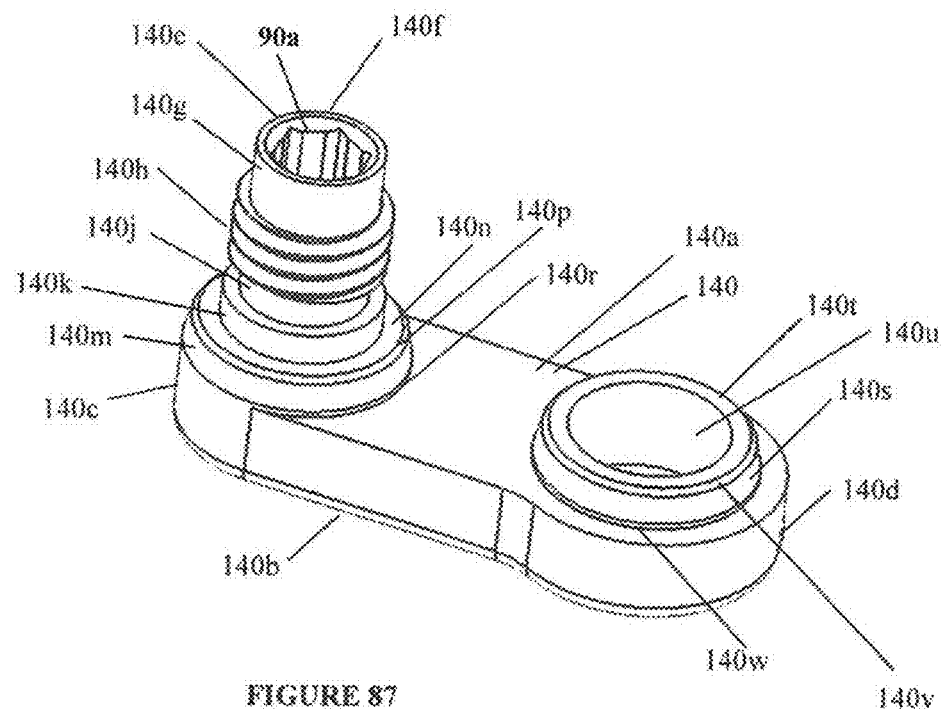
FIG. 87 is a perspective view of an exemplary embodiment of a two level connector from above.
Figure 88:
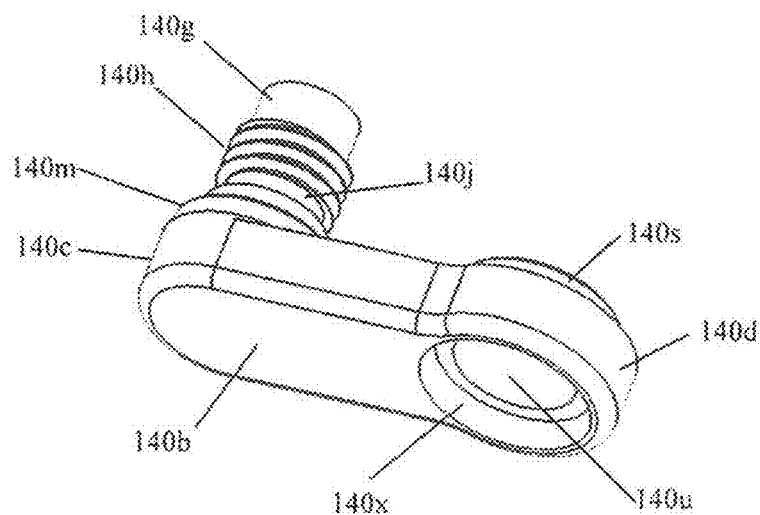
FIG. 88 is a perspective view of the two level connector of FIG. 87 from below.

FIG. 86 further shows assembly 1300 in a cross-sectional view to illustrate how the components engage when they are fully locked. By turning the locking nut 98, the collet 122 is drawn upwards into the sleeve 121. This movement compresses the collet 122 against the screw head 6c of the screw 6 and draws the sleeve 121 and the washer 120 against the plate rod construct 92. This action locks the angulation and location of the assembly within the construct 92. While angulation and sliding can be locked simultaneously, angulation can be locked or partially locked first by not completely tightening the locking nut 98, and then locked to the plate by further tightening. This is potentially beneficial in compression and distraction of the spine. FIGS. 87 and 88 show a connector 140 for expanding a single level construct into a multi-level construct. This connector 140 has a partially threaded post similar to a screw post and an opening to accept an extended screw post. This effectively adds an additional partially threaded post to a screw, thereby creating two threaded posts to attach rod/plate connectors. The connector 140 has a connector top surface 140a, a bottom surface 140b, a first rounded face 140c and a second face 140d. A partially threaded post 140e has a top surface 140f, a non-threaded region 140g, a threaded section 140h, and a recess 140j cut into a post 140k so that the recess 140j allows the threads to be good threads even at the bottom of the threads. The post 140e is machined or formed on top of a tapered section 140m and, as the post 140e is smaller than the top diameter of taper 140m, creates a shelf 140n. A chamfer 140p breaks the edge between the taper 140m and shelf 140n, which allows components seating on the taper 140m to find and engage the taper 140m without contacting a sharp edge. The connector 140 can be recessed relative to the start of taper 140m, which creates a small cylindrical feature 140r. This feature 140r can also be taller to create a taller overall post without affecting the critical dimensions of the remaining features above the cylindrical feature 140r. On the other end of the connector is a tapered feature 140s, which can be identical to 140m in dimensions. This is also on a small cylindrical section 140w, the height of which can be increased or reduced. The intersection of top surface 140t and taper 140s is chamfered 140v to avoid a sharp edge and allow interfacing components to find and seat on the taper 140s without engaging a sharp edge. A bore 140u passes through the connector 140 and is generally centered within the taper 140s. The bottom opening 140x of bore 140u, as seen in FIG. 88, matches the screw post base, which is preferably tapered. Thus, when the taper of a screw post contacts the preferred taper of 140x, the two rigidly engage. Of course, it is not necessary to have this feature be a taper, but just a cylindrical bore that contacts the base of the screw to make sure the connector can be secured in the right position relative to the height of the partially threaded post on the screw.

Figure 89:
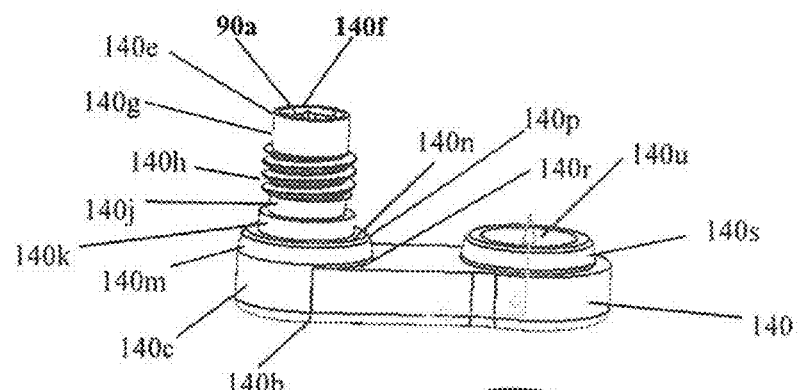
FIG. 89 is a fragmentary, exploded, perspective view of a partial assembly of the two level connector of FIG. 87 from a side thereof.

FIG. 89 clarifies the partial assembly of the connector 140 by showing a modified bone screw 142. As shown in FIG. 89, the post of the bone screw 142 has a partially threaded post section 142d and a non-threaded section 142e that is identical to the previously shown bone screws 90. The main difference in this bone screw 142 is that an extended section 142f is provided such that, when inserted in connector 140 and the assembly is locked, the height of the threads is correct to insure proper component assembly and locking. As per the other bone screws, a recess 142j is provided to allow a locking nut to be able to use the full length of the threads. The taper or chamfer 142g is the same as in the previous bone screws 90. The partial section 142t represents an area of bone screw threads, which are not illustrated.

Figure 90:
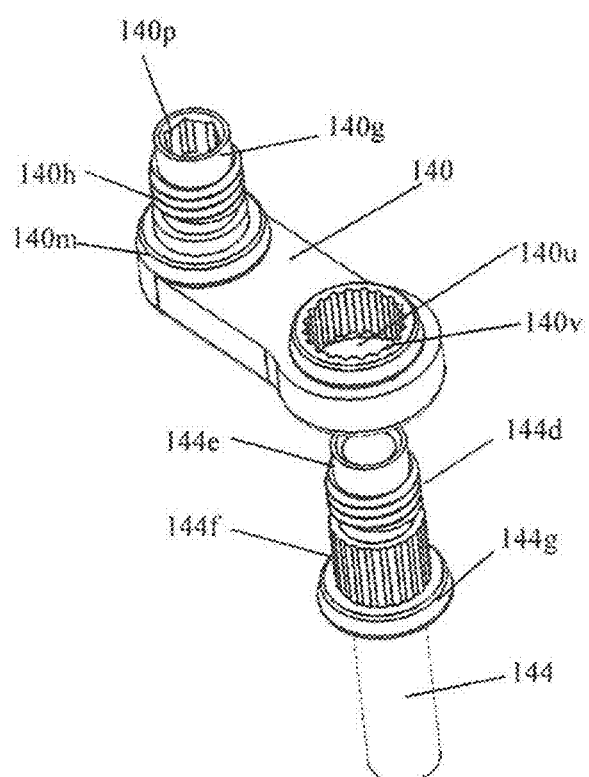
FIG. 90 is a fragmentary, exploded, perspective view of the two level connector assembly of FIG. 87 from above.

FIG. 90 shows the connector 140 with the addition of splines 140v and matching splines 144f on a bone screw 144. These splines 140f, 144f, once engaged, can assist in providing anti-rotational capability to the construct. Bone screw 144 has the same general features of bone screw 142, included the threaded portion 144d, the non-threaded portion 144e, and the tapered section 144g.

Figure 91:
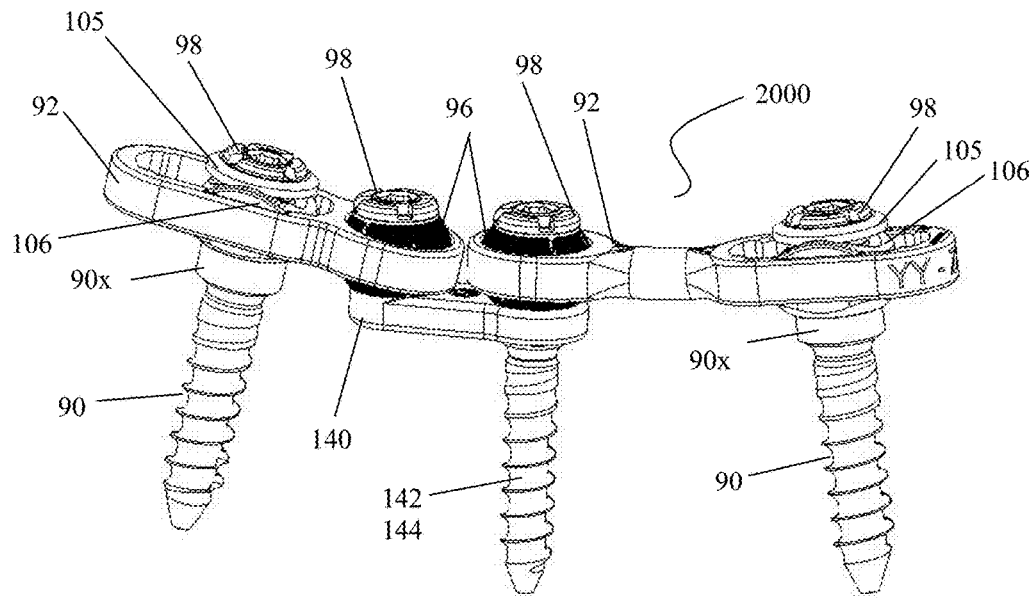
FIG. 91 is a perspective view of an exemplary embodiment of a two level construct assembly.

FIG. 91 shows a full two level assembly 2000 when connector 140 is used. As an alternative to this exemplary embodiment is an embodiment that directly connects the two plate constructs 92 to one another without the connector 140. To make such a connection, the non-threaded 142e and threaded 142d post sections of the bone screw 142 is/are lengthened so that two of the spherical bearings 96 can be stacked one on top of the other with the lengthened sections in the center of both bearings 96. In such a configuration, all that is needed is to place the extended post sections 142d, 142e through two plate constructs 92 having the recesses 92d of the spherical bearing sections one on top of the other, slide the two bearings 96 on the post sections 142d, 142e and into the two recesses 92d, to insert a single locking nut that is approximately twice as long as those locking nuts 98 through both bearings 96, and to thread the interior threads of the extended locking nut onto the threaded post section 142d. As can be seen, the connector 140 acts as a bridge providing an additional partially threaded post to attach another plate rod connector. In this example, the spherical bearing ends are facing each other. The connector 140 allows the spherical bearings 96 enough room for the bearings 96 to rotate until they are locked. Of course, the opposite slider ends can also attach to the connector 140. However, the sliders should be as far as possible to the end of the plate rod connectors to allow both plate rod connectors to fit. It is noted that, in this example, the bone screws 90 have a cylindrical extension 90x that raises the construct slightly off the bone for easier placement under certain anatomical conditions.

Figure 92:
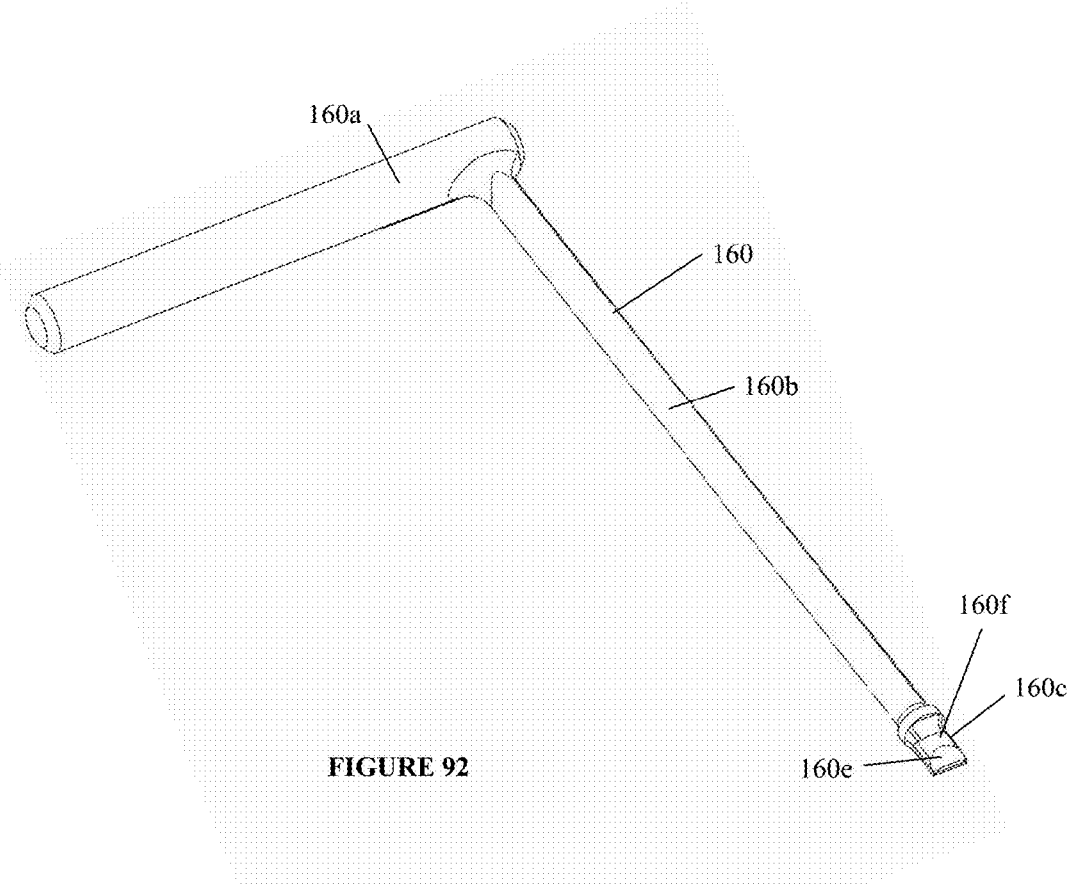
FIG. 92 is a perspective view of an exemplary embodiment of a compressor/distractor instrument.

FIG. 92 shows an instrument 160 for compression and distraction. This instrument 160 has a handle 160a, a shaft 160b, and a tip 160c. This tip 160c, shaped like a cam or screw driver blade has a leading edge 160e, which can be tapered or radiused for easier placement in a plate rod construct pocket, such as 30p, 60p, 92n, 92m, etc., and a face 160f. The face 160f can be flat, round, oval, cam shaped, or another shape. As the tip 160c is generally rectangular, the tip 160c creates a cam in function. When the handle 160a is turned, the tip 160c engages the slider and an edge of the pocket so that, the further the handle 160a is turned, the further the slider is displaced.

In surgical use, the most common application of the embodiments described and shown herein is in the treatment of the lumbar spine. Spinal screw assemblies or hooks having a saddle or opening for a rod are screwed into the pedicles or attached to a bone structure of the spine. This provides excellent visualization of the screw placement site and anatomy. Depending on the variation, either a bone screw with a spherical head or a threaded post is placed, or a combination of either. While the variations shown depict either one or the other, one skilled can see how the various features can be combined when multiple level plates with three or more screws are used.

When spherical head bone screws are used, polyaxial assemblies are snapped over the bone screw heads. Of course, the modular nature of the configuration allows the polyaxial screw assembly to be attached to the bone screw head first, and the entire assembly implanted as one piece. In a single level case whereby only two vertebrae are to be fused, a single plate is used, preferably on each side of the spine and right size selected. Either a measurement of the distance between the screws can be taken or a template used to determine the proper plate size. The slider and its variations allow for a single plate to cover a range of screw head distances, which significantly reduces inventory. Once the correct size plate is selected, the spherical end of the plate with bearing is snapped over the top of one of the screw heads, and the plate is adjusted and angled until the slider end of the plate captures the second screw head. The set screws are then tightened to lock the assembly.

When the slider variation is used, such as in assemblies generally shown in 100 and 200, tightening the set screw in the slider screw causes the screw head to expand, thereby spreading the slider outward to exert force against the inside of the plate and locking it in position. The inside of the plate and/or outside of the slider can also have teeth or a surface finish to provide the surgeon a way of temporarily holding the slider in the desired position.

The spherical interface is also locked by spreading of the screw bodies caused by tightening the set screw.

It may also possible to place the plate first and the screws through the plate. However, this is more difficult than having bone anchors pre-installed.

When Monoaxial screws are used, the same surgical procedure applies. Place the screws, measure the distance between the screws, select the correct plate, place the plate over the screws and lock the assembly. In the case of the monospherical screw, this screw eliminates the need for a spherical bearing in the end of the plate. However, the slider hole also becomes spherical to accept the spherical screw head. This allows more angulation and adjustment.

In a multilevel construct, one plate is stacked over the top of another plate. The advantage to this is that contouring of long plates is minimized or eliminated. In multilevel constructs, the pedicles are at compound angles and vary in medial-lateral offset. Thus, connecting a series of screws by a single long plate is challenging and often requires compromising the ideal position of the screws in the pedicles. By connecting two screws at a time, offset does not apply, as each plate connects only two screws.

The spherical bearing or monospherical screw compensates for angulation in all planes. Without such a connection to the plate, the plate would remain perpendicular to both screws, making it almost impossible to place. Of course, while the bearing is shown held within the plate assembly, it can also be pre-assembled on the screw body.

While discussed previously, the plate can be a plate but also a rod with features on the ends that match the features shown in the various figures and described accordingly. This approach allows the section between the ends to be round, which can have a few advantages. First, the stiffness to the construct can be matched to that of a 5.5 mm rod system, or any other desired stiffness. Also, components designed for round rods, such as off the shelf rod to rod connectors or crosslinks can directly attached to the round section, as can be other polyaxial screw systems, for the treatment of multiple levels. Side connectors can also be used to attach to the round section to treat multiple level fusions and fix to the spine. In addition, the round section can be readily contoured to better match the curvature of the spine while allow the surgeon the ability to do in-vivo bending, when necessary.

By providing the spherical bearing with slots, the bearing, such as that shown in FIG. 45, the bearing can be readily assembled in the plate, as it is flexible to be inserted within an opening in the plate/rod construct. With slots that extend from the top and bottom of the spherical bearing, the locking of the spherical bearing to the plate occurs by spreading the bearing outward by contact of the tapered surfaces on the screw and locking nut collar with the features inside the spherical bearing. This outward expansion is extremely efficient in engaging the seat in the plate rod construct and locking the sphere to the construct. Surface finish and material do affect the strength of the locking when tested. Ti-6Al-4V ELI with a machined tooth pattern works well, as does smooth Commercially Pure (CP) Titanium. Ti-6Al-4V ELI is harder and stronger than CP Titanium and does not work as well without surface roughness, as the surface is unable to effectively grip the edges of the plate/rod spherical seat. CP Titanium with surface roughness does not work as well either, as the material is too soft to hold the surface roughness without shearing the rough surface. Of course, there are different grades of titanium, and different alloys, each may have a different affect and require different surface or no surface treatment. The alloys chosen are based on their standard use in the industry, biocompatability, and properties.

Surface roughness on the spherical bearing can be applied in a number of ways, including machining, chemical etching, grit blasting, or other measures. It is preferable to provide a machined feature that creates small grooves around the surface. While this can be done as individual circular grooves, the machined pattern can be run in a helix, effectively creating a shallow thread over the spherical surface. It is preferable to create the surface over the entire spherical area to be certain that rotation of the sphere in the plate still maintains engagement of the surface roughness pattern with the edge of the spherical pocket in the plate regardless of the angulation of the spherical bearing when on the screw post.

While the plate is shown as having two separate openings, it is understood that the plate could have one opening with a slot in the middle of the plate connecting the openings, or multiple openings to accept an intermediate screw or instrument.

When the screw used is that shown as bone screw 90 with a threaded post 90*d*, the screw is placed first, as in the previous versions. As the assembly is placed over the screw posts, it is desirable to prevent the screw from rotating during locking and applying torque to the spine. Thus, the counter-torque tool engages the feature 90*a*, which may be a torx, hex, square drive, or other shape and allows the surgeon to prevent the screw from turning by preventing the counter-torque tool form turning while torque is being applied to the locking nut. In the preferred embodiment, the collar 99 free floats on the locking nut 98, which is highly beneficial because the collar minimizes unwanted torque being transferred to the sphere during tightening, which also minimizes torque to the plate/rod construct as the sphere engages the spherical seat. The counter torque tool can be cannulated to go over a k-wire for a minimally invasive approach. The nut driver can be placed over the counter-torque shaft and lowered until it engages the features in the locking nut 98. Torque is applied until the assembly torque is reached and the tools removed. This leaves a very low profile system.

For multilevel constructs, a simple connector 140 can be used to connect multiple plates. This configuration allows a single component along with an extended screw-post bone screw to handle more complex procedures with a minimum of added components. For example, in a two-level case, normal bone screws 90 are placed at either end of the construct and an extended post bone screw, such as shown as screws 142, 144, is placed in the middle pedicle. Connector 140 is then placed over the extended bone screw post. A distance between the screw heads is measured and the correct rod plate connectors are selected and secured to the threads on the screw heads by way of the locking nuts 98.

As the slider end allows for compression and distraction of the spine, as discussed previously, the surgeon can measure with a gauge and find the size desired based on whether compression or distraction is needed. As the slider has a set amount of travel, for example, 5 mm, it is helpful to know where the slider will be when the assembly is first attached to the bone screw posts. For example, if the pedicles are 25 mm apart and the surgeon wants to decompress and expand the distance to 30 mm, the plate/rod construct should be sized so that the spherical bearing opening and the slider opening are at 25 mm but where the slider is at the end of the travel towards the spherical end. This configuration allows for placement and a full 5 mm of decompression. Of course, if this is reversed so that the pedicles are 25 mm apart but the surgeon wants to compress the spine to 20 mm, the initial position of the slide should be at the far end away from the spherical bearing, thus allowing full travel length back towards the spherical bearing. In the case of a need to do temporary compression or distraction, the implants can be tightened, the necessary procedure done, the implants loosened and adjusted to the proper distance, and the assembly re-tightened. It is also possible to simply provide temporary friction or pre-lock of components by not applying the full locking torque to either end of the assembly.

As the spine flexes in multiple planes, stabilization of the spine on only one side of the spinous process is insufficient. Therefore, in a normal spinal procedure, stabilization of the spine requires implants and fixation on both sides of the spinous process. For example, in a single level fusion of L4-L5 of the lumbar spine, bone screws are inserted into both pedicles on L4 and both pedicles of L5. The screws are then connected by one of the plate-rod constructs described herein on each side of the spinous process, i.e., the screws on the left of the spinous process are connected and the screws on the right side of the spinous process are connected. This creates two multi-plate constructs that run in the cephalad-caudad direction to provide support to the spine during the fusion process. By using the connector, as shown in FIGS. 87 to 91, a longer screw post 144 or screw section 142*f*, or an extended screw body as shown in FIGS. 33 and 34, allows two plate construct 92 ends to be stacked on top of each other. In this way, it is possible to create plate constructs 92 that extend over a multiple pedicle or multiple vertebral length. By combining plate constructs as indicated, there is no limitation on the length of the construct chain or the number of levels that can be treated. Different length plate constructs can be combined to compensate for variations in distance between bone screws placed in the pedicles.

As the assembly is self-contained and small, it is possible to supply the plate/rod construct assembly complete and sterile packed, and to provide a range of sterile sizes ready for surgery. As can be understood, this implant system also requires a minimal number of instruments, simplifying the surgical implant procedure and allowing the instruments to be supplied in a sterile state.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The phrase "at least one of A and B" is used herein and/or in the following claims, where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables.

The foregoing description and accompanying drawings illustrate the principles, exemplary embodiments, and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An orthopedic fixation device, comprising:
   a bearing defining a bearing internal bore and having:
      a rounded exterior surface;
      an upper surface, an intermediate surface, and a lower surface; and
      at least one slot in the bearing extending from the exterior surface to the internal bore; and
   a retaining portion defining a recess shaped to accept the exterior surface of the bearing therein such that:
      in a steady state of the bearing, the bearing can move within the recess; and
      when force is imparted against the upper and lower surfaces of the bearing, the bearing deforms outwardly to expand the rounded exterior surface and fix the bearing in place within the recess.

2. The fixation device according to claim 1, wherein the bearing has a spherically shaped exterior in the steady state and the exterior of the bearing deforms from spherical to removably fix the bearing in place within the recess.

3. The fixation device according to claim 1, wherein the bearing has an ovoid shaped exterior in the steady state and the exterior of the bearing deforms from ovoid to removably fix the bearing in place within the recess.

4. The fixation device according to claim 1, wherein:
   the upper surface of the bearing internal bore is an upper, outwardly chamfered surface; and
   the lower surface of the bearing internal bore is a lower, outwardly chamfered surface.

5. The fixation device according to claim 1, wherein:
   the upper surface of the bearing internal bore is an arcuate surface; and
   the lower surface of the bearing internal bore is an arcuate surface.

6. The fixation device according to claim 1, wherein:
   the force is forces imparted against the upper and lower surfaces of the bearing; and
   when the forces are imparted against the upper surface and the lower surface of the bearing, the bearing deforms outwardly to fix the bearing in place within the recess.

7. The fixation device according to claim 1, wherein the at least one slot in the bearing is at least one slot that extends from the upper surface to the lower surface.

8. The fixation device according to claim 1, wherein the at least one slot in the bearing is:
   at least one first blind slot having an open end at the upper surface, a blind end adjacent the lower surface, and extending from the open end at the upper surface to the blind end; and
   at least one second blind slot having an open end at the lower surface, a blind end adjacent the upper surface, and extending from the open end at the lower surface to the blind end.

9. The fixation device according to claim 8, wherein:
   the at least one first blind slot is a plurality of first blind slots; and
   the at least one second blind slot is a plurality of second blind slots.

10. The fixation device according to claim 9, wherein at least some of the plurality of first blind slots are symmetrically disposed about the bearing internal bore.

11. The fixation device according to claim 9, wherein at least some of the plurality of second blind slots are non-symmetrically disposed about the bearing internal bore.

12. The fixation device according to claim 9, wherein the plurality of second blind slots are disposed about the bearing internal bore offset from the plurality of first blind slots.

13. The fixation device according to claim 1, wherein the at least one slot in the bearing is:
   one slot that extends from the upper surface to the lower surface; and
   at least one first blind slot extending from at least one of the upper surface and the lower surface.

14. The fixation device according to claim 1, wherein the recess is shaped to allow pitch, roll, and yaw movement of the bearing therein.

15. The fixation device according to claim 1, wherein the bearing internal bore is shaped to fit therein a portion of a fastener comprising:
   at least one bone screw having:
      a screw portion shaped to screw into bone; and
      a head with a nut connection section having:
         exterior threads; and
         an expanded section between the exterior threads and the screw portion and wider in diameter than the exterior threads and the screw portion and having an upper chamfered surface tapering inwards and away from the screw portion from a larger outer diameter to a smaller inner diameter to correspond in shape with the lower surface of the bearing internal bore; and
   at least one locking nut having:
      a nut internal bore with interior threads shaped to mate with the exterior threads of the nut connection section to connect the at least one locking nut to the at least one bone screw;
      an exterior wall having a given outer diameter to fit within intermediate surface of the bearing internal bore;

a head having a head outer diameter greater than the given outer diameter;
a lower lip having a lip outer diameter greater than the given outer diameter; and
a lower-facing, chamfered surface tapering from the head at the head diameter to the exterior wall at the given outer diameter to correspond in shape with the upper surface of the bearing internal bore, the exterior wall being disposed between the lower lip and the upper chamfered surface.

16. The fixation device according to claim 15, wherein the at least one locking nut is a locking nut assembly having:
a locking nut having the nut internal bore, the exterior wall, the head, and the lower lip; and
a collar having the lower-facing, chamfered surface and being a separate component from the locking nut and configured to rotate about the exterior wall.

17. The fixation device according to claim 15, wherein, when the bearing is placed within the recess, and the head of the at least one bone screw is placed through the bearing internal bore, and the at least one locking nut is removably attached to the nut connection section to secure the bone screw head, the bearing, and the at least one locking nut therein, the bearing permits the bone screw head to at least partially roll, pitch, and yaw within the recess relative to the retaining portion.

18. The fixation device according to claim 15, wherein the exterior wall and the lower lip of the at least one locking nut are shaped to removably retain the at least one locking nut within a portion of the bearing internal bore.

19. The fixation device according to claim 15, wherein the recess is shaped to accept the bone screw head, the bearing, and the at least one locking nut therein.

20. The fixation device according to claim 15, wherein the at least one locking nut has features shaped to connect to a tool that removably connects the at least one locking nut to the nut connection section of the at least one bone screw.

21. The fixation device according to claim 1, wherein:
the bearing internal bore is shaped to fit therein a portion of a fastener comprising:
at least one bone screw having:
a screw portion shaped to screw into bone; and
a head with a nut connection section having:
exterior threads; and
an expanded section between the exterior threads and the screw portion and wider in diameter than the exterior threads and the screw portion and having an upper surface directed inwards and away from the screw portion from a larger outer diameter to a smaller inner diameter to correspond in shape with the lower surface of the bearing internal bore; and at least one locking nut having:
a nut internal bore with interior threads shaped to mate with the exterior threads of the nut connection section to connect the at least one locking nut to the at least one bone screw;
an exterior wall having a given outer diameter to fit within intermediate surface of the bearing internal bore;
a head having a head outer diameter greater than the given outer diameter;
a lower lip having a lip outer diameter greater than the given outer diameter; and
a lower-facing surface directed from the head at the head diameter to the exterior wall at the given outer diameter to correspond in shape with the upper surface of the bearing internal bore, the exterior wall being disposed between the lower lip and the upper chamfered surface; and when the head of the at least one bone screw is placed through the bearing internal bore and the at least one locking nut is attached to the nut connection section to secure the bearing between the upper surface of the at least one bone screw and the lower-facing surface of the at least onelocking nut, the bearing expands at the upper surface and the lower surface circumferentially as the at least one locking nut is tightened onto the exterior threads.

22. The fixation device according to claim 1, wherein:
the bearing internal bore is shaped to fit therein a portion of a fastener having a screw portion and a head with a nut connection section; and
the portion of the fastener that the bearing internal bore is shaped to fit is the nut connection section of the head of the screw.

23. An orthopedic fixation device, comprising:
a bearing defining a bearing internal bore and having:
a rounded exterior surface;
an upper surface, an intermediate surface, and a lower surface; and
at least one slot in the bearing extending from the exterior surface to the internal bore; and
a retaining portion:
having a recess, an upper edge, and a lower edge; and
being shaped to accept the bearing therein such that:
in a steady state of the bearing, the bearing can move within the recess; and
when force is imparted against the upper and lower surfaces of the bearing, the bearing deforms outwardly to expand the rounded exterior surface to engage the upper and lower edges and fix the bearing in place in the recess.

* * * * *